US012780815B2

(12) United States Patent
Reim et al.

(10) Patent No.: US 12,780,815 B2
(45) Date of Patent: Nov. 3, 2026

(54) PROCESS FOR THE PRODUCTION OF FERROPORTIN INHIBITORS

(71) Applicant: Vifor (International) AG, St. Gallen (CH)

(72) Inventors: Stefan Reim, St. Gallen (CH); Erik Philipp, St. Gallen (CH); Maria Wilhelm, St. Gallen (CH); Cyrill Blatter, St. Gallen (CH)

(73) Assignee: Vifor (International) AG, St. Gallen (CH)

( * ) Notice: Subject to any disclaimer, the term of this patent is extended or adjusted under 35 U.S.C. 154(b) by 846 days.

(21) Appl. No.: 17/913,631

(22) PCT Filed: Mar. 23, 2021

(86) PCT No.: PCT/EP2021/057424

§ 371 (c)(1),
(2) Date: Sep. 22, 2022

(87) PCT Pub. No.: WO2021/191202

PCT Pub. Date: Sep. 30, 2021

(65) Prior Publication Data

US 2023/0212159 A1 Jul. 6, 2023

(30) Foreign Application Priority Data

Mar. 24, 2020 (EP) .................................... 20165358

(51) Int. Cl.
*C07D 413/14* (2006.01)

(52) U.S. Cl.
CPC ........ *C07D 413/14* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 10,364,239 B2 | 7/2019 | Dürrenberger et al. |
| 11,129,820 B2 | 9/2021 | Morris et al. |
| 2004/0138268 A1 | 7/2004 | Boy et al. |
| 2017/0320865 A1 | 11/2017 | Kuduk et al. |

FOREIGN PATENT DOCUMENTS

| | | | |
|---|---|---|---|
| CN | 108290878 A | 7/2018 |
| JP | 2018-535203 A | 11/2018 |
| JP | 2018-536641 A | 12/2018 |
| WO | 2011029832 A1 | 3/2011 |
| WO | WO-2016/065583 A1 | 5/2016 |
| WO | WO-2017/068089 A2 | 4/2017 |
| WO | WO-2017/068090 A1 | 4/2017 |
| WO | WO-2018/192973 A1 | 10/2018 |
| WO | 2021191202 A1 | 9/2021 |

OTHER PUBLICATIONS

Veronese, et al., One-Pot synthesis of 2-Vinyilimidazole Derivatives by Reaction of α-Hydroxyimino β-dicarbonyl Compounds with Allylamine, Communications-Synthesis, (1985) pp. 300-302.
Knutson, et al., Iron release from macrophages after erythrophagocytosis is up-regulated by ferroportin 1 overexpression and down-regulated by hepcidin, Proceedings National Academy of Sciences, vol. 102 (2002) pp. 1324-1328.
Dürrenberger, et al., Functional Characterization of Fluorescent Hepcidin, American Chemical Society Publications, vol. 24 (2013) pp. 1527-1532.
Bonaccorsi Di Patti, et al., A structural model of human ferroportin and of its iron pinding site, The FEBS Journal, vol. 281 (2014) pp. 2851-2860.
International Search Report, corresponding to PCT/EP2021/057424, dated Mar. 23, 2021, 15 pages.
Besselievre, Francois et al.; "C-H Bond Activation: A Versatile Protocol for the Direct Arylation and Alkenylation of Oxazoles"; Synthesis, No. 20; Sep. 3, 2009; pp. 3511-3518.
Hoffman, Thomas J. et al.; "Stereoselective Synthesis of the C1-C11 and C12-C34 Fragments of Mycalolide A"; Organic Letters, vol. 12, No. 15; Jul. 15, 2010; 71 pages.
Hodgetts, Kevin J. et al.; "Ethyl 2-Chlorooxazole-4-carboxylate: A Versatile Intermediate for Synthesis of Substituted Oxazoles"; Organic Letters, vol. 4, No. 17; Jul. 23, 2002; pp. 2905-2907.
Japanese Patent Office; Notice of Reasons for Refusal; Japanese Patent Application No. 2025-131977; Aug. 12, 2026; 17 pages.

*Primary Examiner* — Noble E Jarrell
(74) *Attorney, Agent, or Firm* — Foley & Lardner LLP

(57) ABSTRACT

The invention relates to a new process for preparing compounds of the formula (I)

(I)

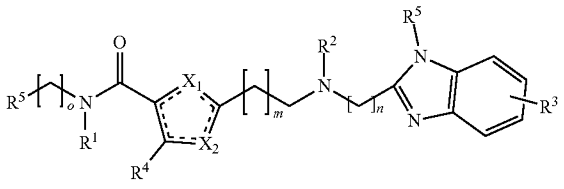

and pharmaceutically acceptable salts thereof, which act as ferroportin inhibitors being suitable for the use as medicaments in the prophylaxis and/or treatment of diseases caused by a lack of hepcidin or of iron metabolism disorders leading to increased iron levels or increased iron absorption, including iron overload, thalassemia, sickle cell disease and hemochromatosis.

22 Claims, 8 Drawing Sheets

Specification includes a Sequence Listing.

PXRD pattern of Compound (II) in the form of the 3HCl salt; polymorph form PM1

PXRD pattern of Compound (II) in the form of the 3HCl salt; polymorph form PM2

PXRD pattern of Compound (II) in the form of the 3HCl salt; polymorph form PM3

PXRD pattern of Compound (II) in the form of the $H_2SO_4$ salt

PXRD pattern of Compound (II) in the form of the $1H_3PO_4$ salt

PROCESS FOR THE PRODUCTION OF FERROPORTIN INHIBITORS

CROSS-REFERENCE TO RELATED APPLICATIONS

This application claims priority to International Patent Application No. PCT/EP2021/057424 filed 23 Mar. 2021, and to European Patent Application No. 20165358.1 filed 24 Mar. 2020, both of which are hereby incorporated by reference in their entireties.

INTRODUCTION

The invention relates to a new process for preparing compounds of the formula (I)

(I)

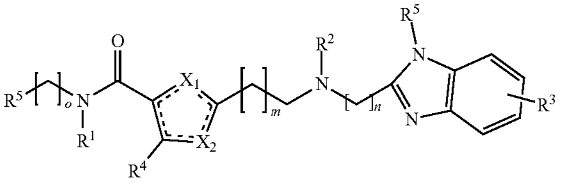

and pharmaceutically acceptable salts thereof. The compounds of the general formula (I) of the present invention act as ferroportin inhibitors and are thus particularly suitable for the use as medicaments in the prophylaxis and/or treatment of diseases caused by a lack of hepcidin or of iron metabolism disorders leading to increased iron levels or increased iron absorption. The compounds of the general formula (I) of the present invention are further particularly suitable for the use in the prophylaxis and/or treatment of iron overload, including thalassemia, sickle cell disease and hemochromatosis, as well as for the use in the prophylaxis and/or treatment of diseases related to or caused by increased iron levels, increased iron absorption or iron overload.

BACKGROUND AND PRIOR ART

Iron is an essential trace element for almost all organisms and is relevant in particular with respect to growth and the formation of blood. The balance of the iron metabolism is in this case primarily regulated on the level of iron recovery from haemoglobin of ageing erythrocytes and the duodenal absorption of dietary iron. The released iron is taken up via the intestine, in particular via specific transport systems (DMT-1, ferroportin), transferred into the blood circulation and thereby conveyed to the appropriate tissues and organs (transferrin, transferrin receptors).

Mammalian organisms are unable to actively discharge iron. The iron metabolism is substantially controlled by hepcidin, a peptide hormone produced in the liver, via the cellular release of iron from macrophages, hepatocytes and enterocytes. Hepcidin acts on the absorption of iron via the intestine and via the placenta and on the release of iron from the reticuloendothelial system. In the body, hepcidin is synthesized in the liver from what is known as pro-hepcidin, pro-hepcidin being coded by the gene known as the HAMP gene. The formation of hepcidin is regulated in direct correlation to the organism's iron level, i.e. if the organism is supplied with sufficient iron and oxygen, more hepcidin is formed, if iron and oxygen levels are low, or in case of increased erythropoiesis less hepcidin is formed. In the small intestinal mucosal cells and in the macrophages hepcidin binds with the transport protein ferroportin, which conventionally transports the phagocytotically recycled iron from the interior of the cell into the blood.

The transport protein ferroportin is a transmembrane protein consisting of 571 amino acids which is formed in the liver, spleen, kidneys, heart, intestine and placenta. In particular, ferroportin is localized in the basolateral membrane of intestinal epithelial cells. Ferroportin bound in this way thus acts to export the iron into the blood. In this case, it is most probable that ferroportin transports iron as $Fe^{2+}$. If hepcidin binds to ferroportin, ferroportin is transported into the interior of the cell, where its breakdown takes place so that the release of the phagocytotically recycled iron from the cells is then almost completely blocked. If the ferroportin is inactivated, for example by hepcidin, so that it is unable to export the iron which is stored in the mucosal cells, the stored iron is lost with the natural shedding of cells via the stools. The absorption of iron in the intestine is therefore reduced, when ferroportin is inactivated or inhibited, for example by hepcidin. In addition, ferroportin is markedly localized in the reticuloendothelial system (RES), to which the macrophages also belong. On the other hand, if the serum iron level decreases, hepcidin production in the hepatocytes of the liver is reduced so that less hepcidin is released and accordingly less ferroportin is inactivated, allowing a larger amount of stored iron to be transported into the serum.

Therefrom it becomes apparent that the hepcidin-ferroportin system directly regulates the iron metabolism and that a disorder of the hepcidin regulation mechanism therefore has a direct effect on iron metabolism in the organism. In principle the hepcidin-ferroportin regulation mechanism acts via the two following opposite principles:

On the one hand, an increase of hepcidin leads to inactivation of ferroportin, thus blocking the release of stored iron from the cells into the serum, thus decreasing the serum iron level. In pathological cases a decreased serum iron level leads to a reduced hemoglobin level, reduced erythrocyte production and thus to iron deficiency anemia.

On the other hand, a decrease of hepcidin results in an increase of active ferroportin, thus allowing an enhanced release of stored iron and an enhanced iron uptake e.g. from the food, thus increasing the serum iron level. In pathological cases an increased iron level leads to iron overload.

Iron overload states and diseases are characterized by excess iron levels. Therein, the problems arise from excess serum iron level which lead to non-transferrin bound iron (NTBI). The NTBI is rapidly taken up unspecifically by the organs, leading to an accumulation of iron in tissue and organs. Iron overload causes many diseases and undesired medical conditions, including cardiac, liver and endocrine damage. Further, iron accumulation in brain has been observed in patients suffering from neurodegenerative diseases such as for example Alzheimer's disease and Parkinson's disease. As a particular detrimental aspect of excess free iron the undesired formation of radicals must be mentioned. In particular iron (II) ions catalyze the formation (inter alia via Fenton reaction) of reactive oxygen species (ROS). These ROS cause damage to DNA, lipids, proteins and carbohydrates which has far-reaching effects in cells, tissue and organs and is well known and described in the literature to cause the so-called oxidative stress.

Besides the conventional methods for treating iron overload by removing iron from the body e.g. with chelating agents such as deferoxamine (also known as desferrioxamine B, N'-{5-[acetyl(hydroxy)amino]pentyl}-N-[5-({4-[(5-aminopentyl)(hydroxy)amino]-4-oxobutanoyl}amino)pentyl]-N-hydroxysuccinamide or Desferal®), deferasirox (Exjade®, 4-(3,5-bis(2-hydroxyphenyl)-1H-1,2,4-triazol-1-yl)benzoic acid) and deferiprone (Ferriprox®, 3-hydroxy-1, 2-dimethylpyridin-4 (1H)-one), compounds acting as hepcidin agonists or having an inhibiting or supporting effect on the biochemical regulatory pathways in the iron metabolism, such as hepcidin mimetic peptides have been described. Said therapeutic approaches are based on a direct involvement into the disturbed iron metabolism pathway by directly acting via the primary regulator hepcidin by providing a hepcidin mimetic or a hepcidin agonist, i.e. acting in the sense of a kind of hepcidin substitute or supply. The approach is based on the therapeutic rationale to treat iron overload, i.e. excess serum iron level, by inhibiting ferroportin, via the hepcidin-inactivation mechanism, thus blocking excessive iron absorption.

Ferroportin inhibitors according to the formula (I) of the present invention and methods for preparing the same have been described in WO2017/068089 and in WO2017/068090. The preparation methods described therein afford 12 process steps comprising several chromatographic process steps, leading to a preparation process of low efficiency, which is time, cost and effort consuming. The process described therein is further characterized by comparably low yields and some of the process steps create safety and technical problems due to the formation of critical by-products.

Further, the international application WO2018/192973 describes the preparation and crystallization of various specific salts of selected ferroportin inhibitors described therein and as described in WO2017/068089 and in WO2017/068090.

WO2011/029832 relates to thiazole and oxazole compounds which act as hepcidin antagonists being described as suitable in the use for the treatment of iron deficiency diseases and describes a process according to synthesis route 3) for preparing said compounds. The process described therein also comprises multiple process steps with chromatographic separation and purification steps and is thus also unfavourable under efficiency viewpoints.

A. C. Veronese et al. "*One-Pot Synthesis of 2-Vinylimidazole Derivatives by Reaction of α-Hydroxyimino-β-dicarbonyl Compounds with Allylamine;* 1985) describe a one-pot synthesis reaction to obtain 2-vinylimidazole derivatives but remain silent about compounds according to the formula (I), (II) or (II') and to selected intermediates of the present invention or a process for the preparation thereof.

Object

The object of the present invention was to provide, a new method for preparing selected ferroportin inhibitors defined by the general formula (I) of the present invention and of pharmaceutically acceptable salts thereof. The new method should be improved with respect to at least one of the aspects increased yield, process efficiency, reduction of process steps, improvement of resources e.g. by using commercially available or cheaper starting compounds or by using starting and intermediate compounds which can be prepared in a time, cost and effort efficient manner, by avoiding as far as possible chromatographic process steps, by increasing the working safety, avoiding critical or harmful by-products, avoiding critical reaction components such as Sn reagents and by reducing intermediate isolation steps as far as possible. It was a further object of the invention to provide a new process which provides ferroportin inhibitor compounds with improved impurity profile and/or in higher purity compared to compounds available by known methods.

Accordingly, a further object of the invention relates to providing ferroportin inhibitor compounds of high purity and with improved impurity profile.

A further aspect relates to providing new ferroportin inhibitor compounds, which has been solved with the novel compounds according to formula (II').

The object has been solved by providing the novel and improved process for preparing selected ferroportin inhibitors defined by the general formula (I) of the present invention and of pharmaceutically acceptable salts thereof.

DESCRIPTION OF THE INVENTION

In a first aspect the present invention provides a new process for preparing compounds of the general formula (I)

(I)

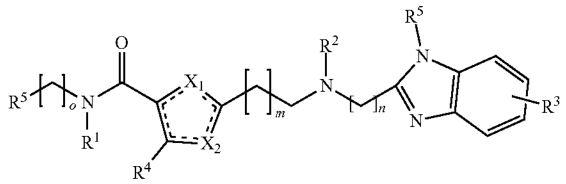

comprising the step of reacting a compound of the formula (IM-3) with a compound of the formula (RM-3)

(IM-3)

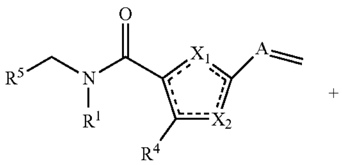

+

(RM-3)

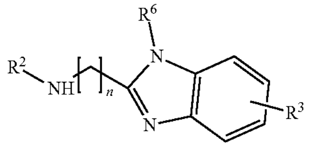

to provide the compound of the formula (I);

wherein $X^1$ is N, S or O; and $X^2$ is N, S or O;

with the proviso that one of $X^1$ and $X^2$ is N and that $X^1$ and $X^2$ are different;

m is an integer of 1, 2, or 3;

n is an integer of 1, 2, 3 or 4;

is an integer of 1, 2, 3 or 4;

A represents a CH-group, a $CH_2$—CH-group or a $CH_2$—$CH_2$—CH-group;

$R^1$ and $R^2$ are independently selected from the group consisting of hydrogen and $C_1$-$C_4$-alkyl, which may be substituted with 1 or 2 substituents;

$R^3$ represents 0, 1, 2 or 3 substituents, which may independently be selected from the group consisting of halogen,
cyano,
$C_1$-$C_4$-alkyl,
$C_1$-$C_3$-halogenoalkyl;
$C_1$-$C_4$-alkoxy, and
a carboxyl group;

$R^4$ is selected from the group consisting of
hydrogen,
halogen,
$C_1$-$C_3$-alkyl, and
$C_1$-$C_3$-halogenoalkyl;

$R^5$ is selected from the group consisting of
aryl which may carry 1 to 3 substituents, and
mono- or bicyclic heteroaryl which may carry 1 to 3 substituents; and $R^6$ is selected from the group consisting of
hydrogen,
halogen,
$C_1$-$C_4$-alkyl, which may be substituted with 1 or 2 substituents;
$C_1$-$C_3$-halogenoalkyl.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" or "optional substituent(s)" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

The term "comprising" when used in the claims or specification includes "consisting of".

If within the present specification any item is referred to as "as mentioned herein" or "as defined (anywhere) herein," it means that it may be mentioned anywhere in the present specification or may have the meaning as defined anywhere in the present specification.

The terms as mentioned in the present specification have the following meanings:

The term "halogen" or "halogen atom" means a fluorine, chlorine, bromine or iodine atom, particularly a fluorine, chlorine or bromine atom, a preferred selection relates to chlorine or fluorine, a further preferred selection relates to bromine or fluorine, most preferred is fluorine.

The term "$C_1$-$C_4$-alkyl" means a linear or branched, saturated, monovalent hydrocarbon group having 1, 2, 3, or 4 carbon atoms, e.g. a methyl, ethyl, n-propyl, isopropyl, n-butyl, sec-butyl, isobutyl or a tert-butyl group etc., or an isomer thereof. The term "$C_1$-$C_3$-alkyl" means a linear or branched, saturated, monovalent hydrocarbon group having 1, 2 or 3 carbon atoms, e.g. a methyl, ethyl, n-propyl or isopropyl group.

The $C_1$-$C_4$-alkyl or $C_1$-$C_3$-alkyl group may optionally be substituted with 1 or 2 substituents, preferably with 1 substituent. Such optional substituents are preferably selected from the group consisting of: halogen (forming a halogen-substituted $C_1$-$C_4$-alkyl or $C_1$-$C_3$-alkyl group as defined below), $C_3$-$C_6$-cycloalkyl containing preferably 3, 4, 5 or 6 carbon atoms, such as preferably cyclopropyl, mono- or bicyclic heteroaryl as defined below, such as preferably a benzimidazolyl group, an amino group as defined below, a carboxyl group, an aminocarbonyl group as defined below.

The term "$C_1$-$C_3$-halogenoalkyl" means a linear or branched, saturated, monovalent hydrocarbon group in which the term "$C_1$-$C_3$-alkyl" has the meaning as defined above, and in which one or more of the hydrogen atoms are replaced, identically or differently, with a halogen atom. Particularly, said halogen atom is a fluorine atom. More particularly, all said halogen atoms are fluorine atoms ("$C_1$-$C_3$-fluoroalkyl"). Said $C_1$-$C_3$-halogenoalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl, wherein a trifluoromethyl-group is particularly preferred.

The term "$C_1$-$C_4$-alkoxy" means a linear or branched, saturated, monovalent group of formula ($C_1$-$C_4$-alkyl)-O—, in which the term "$C_1$-$C_4$-alkyl" is as defined supra, e.g. a methoxy, ethoxy, n-propoxy, isopropoxy, n-butoxy, sec-butoxy, isobutoxy or tert-butoxy group, or an isomer thereof, with a methoxy-group being particularly preferred.

The term "carboxyl group" indicates a group [—(C═O)—OH].

The term "aminocarbonyl group" indicates a group [$NH_2$—(C═O)—].

The term "amino group" includes amino (—$NH_2$), mono- or dialkylamino (alkyl-NH—, $(alkyl)_2N$—), wherein with respect to "alkyl" reference can be made to the definition of $C_1$-$C_4$-alkyl and $C_1$-$C_3$-alkyl above. Preferred is an amino group (—$NH_2$) and mono- or dimethylamino. Most preferred is an amino group (—$NH_2$).

The term "aryl" includes aromatic hydrocarbon residues containing 6 to 14 carbon atoms (excluding the carbon atoms of the possible substituents), which may be monocyclic or bicyclic, including, for example: phenyl, naphthyl, phenanthrenyl and anthracenyl, which may optionally be substituted by 1, 2 or 3 of the same or different substituents selected from hydroxy, halogen as defined above such as preferably F, Br and Cl, cyano, a carboxyl group as defined above, amino as defined above, $C_1$-$C_4$-alkyl or $C_1$-$C_3$-alkyl as defined above such as preferably methyl, $C_1$-$C_3$-halogenoalkyl as defined above such as preferably trifluoromethyl, and $C_1$-$C_4$-alkoxy as defined above such as preferably methoxy.

Optionally substituted phenyl is preferred, such as unsubstituted phenyl and phenyl which is substituted with 1 to 3, more preferably with 1 or 2 substituents, which may be the same or different. The 1 to 3 phenyl substituents are in particular selected from the group as defined above.

The term "mono- or bicyclic heteroaryl" includes heteroaromatic hydrocarbon residues containing 4 to 9 ring carbon atoms, which additionally preferably contain 1 to 3 of the same or different heteroatoms from the series S, O, N in the ring and therefore preferably form 5- to 12-membered heteroaromatic residues which may preferably be monocyclic but also bicyclic. Preferred aromatic heterocyclic residues include: pyridyl (pyridinyl), pyridyl-N-oxide, pyridazinyl, pyrimidyl, pyrazinyl, thienyl (thiophenyl), furyl, pyrrolyl, pyrazolyl, imidazolyl, triazolyl, thiazolyl, oxazolyl or isoxazolyl, indolizinyl, indolyl, benzo[b]thienyl, benzo

[b]furyl, indazolyl, quinolyl, isoquinolyl, naphthyridinyl, quinazolinyl, quinoxalinyl. 5- or 6-membered aromatic heterocycles are preferred, such as from the group of 5-membered heteroaryl, for example thiazolyl such as thiazol-2-yl, 2-thiazol-2-yl, 2-thiazol-4-yl, thienyl (thiophenyl) such as thien-3-yl, pyrazolyl such as 1-pyrazol-4-yl, 3-pyrazol-5-yl, imidazolyl such as imidazole-2-yl, 2-imidazol-4-yl, 1-imidazol-4-yl, triazolyl such as 1-triazol-3-yl, 1-triazol-4-yl, such as 1,2,4-triazol-3-yl or 1,2,3-triazol-4-yl, oxazolyl such as 2-oxazol-4-yl, 2-oxazol-5-yl, oxadiazolyl such as 1,2,4-oxadiazol-3-yl and from the group of 6-membered heteroaryl, for example pyridyl (pyridinyl) such as pyrid-1-yl, pyrid-2-yl, pyrid-3-yl, pyrid-4-yl, 2-pyrid-4-yl, 2-pyrid-6-yl, 3-pyrid-5-yl (pyridin-1-yl, pyridin-2-yl, pyridin-3-yl, pyridin-4-yl, 2-pyridin-4-yl, 2-pyridin-6-yl, 3-pyridin-5-yl, pyrimidin-2-yl, pyrimidin-4-yl, pyrimidin-5-yl, and from the group of bicyclic heteroaromatic residues in particular benzimidazolyl such as benzimidazol-2-yl, benzimidazol-4-yl, benzimidazol-5-yl.

The aforementioned heteroaryl-groups may carry one or more, preferably 1, 2 or 3, more preferably 1 or 2 same or different substituents, which are in particular selected from hydroxy, halogen as defined above such as preferably F, Br and Cl, cyano, a carboxyl group as defined above, amino as defined above, $C_1$-$C_4$-alkyl or $C_1$-$C_3$-alkyl as defined above such as preferably methyl, $C_1$-$C_3$-halogenoalkyl as defined above such as preferably trifluoromethyl, and $C_1$-$C_4$-alkoxy as defined above such as preferably methoxy.

A particularly preferred mono- or bicyclic heteroaryl-group is a pyridinyl-group, which carries 1, 2 or 3 substituents selected from the group defined above. Preferably the pyridinyl group carries 1 or 2 substituents, more preferred is one substituent. The 1, 2 or 3 optional pyridinyl-substituents are preferably selected from $C_1$-$C_3$-alkyl as defined above such as in particular methyl, halogen as defined above such as in particular fluorine and bromine (with fluorine being most preferred) and $C_1$-$C_3$-halogenoalkyl as defined above such as in particular trifluoromethyl. Most preferred is one substituent (indicated as $R_y$) forming a group represented by the formula

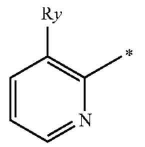

wherein * indicates the binding position and $R_y$ indicates the substituent which is selected from $C_1$-$C_3$-alkyl such as preferably methyl, halogen such as preferably fluorine or bromine and $C_1$-$C_3$-halogenoalkyl such as preferably trifluoromethyl, wherein more preferred is fluorine or bromine, most preferred is fluorine.

Aspects of the Invention

In a first aspect the present invention provides a new process for preparing the compounds of the general formula (I) as defined herein, wherein an intermediate compound of the formula (IM-3) is reacted with a compound of the formula (RM-3) to provide the compound of the formula (I):

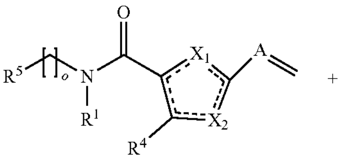

(IM-3)

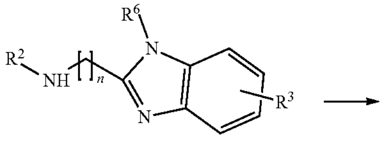

(RM-3)

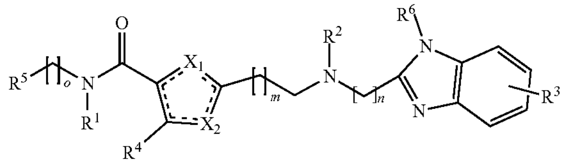

(I)

Therein "A" represents a CH-group, a $CH_2$—CH-group or a $CH_2$—$CH_2$—CH-group, depending on the desired resulting alkylene-chain length defined by $[\ ]_m$. Using a group "A" being a CH-group results in a chain length with m=1. Using a group "A" being a $CH_2$—CH-group results in a chain length with m=2. Using a group "A" being a $CH_2$—$CH_2$—CH-group results in a chain length with m=3.

Said process step is preferably carried out under alkaline conditions at elevated temperatures between 30° C. and 90° C. Alkaline conditions can be achieved by adding a suitable base, including inorganic and organic bases such as those mentioned below. Preferred bases are lithium hydroxide and sodium hydroxide.

In a second aspect of the invention the novel process may further comprise the additional step of preparing the intermediate compound of the formula (IM-3) by reacting an intermediate compound of the formula (IM-2) with a compound of the formula (RM-2)

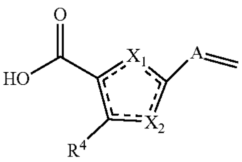

(IM-2)

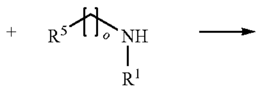

(RM-2)

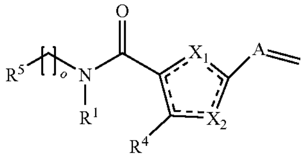

(IM-3)

wherein $X^1$, $X^2$, o, A, $R^1$, $R^4$, and $R^5$ have the meaning as defined above.

Said process step for preparing the intermediate compound (IM-3) may be carried out prior to the process step for preparing the compound (I) as shown above. Said process step is preferably carried out using methylmorpholine and ethylchloroformate in DCM (dichloromethane). The reaction is preferably carried out under cooling, preferably at temperatures below 10° C.

The compound (RM-2) used in said process step is preferably in the form of a salt, such as in particular in the form of a HCl salt.

The resulting intermediate compound (IM-3) may be extracted by aqueous HCl extraction at pH 1 and crystallized from water, followed by usual filtration and drying steps to isolate the intermediate compound (IM-3).

In a third aspect of the invention the novel process may further comprise the additional step of preparing the intermediate compound of the formula (IM-2) by converting a compound (RM-1) into the compound (IM-1) followed by ester cleavage

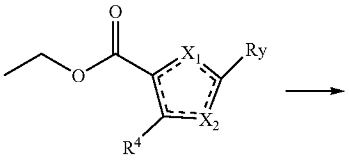

(RM-1)

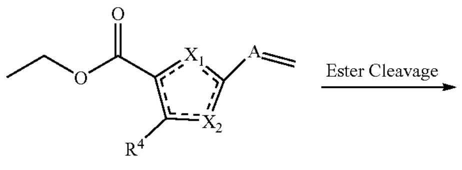

(IM-1)

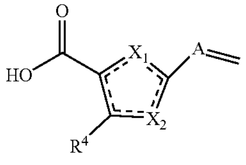

(IM-2)

wherein $R_y$ represents hydrogen or halogen, such as preferably chlorine, and $X^1$, $X^2$, A and $R^4$ have the meaning as defined anywhere herein.

Therein, ester cleavage can be carried out by ester hydrolysis using conventional methods. Preferably ester cleavage of the compound (IM-1) is carried out using a suitable base, including inorganic and organic bases such as those mentioned below. Preferred bases are lithium hydroxide and sodium hydroxide.

The reaction can be carried out in any suitable solvent, comprising those as listed below. Preferably THF (tetrahydrofurane) and water are used and the reaction is preferably carried out at room temperature (23° C.±3° C.).

In a fourth aspect of the invention the novel process may comprise the step of preparing the intermediate compound of the formula (IM-1) according to the following reaction scheme a):

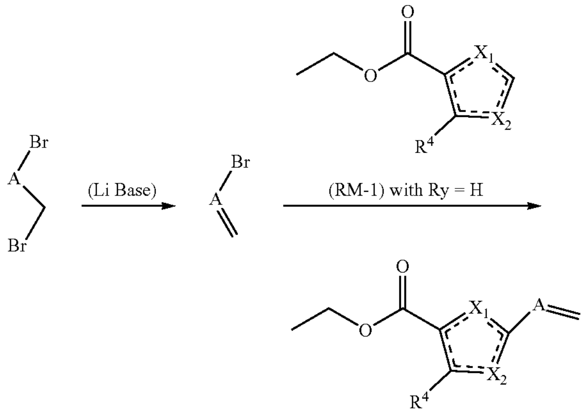

(IM-1)

wherein $X^1$, $X^2$ A and $R^4$ have the meaning as defined anywhere herein.

Said process step for preparing the compound (IM-1) is preferably carried out at elevated temperatures >40° C. Any suitable solvent comprising those as listed below can be used. Preferably the reaction is carried out in THF.

Further, the reaction is carried out, using a suitable catalyst, including e.g. $Pd(PPh_3)_4$, $Pd_2(dba)_3$, $Pd(OAc)_2/PPh_3$, $Pd(dppf)Cl_2$xDCM, Pd/C. It is particularly preferred to use $Pd(PPh_3)_4$ (Tetrakis(triphenylphosphine)palladium (0)) as the catalyst in said reaction.

Alternatively, the preparation of (IM-1) can be done by direct use of the bromo-alkene in gaseous form or in form of a commercially available solution in organic solvent In an alternative aspect the intermediate compound of the formula (IM-2) is prepared by converting a compound (RM-1), wherein $R_y$ has the meaning of Cl, into the compound (IM-1) followed by ester cleavage as described above:

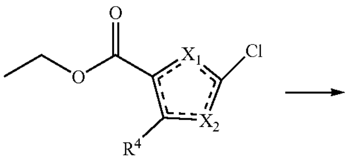

(RM-1)

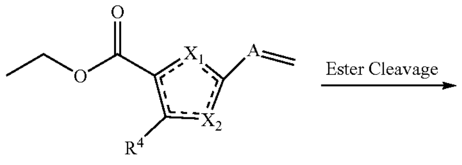

(IM-1)

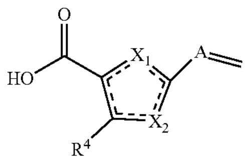

(IM-2)

wherein $X^1$, $X^2$ A and $R^4$ have the meaning as defined anywhere herein.

Therein, the process step for preparing (IM-1) can be carried out using tributyl(vinyl)tin, as described below in Step 1-a', according to reaction scheme b):

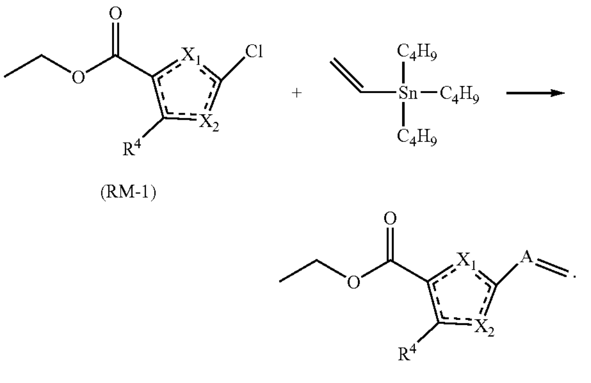

(RM-1)

(IM-1)

In a further alternative aspect of the invention the step of preparing the intermediate compound of the formula (IM-1) is carried out by reacting a compound (RM-1), wherein $R_y$ has the meaning of Cl, with vinylboronic acid pinacol ester to form the compound (IM-1) according to reaction scheme c):

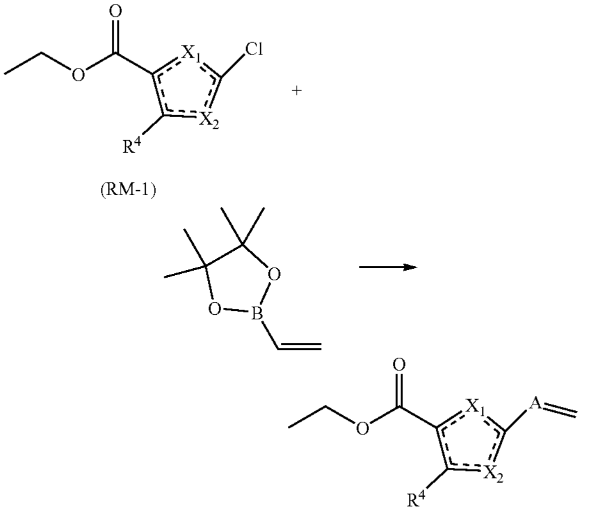

(RM-1)

(IM-1)

wherein $X^1$, $X^2$, A and $R^4$ have the meaning as defined anywhere herein.

This process step is advantageous as no tin (Sn) reagent is required, which results in less environmental damage, less costs and less health risks for people carrying out the process.

In a fifth aspect of the invention the compound IM-1 is prepared from a compound RM-1, wherein $R_y$ is hydrogen, as described above, followed by converting the compound IM-1 into the intermediate compound IM-2 by ester cleavage and said reactions are carried out in one combined step in a one-pot reaction. Such telescoped reaction scheme has the advantage of increased efficiency due to less intermediate isolation and purification steps. The reaction time and effort can be reduced remarkably and several chromatographic steps can be avoided.

In a sixth aspect of the invention the compound IM-3 is prepared from a compound IM-1 via the in-situ formation of the intermediate compound IM-2 and addition of the compound RM-2 and said reaction is carried out in a combined (telescoped) reaction in a one-pot reaction. Such telescoped reaction scheme has the advantage of increased efficiency due to less intermediate isolation and purification steps. The reaction time and effort can be reduced remarkably and several chromatographic steps can be avoided.

In a seventh aspect of the invention the compound IM-3 is prepared via a further telescoped reaction, wherein a compound RM-1 is converted into the intermediate compound IM-1 similar as described above, which is subsequently transferred into the intermediate compound IM-2 by ester cleavage, followed by conversion into the intermediated compound IM-3 by addition of compound RM-2. Such telescoped reaction scheme has the advantage to further increase the efficiency due to further reduced intermediate isolation and purification steps. The reaction time and effort can be further reduced and chromatographic steps can be avoided.

In an eighth aspect of the invention the compound (I) is prepared via two telescoped reaction steps, wherein the first telescoped reaction step corresponds to the preparation of the intermediate compound IM-3 as described in the seventh aspect supra, and the second telescoped reaction step comprises the conversion of the intermediate compound IM-3 into the compound (I) in situ, followed by its salt formation to achieve the preferred salts of the compounds (I) of the present invention.

In a preferred aspect of the invention the process for preparing the compound (I) is carried out as described anywhere herein and the resulting free base of the compound of formula (I) is isolated by phase separation (solvent extraction) or direct separation of the resulting oil product phase (oil separation).

In a preferred aspect the present invention relates to a process for preparing compounds of the general formula (I) as described herein, wherein the substituent $R^5$ represents a monocyclic heteroaryl group, which may carry 1 to 3 substituents, as defined above. Therein, the 1, 2 or 3 optional substituents of $R^5$ may independently be selected from the group consisting of $C_1$-$C_3$-alkyl as defined above such as preferably methyl, halogen as defined above such as preferably fluorine or bromine (among which fluorine is more preferred), and $C_1$-$C_3$-halogenoalkyl as defined above such as preferably trifluoromethyl.

In a particularly preferred aspect the present invention relates to a process for preparing compounds of the general formula (I) as described herein, wherein the substituent $R^5$ is a group represented by

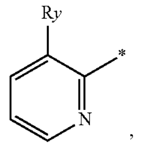

, wherein * indicates the binding position and $R_y$ is selected from the group consisting of $C_1$-$C_3$-alkyl as defined above such as preferably methyl, halogen as defined above such as preferably fluorine or bromine (among which fluorine is more preferred), and $C_1$-$C_3$-halogenoalkyl as defined above such as preferably trifluorometHy. Therein it is particularly preferred that $R_y$ is fluorine or bromine (among which fluorine is more preferred).

In a further particular aspect, the present invention provides a novel process for preparing compounds of the general formula (I) as defined herein, comprising the following reaction steps:

Step 1:

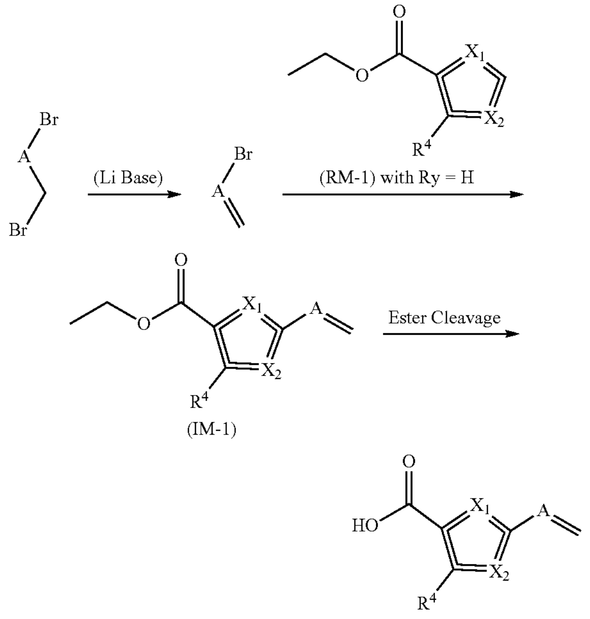

(IM-1)
(IM-2)

Step 2:

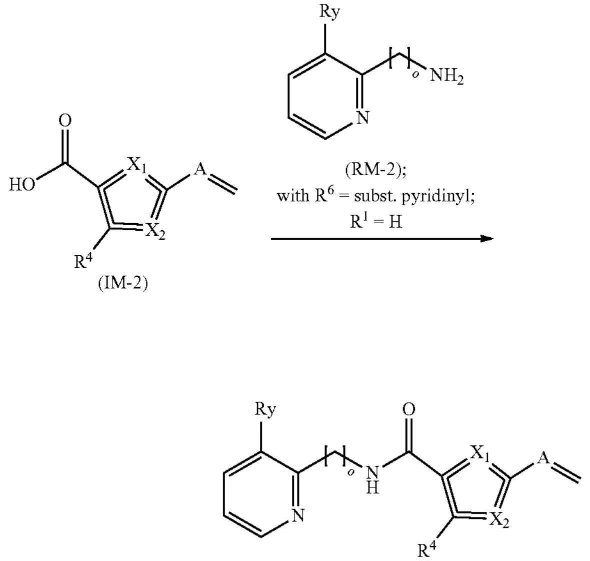

(IM-2)
(IM-3);
with $R^6$ = subst. pyridinyl;
$R^1$ = H

Step 3:

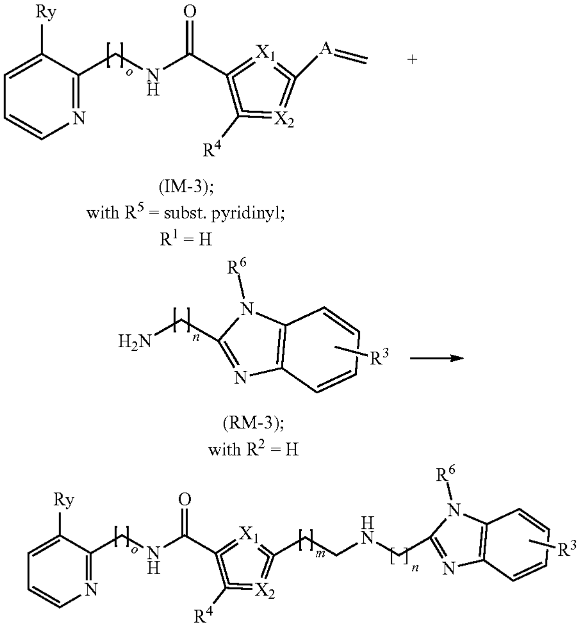
(IM-3);
with $R^5$ = subst. pyridinyl;
$R^1$ = H
(RM-3);
with $R^2$ = H
(I);
with $R^5$ = subst/ pyridinyl;
$R^1$, $R^2$ = H wherein $X^1$, $X^2$, $R^3$, $R^4$, $R^6$, $R_y$, A, m, n and o have the meaning as defined anywhere herein.

Said process steps 1, 2 and 3 are preferably carried out under the process conditions described above.

Preferably, the reaction steps 1 and 2 are carried out in one telescoped one-pot reaction step.

Further preferred aspects of the present invention relate to the new process for preparing compounds of the formula (I), wherein one or more of the following conditions are realized:

The substituent "A" represents a CH-group and m represents 1; and/or
o represents 1; and/or
$R^1$ and $R^2$ each represent hydrogen; and/or
$R^4$ represents hydrogen; and/or
$R^6$ represents hydrogen; and/or
$R^3$ represents hydrogen; and/or
$X^1$ is N and $X^3$ is O or S, forming a group

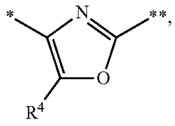
or
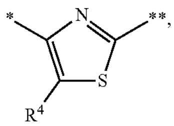

or $X^1$ is O or S and $X^2$ is N, forming a group

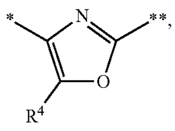
or
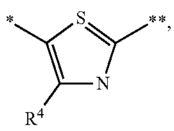

wherein in each case * indicates the binding position to the carbonyl-group and ** indicates the second binding position, and $R^4$ independently has the meaning as defined anywhere herein;

preferably $X^1$ is N and $X^3$ is O or S, forming a group

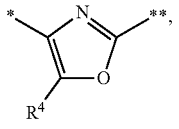
or
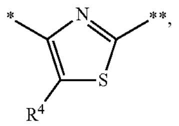

wherein in each case * indicates the binding position to the carbonyl-group and ** indicates the second binding position, and $R^4$ independently has the meaning as defined anywhere herein;

more preferably $X^1$ is N and $X^3$ is O, forming a group

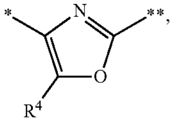

wherein * indicates the binding position to the carbonyl-group and ** indicates the second binding position, and $R^4$ has the meaning as defined anywhere herein.

A particularly preferred aspect of the present invention relates to the novel process for preparing compounds of the general formula (I) as defined herein, comprising the reaction steps 1, 2 and 3 as defined above, wherein $X^1$ represents N;

$X^2$ represents O;

A represents a CH-group;

m represents 1;

n represents 2; and represents 1.

Therein, it is further preferred that $R_y$ represents a halogen atom; and $R^4$ is selected from the group consisting of hydrogen, halogen as defined above, preferably chlorine, $C_1$-$C_3$-alkyl as defined above, preferably methyl, and $C_1$-$C_3$-halogenoalkyl as defined above, preferably trifluoromethyl.

It is even more preferred that therein $R_y$ represents fluorine or bromine (among which fluorine is more preferred); and $R^3$, $R^4$ and $R^6$ each represent hydrogen.

Accordingly, a preferred aspect of the invention relates to a process as described herein, wherein the compound (RM-1) is represented by the formula (RM-1-a):

(RM-1-a)

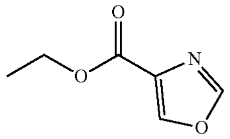

and/or wherein the compound (IM-1) is represented by the formula (IM-1-a):

(IM-1-a)

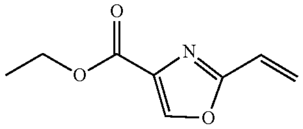

and/or wherein the compound (RM-2) is represented by the formula (RM-2-a) or (RM-2-a'):

(RM-2-a)

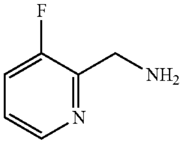
or (RM-2-a')

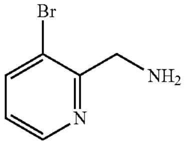

preferably in the form of the HCl salt:

(RM-2-a)

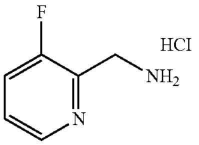
or (RM-2-a')

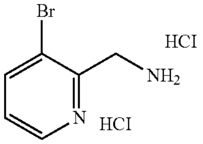

and/or wherein the compound (RM-3) is represented by the formula (RM-3-a):

(RM-3-a)

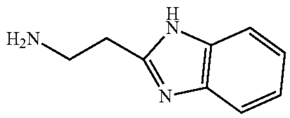

The process of the present invention is particularly preferred for preparing compounds of the formula (II):

(II)

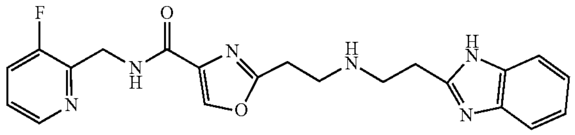

or of the formula (II'):

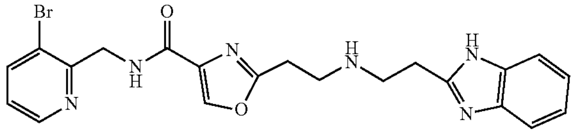 [SMILES: O=C(NCc1ncccc1Br)c1coc(CCNCCc2nc3ccccc3[nH]2)n1]

and pharmaceutically acceptable salts thereof, in particular the salts as described herein.

Thus, a particular aspect of the present invention relates a process for preparing compounds of the formula (II) or (II') and the pharmaceutically acceptable salts thereof, comprising the following process steps:

Step 1-a:

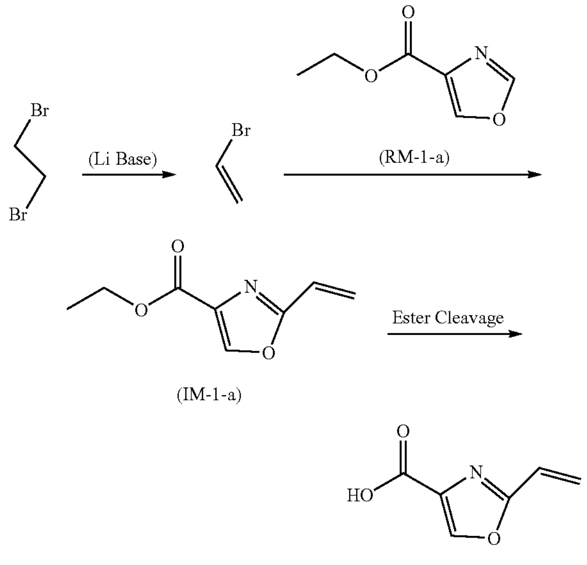

(IM-1-a)

(IM-2-a)

Step 2-a or 2-a', Respectively:

(Step 2-a):

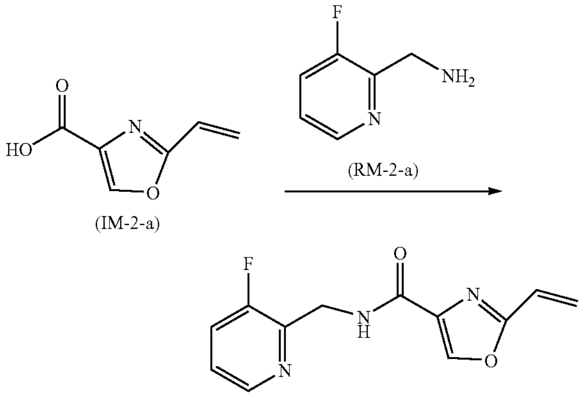

(IM-2-a)

(IM-3-b)

or (Step 2-a'):

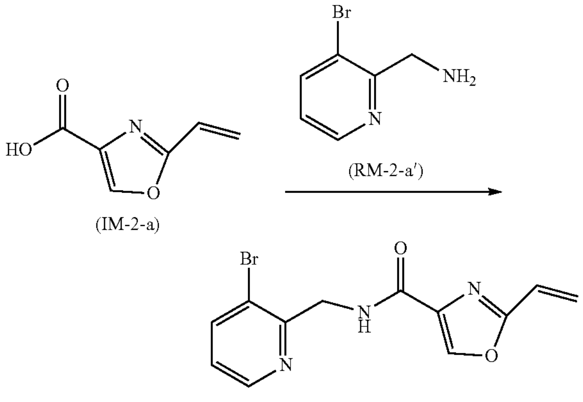

(IM-2-a)

(IM-3-b')

Step 3-a or 2-a', Respectively:

(Step 3-a):

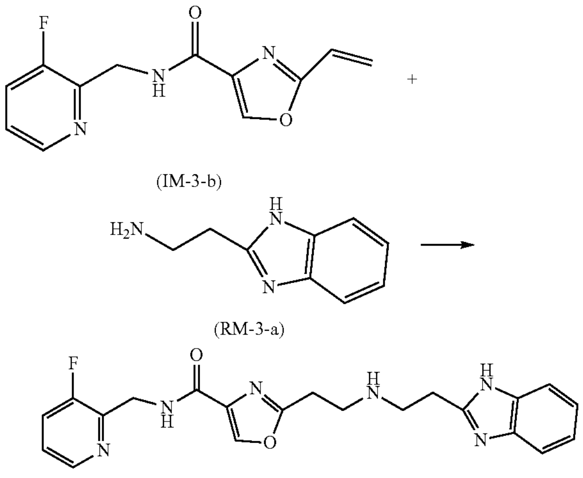

(IM-3-b)

(RM-3-a)

(II)

or (Step 3-a'):

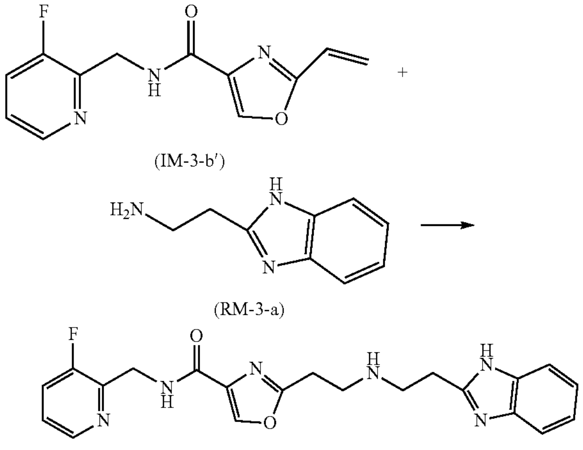

(IM-3-b')

(RM-3-a)

(II')

Preferably, the reaction steps 1-a and 2-a are carried out in one telescoped one-pot reaction step.

The preferred process conditions, bases, solvents and catalysts as described above are preferably used in the process described herein.

In a further aspect of the present invention said particular process comprises the following alternative (but less preferred) process step 1-a', starting with the compound RM-1 wherein $R_y$ is chlorine and $R^4$ is hydrogen, indicated herein as RM-1-a', followed by the process steps 2-a and 3-a as described above for preparing compounds of the formula (II) or (II') and the pharmaceutically acceptable salts thereof:

Step 1-a':

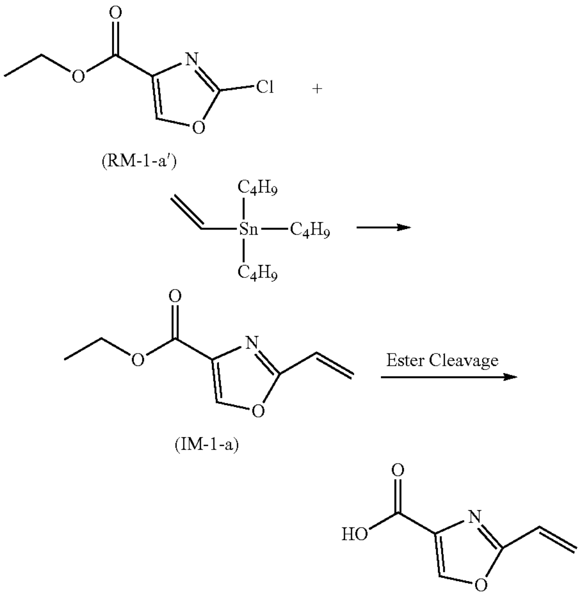

(RM-1-a') (IM-1-a) (IM-2-a)

In a further aspect of the present invention it is particularly preferred to prepare the intermediate compound (IM-1-a) via the following alternative (preferred) process step 1-a'', starting with the compound RM-1 wherein $R_y$ is chlorine and $R^4$ is hydrogen, indicated herein as RM-1-a':

Step 1-a'':

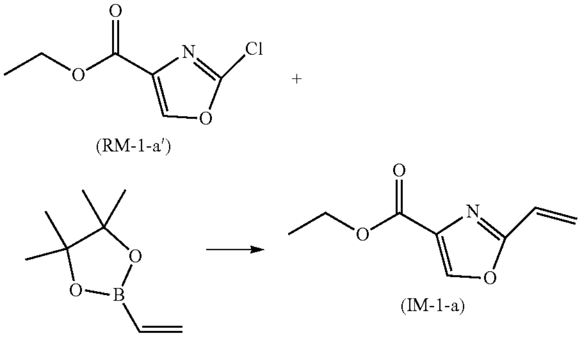
(RM-1-a') (IM-1-a)

As described above, the resulting intermediate compound (IM-1-a) can be used in the subsequent process steps described herein for preparing compounds of the formula (II) or (II') and the pharmaceutically acceptable salts thereof, such as in particular by subjecting the compound (IM-1-a) to ester cleavage to form compound (IM-2-a), followed by process steps 2-a and 3-a as described above.

Generally, in the process of the invention as described anywhere herein a wide range of inorganic and organic bases can be used, including lithium hydroxide, sodium hydroxide, potassium hydroxide, calcium hydroxide, lithium carbonate, sodium carbonate, potassium carbonate, calcium carbonate, sodium fluoride and potassium fluoride. Preferred are sodium hydroxide, lithium hydroxide, potassium hydroxide, sodium carbonate and potassium carbonate. Most preferred are lithium hydroxide and sodium hydroxide.

Further, in the process of the invention as described anywhere herein a wide range of solvents can generally be used, including e.g. methanol, ethanol, propanol, butanol, ethyl acetate (EtOAc), propyl acetate, iso-propyl acetate, acetonitrile, butyronitrile, heptane, cyclohexane, methylcyclohexane, dichloromethane (DCM) toluene, xylenes, chlorobenzene, dichlorobenzenes, 1,4-dioxane, tetrahydrofuran (THF), 2-methyl-tetrahydrofurane, 2,5-dimethyl-tetrahydrofurane, methyl-tertbutyl-ether, cyclopentyl-methyl-ether, N,N-dimethylformamide, water, and mixtures thereof. Preferred are ethanol, ethyl acetate, iso-propyl acetate, dichloromethane (DCM), tetrahydrofuran (THF), water and mixtures thereof. Particularly preferred are the solvents used in the Examples described below.

In a further aspect of the present invention the process for preparing the compounds of the general formula (I) or (II) or (II') as described anywhere herein comprises the additional step of converting the compound of the formula (I) or (II) or (II') into a pharmaceutically acceptable salt or solvate thereof using the corresponding bases or acids and/or solvents.

Preferably the compounds of the formula (I) or (II) or (II') are converted into a pharmaceutically acceptable salt with acids selected from the group consisting of benzoic acid, citric acid, fumaric acid, hydrochloric acid, lactic acid, malic acid, maleic acid, methanesulfonic acid, phosphoric acid, succinic acid, sulfuric acid, tartaric acid and toluenesulfonic acid. Particularly preferred are acids selected from the group consisting of hydrochloric acid, sulfuric acid and phosphoric acid, among which hydrochloric acid is most preferred.

More preferably the compounds of the formula (I) or (II) or (II') are converted into a pharmaceutically acceptable salt having a ratio of compound (I) or (II) or (II'): acid of from 1 to 2:1 to 3.

In principle, crystallization into the triple salt (3HCl) or into the mono-salt (1HCl) is possible. However, among these crystallization into the mono-salt is less preferred as further work-up steps of the compounds of formula (I) or (II) or (II') are required, including e.g. solvent exchange and several solvent extraction steps. This is less advantageous in view of the process economy. Thus, most preferred is the conversion into the triple HCl salt (3HCl salt).

In an alternative aspect of the present invention the process as described anywhere herein comprises the step of converting the compounds of the formula (I) or (II) or (II') into a sulfuric acid salt by adding sulfuric acid and crystallization of the sulfuric acid salt.

The conversion of the compounds of the formula (I) or (II) or (II') into hydrochloric salts provides an easy and efficient crystallization process, which allows direct crystallization of the decanted product phase without requiring phase separations. Chlorinated solvents may be disadvantageous for human and environmental safety. However, the preferred process step of converting the compounds of the formula (I)

or (II) or (II') into hydrochloric acid salts has potential for continuous processing which is also advantageous under the aspect of process efficiency.

Generally, the conversion of the compounds of the formula (I) or (II) or (II') into the salts can be carried out by conventional crystallization methods. Preferably the crystallization is carried out by cooling the reaction mixture comprising the reaction products with the compounds of the formula (I) or (II) or (II') to room temperature, adding a water-miscible solvent, such as preferably ethanol, and adding the selected acid for forming the respective acid salt. Preferably the crystallization is carried out by elevated temperature, preferably below the boiling point of the organic solvent and of water. The resulting crystallized salts are cooled below room temperature and isolated by usual methods, comprising e.g. filtration, washing and drying.

The formation of the salts of the compounds of the present invention can in particular be carried out by the methods described in the international application WO2018/192973.

As described therein, solvents used for crystallization comprise acetonitrile, dichloromethane (DCM), alcohols, such as especially methanol, ethanol, 2-propanol (iso-propanol), aldehydes, ketones, especially acetone, ethers, e.g. tetrahydrofuran (THF) or dioxane, esters, e.g. ethyl acetate, or alkanes, such as especially pentane, hexane, heptane or cyclohexane and water, and mixtures thereof. Preferred solvents used for crystallization are selected from the group consisting of acetonitrile, dichloromethane, methanol, ethanol, 2-propanol, ethyl acetate, THF, water and mixtures thereof.

Particularly preferred solvents used for crystallization are selected from the group consisting of acetonitrile, methanol, ethanol, 2-propanol, ethyl acetate, THF, water and mixtures thereof. Preferred water/solvent mixtures comprise mixtures of water and acetone, mixtures of water and ethanol and mixtures of water and methanol, wherein mixtures of water and ethanol and mixtures of water and methanol are preferred.

Particularly preferred are solvents used for crystallization, which are selected from the group consisting of acetonitrile, dichloromethane, ethanol, 2-propanol (iso-propanol), acetone and ethyl acetate as well as mixtures thereof with water, such as in particular mixtures of ethanol and water and mixtures of acetone and water. It is in particular preferred to use the solvents described in the Examples below.

Particularly preferred mixtures are the following mixtures of solvent and water (ratios of solvent mixtures given anywhere herein always refer to vol:vol):

acetone:water=9:1 (vol:vol)
acetone:water=95:1 (vol:vol)
ethanol:water=4:1 (vol:vol)
ethanol:water=3:1 (vol:vol)
ethanol:water=8:2 (vol:vol).

It is particularly preferred to carry out the conversion of the compounds (I) or (II) or (II') into the salts in a telescoped one-pot reaction together with the reaction step of reacting the intermediate compound IM-3 with a compound RM-3 to form the compound (I) or (II) or (II').

The salts of the compounds of the formula (I) or (II) or (II') may be present in amorphous, polymorphous, crystalline and/or semi-crystalline (partly crystalline) form as well as in the form of a solvate (or hydrate) of the salt. Preferably the salts of the present invention are present in crystalline and/or semi-crystalline (partly crystalline) form and/or in the form of solvates (hydrates) thereof.

The preferred crystallinity of the salts or salt solvates of the present invention can be determined by using conventional analytical methods, such as especially by using the various X-ray methods, which permit a clear and simple analysis of the salt compounds. In particular, the grade of crystallinity can be determined or confirmed by using Powder X-ray diffraction (reflection) methods as described for example in the Examples below, or by using Powder X-ray diffraction (transmission) methods as described for example in the Examples below (both being hereinafter also abbreviated as PXRD). For crystalline solids having identical chemical composition, the different resulting crystal gratings are summarized by the term polymorphism.

Preferably the salts of the present invention exhibit a degree of crystallinity of more than 30%, more preferably more than 40%, yet more preferably more than 50% such as at least 55-60%, measured with a PXRD method as described herein.

The salts of the present invention may be present as solvates and/or hydrates, which may be formed by attraction, association, adsorption, adhesion, embedding or complexation of molecules of a solvent in the crystal grating of the salts of the present invention. The solvent molecules which may be embedded in the crystal grating may derive from the solvents used for crystallization as well as from water deriving from the relative humidity.

The extent to which a selected solvent or water leads to a solvate or hydrate in the process steps or during the crystallization step depends on the combination of process conditions and the various interactions between the selected compound (I) or (II) or (II'), the counter anion from the selected acid and the selected solvent and humidity conditions. The salt solvates or hydrates may be preferred, as solvent or water molecules in the crystal structure are bound by strong intermolecular forces and thereby may represent an element of structure formation of these crystals which, in part, may improve stability of the salt. However, solvent and/or water molecules are also existing in certain crystal lattices which are bound by rather weak intermolecular forces. Such molecules are more or less integrated in the crystal structure forming, but to a lower energetic effect. The solvent and/or water content of the solvates is also dependent on the drying and ambient conditions (i.e. relative humidity). In the case of stable solvates or hydrates, there are usually clear stoichiometric ratios between the active compound (i.e. the salt) and the solvent or water. In many cases these ratios do not fulfil completely the stoichiometric value, normally it is approached by lower values compared to theory because of certain crystal defects. The ratio of organic molecules to solvent or water molecules for the weaker bound water may vary to a considerable extend, for example, extending over di-, tri- or tetra-hydrates. On the other hand, in amorphous solids, the molecular structure classification of solvent and/or water is not stoichiometric; the classification may however also be stoichiometric only by chance. In some cases, it is not possible to classify the exact stoichiometry of the solvent or water molecules, since layer structures form so that the embedded solvent or water molecules cannot be determined in defined form.

The solvent and/or water content in amorphous solids as well as in crystalline solvates or hydrates can, in general, be determined by conventional methods, such as e.g. by using the well-known Karl-Fischer titration method, by carrying out dynamic vapor sorption (DVS) measurements, by carrying out thermogravimetric measurements (TG-FTIR), as described for example in the Examples below. Also elemental analysis or methods for structural analysis, such as $^{1}H$ NMR spectroscopy or Raman spectroscopy (FT Raman spectroscopy) may give information about the degree of solvate or hydrate formation and/or may be used to confirm or validate the results of the Karl-Fischer (KF), DVS or TG-FTIR measurements.

Examples of solvates and/or hydrates according to the present invention comprise for example, hemi-(0.5), mono-, sesqui-(1.5), di-, tri-, tetra-, penta-, hexa-, hepta-, octa-, nona-deca-, etc. solvates or hydrates, respectively. Further intermediate solvation-degrees are also possible, such as solvation with 2.5, 3.5, 4.5 etc. solvent and/or water molecules.

Preferred examples of solvates and/or hydrates comprise solvates/hydrates with about 0.5, 1, 1.5, 2.5, 3, 4 and 7 solvate/water molecules. Further preferred examples of solvates and/or hydrates comprise solvates/hydrates with about 0.5, 1, 1.5, 2.5, 3, 4, 6 and 7 solvate/water molecules. More preferred are hemi- and mono-solvates/hydrates with about 0.5 or 1 solvate/water molecules, wherein hemi- and mono-hydrates are particularly preferred. Anhydrous salts are also preferred. It is further possible, that solvent and/or water residues remain in the salt in non-stoichiometric amounts.

Further, it is possible that mixtures of water and solvent remain in the salt forming so-called mixed hydrate/solvate forms. Examples of such mixed hydrate/solvate forms comprise in particular acetone/water, preferably with a ratio of 1 to 4:1; such as in particular 4:1; methanol/water, preferably with a ratio of 3 to 9:1; such as in particular 3:1, 4:1 and 9:1; ethanol/water, preferably with a ratio of 1 to 4:1; such as in particular 3:1 and 4:1.

Any reference hereinbefore and hereinafter, to the salts of the compounds of the formula (I) or (II) or (II') is to be understood as referring also to the corresponding solvates, such as hydrates, solvates and mixed hydrate/solvate forms, and polymorphous modifications, and also amorphous forms, as appropriate and expedient.

The new process of the present invention further surprisingly leads to increased yields compared to the processes as known from the prior art.

Yields in the range of ≥30%, preferably ≥35%, more preferably ≥40, even more preferred of ≥45% are now possible.

In contrast, the prior art processes provided yields of not more than 22%. For Example, the preparation of a 3HCl salt of compound (II) or (II') according to the process of the present invention can provide yields >60% as shown in Example 4 below. In contrast the preparation of said 3HCl with the process as described in WO2017/068089 and in WO2017/068090 provides a yield of only 22% as shown in the examples for preparing Example Compound No. 127.

In particular the new telescoped process steps of the present invention further provide a more feasible, cost and effort effective process. The formation of polymers in the intermediate formation steps can be avoided, which positively influences the process control and the yields.

A further aspect of the present invention relates to the compounds of the formula (I) or (II) or (II') as described anywhere herein, including the salts, hydrates, solvates and mixed hydrate/solvate forms, polymorphous modifications, and amorphous forms obtainable by the process as described herein. The compounds obtainable by the new process described herein are characterized by an improved and/or high(er) purity defined by their total impurity content of less than 2.00% rel. area, preferably less than 1.50 rel. area, more preferably less than 1.00% rel. area, wherein the impurities content is determined by HPLC as described in the Examples below and "% rel. area" indicates the sum of the relative area of all impurities in the HPLC spectrum.

Thus, a further aspect of the invention relates to the compounds of the formula (I) and (II) or (II') as described anywhere herein, including the salts, hydrates, solvates and mixed hydrate/solvate forms, polymorphous modifications, and amorphous forms, having a total purity of at least 97.80% rel. area, preferably at least 97.90% rel. area, at least 98.00% rel. area, at least 98.10% rel. area, at least 98.20% rel. area, at least 98.30% rel. area, at least 98.40% rel. area, at least 98.50% rel. area, at least 98.60% rel. area, at least 98.70% rel. area, at least 98.80% rel. area, at least 98.90% rel. area, at least 99.00% rel. area, at least 99.10% rel. area, at least 99.20% rel. area, at least 99.30% rel. area, at least 99.40% rel. area, at least 99.50% rel. area, at least 99.60% rel. area, at least 99.70% rel. area, at least 99.80% rel. area, at least 99.90% rel. area, at least 99.95% rel. area, at least 99.96% rel. area, at least 99.97% rel. area, at least 99.98% rel. area, at least 99.99% rel. area, wherein the purity is determined by HPLC as described in the Examples below and "% rel. area" indicates the relative area of the compound of the invention in the HPLC spectrum.

In particular, the compounds of the formula (I) and (II) or (II') as described anywhere herein, including the salts, hydrates, solvates and mixed hydrate/solvate forms, polymorphous modifications, and amorphous forms, are characterized by containing one or more of the impurities at relative retention times RRT 0.59, 0.65, 0.83, and 1.37 in an amount of not more than 0.20% rel. area, preferably not more than 0.15% rel. area, more preferably not more than 0.10% rel. area, preferably with a lower limit of 0.05% rel. area.

More preferably the compounds of the formula (I) and (II) or (II') as described anywhere herein, including the salts, hydrates, solvates and mixed hydrate/solvate forms, polymorphous modifications, and amorphous forms, are characterized by absence of the following impurities at relative retention times RRT: 0.59, 0.65, 0.83, and 1.37.

More particularly, the compounds of the formula (I) and (II) or (II') as described anywhere herein, including the salts, hydrates, solvates and mixed hydrate/solvate forms, polymorphous modifications, and amorphous forms, are characterized by absence of the following impurities at relative retention times: RRT 0.27, 0.52, 0.59, 0.65, 0.83, 0.94, 1.19, 1.37, preferably with a lower limit of 0.05% rel. area.

More particularly, the compounds of the formula (I) and (II) or (II') as described anywhere herein, including the salts, hydrates, solvates and mixed hydrate/solvate forms, polymorphous modifications, and amorphous forms, are characterized by an impurity profile comprising one or more of the impurities at relative retention times: RRT 0.48, 0.70, 1.27, and 1.48.

Therein, the impurities and their retention times RRT are determined by HPLC as described in the Examples below.

In contrast, with the process for preparing the Compound (II) in the form of the 3HCl salt as described in WO2017/068089 and in WO2017/068090 (preparation of Example Compound No. 127) it is not possible to achieve such high purity degree and improved impurity profile as can be seen from FIGS. 6, 7 and 8.

A particularly preferred embodiment of the present invention relates to a polymorph (PM1) of the triple HCl salt of the compound (II), which is characterized by a powder X-ray diffraction pattern (PXRD pattern) comprising characteristic crystalline peaks (main peaks) expressed in degrees 2-theta at about 3.9 and 16.5±0.25 degrees, or ±0.20 degrees or ±0.10 degrees or ±0.05 degrees.

Preferably in such embodiment of a polymorph (PM1) of the triple HCl salt of compound (II) the PXRD pattern comprises one or more further characteristic (main) peaks expressed in degrees 2-theta at about 7.9, 24.1, 19.1, 12.1, and/or 10.0±0.25 degrees or ±0.20 degrees or ±0.10 degrees or ±0.05 degrees.

More preferably in such embodiment of a polymorph the PXRD pattern comprises characteristic crystalline (main) peaks expressed in degrees 2-theta at 3.9, 16.5, 7.9, 24.1, 19.1, 12.1, and 10.0±0.20 degrees or ±0.10 degrees or ±0.05 degrees.

Preferably said polymorphs (PM1) of the triple HCl salt of compound (II) are present in the form of a hemihydrate. Preferably said polymorphs (PM1) of the triple HCl salt of compound (II) are characterized by water activities≤0.5%, preferably ≤0.4%, more preferred≤0.3%.

The melting point of said polymorphs (PM1) of the triple HCl salt of compound (II), determined via DSC as described in the Examples below, is preferably in a range of ≥180° C. and ≤220° C., preferably in a range of ≥185° C. and ≤215° C., more preferably in a range of ≥190 and ≤210° C.

More preferably, said polymorphs (PM1) of the triple HCl salt of compound (II) exhibit a microscopic crystallinity, determined via light microscopy using polarized light, characterized by spherical polycrystalline particles with low crystallinity. The average particle size, determined via light microscopy using polarized light, is about 10 to 50 μm.

The polymorphs (PM1) of the triple HCl salt of compound (II) are further characterized by high flow properties being present in the form of a flowing powder with low electrostatics.

Said polymorphs (PM1) of the triple HCl salt of compound (II) are further thermodynamically stable polymorphs at room temperature (23° C.±5° C.).

A further preferred embodiment of the present invention relates to a polymorph (PM2) of the triple HCl salt of the compound (II), which is characterized by a powder X-ray diffraction pattern (PXRD pattern) comprising characteristic crystalline (main) peaks expressed in degrees 2-theta at about 16.9 and 25.3±0.25 degrees, or ±0.20 degrees or ±0.10 degrees or ±0.05 degrees.

Preferably in such embodiment of a polymorph (PM2) of the triple HCl salt of compound (II) the PXRD pattern comprises one or more further characteristic (main) peaks expressed in degrees 2-theta at about 11.7, 28.3, 25.5, 20.1 and/or 26.2±0.25 degrees or ±0.20 degrees or ±0.10 degrees or ±0.05 degrees.

More preferably in such embodiment of a polymorph (PM2) of the triple HCl salt of compound (II) the PXRD pattern comprises characteristic crystalline (main) peaks expressed in degrees 2-theta at 16.9, 25.3, 11.7, 28.3, 25.5, 20.1 and 26.2±0.20 degrees or ±0.10 degrees or ±0.05 degrees.

Preferably said polymorphs (PM2) of the triple HCl salt of compound (II) are present in anhydrous form. Preferably said polymorphs (PM2) of the triple HCl salt of compound (II) are characterized by water activities≤0.8%, preferably ≤0.7%, more preferred≤0.6%.

The melting point of said polymorphs (PM2) of the triple HCl salt of compound (II), determined via DSC as described in the Examples below, is preferably in a range of ≥210° C. and ≤240° C., preferably in a range of ≥215° C. and ≤235° C., more preferably in a range of ≥220° C. and ≤230° C.

More preferably, said polymorphs (PM2) of the triple HCl salt of compound (II) exhibit a microscopic crystallinity, determined via light microscopy using polarized light, characterized by fine aggregated needles with high crystallinity.

The polymorphs (PM2) of the triple HCl salt of compound (II) are further characterized by having wool-type solid state properties.

Said polymorphs (PM2) of the triple HCl salt of compound (II) are thermodynamically less stable than the polymorphs PM1 or PM3 at room temperature (23° C.±5° C.).

A further preferred embodiment of the present invention relates to a polymorph (PM3) of the triple HCl salt of the compound (II), which is characterized by a powder X-ray diffraction pattern (PXRD pattern) comprising characteristic crystalline (main) peaks expressed in degrees 2-theta at about 14.7 and 10.3±0.25 degrees, or ±0.20 degrees or ±0.10 degrees or ±0.05 degrees.

Preferably in such embodiment of a polymorph (PM3) of the triple HCl salt of compound (II) the PXRD pattern comprises one or more further characteristic (main) peaks expressed in degrees 2-theta at about 17.0, 26.5, 18.1, 22.1 and/or 27.1±0.25 degrees or ±0.20 degrees or ±0.10 degrees or ±0.05 degrees.

More preferably in such embodiment of a polymorph (PM3) of the triple HCl salt of compound (II) the PXRD pattern comprises characteristic crystalline (main) peaks expressed in degrees 2-theta at 14.7, 10.3, 17.0, 26.5, 18.1, 22.1 and 27.1±0.20 degrees or ±0.10 degrees or ±0.05 degrees.

Preferably said polymorphs (PM3) of the triple HCl salt of compound (II) are present in the form of a monohydrate. Preferably said polymorphs (PM3) of the triple HCl salt of compound (II) are characterized by water activities >0.3%.

The melting point of said polymorphs (PM3) of the triple HCl salt of compound (II), determined via DSC as described in the Examples below, is preferably in a range of ≥150° C. and ≤190° C., preferably in a range of ≥155° C. and ≤180° C., more preferably in a range of ≥160 and ≤175° C.

More preferably, said polymorphs (PM3) of the triple HCl salt of compound (II) exhibit a microscopic crystallinity, determined via light microscopy using polarized light, characterized by fine rods with high crystallinity.

The polymorphs (PM3) of the triple HCl salt of compound (II) are further characterized by having voluminous, non-flowing powder properties.

Said polymorphs (PM3) of the triple HCl salt of compound (II) are thermodynamically stable at room temperature (23° C.±5° C.).

Among the above-described polymorphs of the triple salt of compound (II) PM1 is most preferred, in particular because of its thermodynamic stability at room temperature, the spherical particle form and its good flow properties with low electrostatics, which is advantageous for using said polymorphs as a pharmaceutical active ingredient.

In the above-described embodiments, the term "characteristic peak(s)" or "main peak(s)" represents those peak(s) in the PXRD pattern with the highest intensity. The intensity of the peaks in the PXRD patterns decreases in the order of the peaks listed above and the polymorphs (PM1, PM2 and PM3) are preferably characterized by having two or more of those characterizing (main) peaks with the highest intensity.

The compounds (II') described above have not been disclosed in the prior art, such as in WO2017/068089, in WO2017/068090, in WO2018/192973 or in WO2011/029832 and are novel compounds per se.

The compounds of the formula (I) and (II) and (II') as described herein are in particular suitable for the use as a medicament, which act as ferroportin inhibitors. Therein, ferroportin inhibition can be determined as described in any of the international patent applications WO2018/192973, WO2017/068089 and WO2017/068090.

The compounds of the formula (I) and (II) and (II') as described herein, including the preferred salts and polymorphs thereof, are in particular suitable for the use in the prophylaxis and/or treatment of iron metabolism disorders leading to increased iron levels or increased iron absorption, such as for the use in the prophylaxis and/or treatment of iron overload and/or for the use in the prophylaxis and/or treatment of diseases related to or caused by increased iron levels, increased iron absorption or iron overload. Therein, the diseases, which are related to or caused by increased iron levels, increased iron absorption or iron overload include e.g. thalassemia, hemoglobinopathy, hemoglobin E disease, hemoglobin H disease, haemochromatosis, hemolytic anemia, thalassemia, including alpha-thalassemia, beta-thalassemia and delta-thalassemia, sickle cell anemia (sickle cell disease) and congenital dyserythropoietic anemia.

The compounds of the formula (I) and (II) and (II') as described herein, including the preferred salts and polymorphs thereof, are further suitable for the use in the prophylaxis and/or treatment of diseases associated with ineffective erythropoiesis, such as myelodysplastic syndromes (MDS, myelodysplasia), polycythemia vera and congenital dyserythropoietic anemia, or for the use in an adjunctive therapy by limiting the amount of iron available to pathogenic microorganisms, such as the bacterium *Vibrio vulnificus*, thereby treating infections caused by said pathogenic microorganisms, or for the use in the prophylaxis and/or treatment of neurodegenerative diseases such as Alzheimer's disease and Parkinson's disease by limiting the deposition or increase of iron in tissue or cells, or for the use in the prophylaxis and/or treatment of formation of radicals, reactive oxygen species (ROS) and oxidative stress, or for the use in the prophylaxis and/or treatment of cardiac, liver and endocrine damage caused by iron overload, or for the use in the prophylaxis and/or treatment of inflammation triggered by excess iron.

Accordingly, the invention further relates to a medicament containing one or more of the compounds (I) or (II) or (II'), including its salts, hydrates, solvates and mixed hydrate/solvate forms, polymorphous modifications, and amorphous forms, as defined herein, such as a medicament for the use in the prophylaxis or treatment in any of the diseases, conditions or symptoms as described above. Such medicament may optionally further contain one or more pharmaceutical carriers and/or auxiliaries and/or solvents, and/or at least one additional pharmaceutically active compound, such as an active compound for the prophylaxis and treatment of iron overload, thalassemia, haemochromatosis or sickle cell disease, of neurodegenerative diseases, such as Alzheimer's disease or Parkinson's disease, and the associated symptoms, or an iron-chelating compound.

The medicament as described above may be in the form of a formulation for oral or parenteral administration.

The compounds (I) or (II) or (II'), including its salts, hydrates, solvates and mixed hydrate/solvate forms, polymorphous modifications, and amorphous forms, as defined herein, are further suitable for the use in a combination therapy, comprising co-administration of the compounds of the invention together with at least one additional pharmaceutically active compound, wherein the co-administration of the combination therapy may be carried out in a fixed dose combination therapy by co-administration of the compounds of the invention with at least one additional pharmaceutically active compound in a fixed-dose formulation or wherein the co-administration of the combination therapy may be carried out in a free dose combination therapy by co-administration of the compounds of the invention and the at least one additional pharmaceutically active compound in free doses of the respective components, either by simultaneous administration of the individual components or by sequential use of the individual components distributed over a time period, and wherein the combination therapy preferably comprises co-administration of the compounds of the invention with one or more other pharmaceutically active compounds for reducing iron overload, which are selected from Tmprss6-ASO, iron chelators, curcumin, SSP-004184, Deferitrin, deferasirox, deferoxamine and/or deferiprone and/or with one or more other pharmaceutically active compounds which are selected from antioxidants, such as n-acetyl cysteine; anti-diabetics, such as GLP-1 receptor agonists; antibiotics, such as vancomycin (Van) or tobramycin; drugs for the treatment of malaria; anticancer agents; antifungal drugs; drugs for the treatment of neurodegenerative diseases such as Alzheimer's disease and Parkinson's disease, comprising dopamine agonists such as Levodopa; anti-viral drugs, such as interferon-α or ribavirin; immunosuppressants, such as cyclosporine A or cyclosporine A derivatives; iron supplements; vitamin supplements; red cell production stimulators (e.g. erythropoietin, Epo); anti-inflammatory biologics; anti-thrombolytics; statins; vasopressors; and inotropic compounds.

A further aspect of the present invention relates to the novel intermediate compounds, which can be prepared with the novel process steps of the present invention and to the respective process for preparing them. The process steps for preparing the intermediate compounds may further comprise a crystallization, isolation and/or purification step for isolating intermediate compounds.

Specifically, the present invention relates to intermediate compounds of the general formula (IM-2-a)

(IM-2-a)

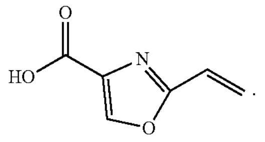

A further aspect of the present invention relates to a process for preparing said intermediate compound (IM-2-a), comprising the reaction steps as defined anywhere above in context with the description of the preparation of the compounds of the formula (I), such as in particular by the following process:

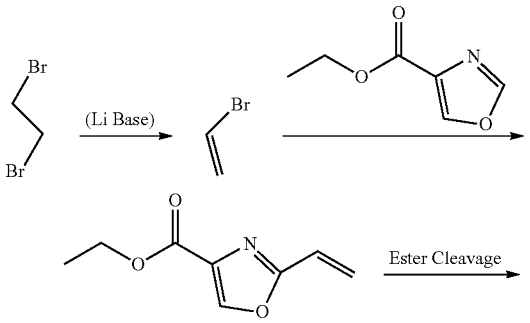

-continued

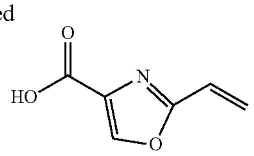

(IM-2-a)

(IM-2-a)
which may further comprise a crystallization, isolation and/or purification step for isolating intermediate compound (IM-1). Therein, the preferred process conditions, bases, solvents and catalysts as described above are preferably used for the preparation and for the crystallization and isolation.

In a further aspect, the present invention relates to intermediate compounds of the general formula (IM-3)

(IM-3)

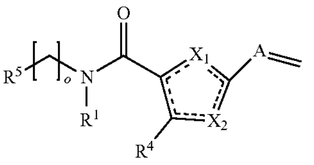

wherein $X^1$, $X^2$, $R^1$, $R^4$, $R^5$, A and o have the meaning as defined anywhere herein.

Preferably, said intermediate compounds (IM-3) are characterized by having a group $R^5$ which is represented by the formula

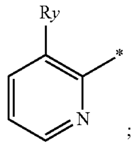

;

and wherein further, o is 1;

$R^1$ is hydrogen;

A represents a CH-group;

and which is represented by the following formula (IM-3-a)

(IM-3-a)

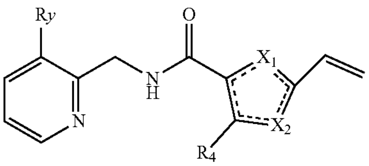

, wherein $X^1$, $X^2$, $R^4$ and $R_y$ have the meaning as defined anywhere herein.

More preferably, said intermediate compounds (IM-3) are characterized in that $X^1$ represents N;

$X^2$ represents O;

A represents a CH-group;

o represents 1;

$R^4$ represents hydrogen; and $R_y$ represents fluorine or bromine (with fluorine being preferred);

and which is represented by the following formula (IM-3-b) or (IM-3-b'):

(IM-3-b)

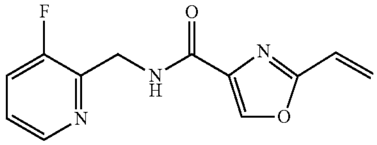

(IM-3-b')

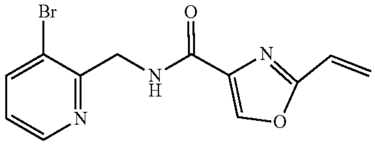

A further aspect of the present invention relates to a process for preparing the intermediate compounds (IM-3), (IM-3-a) or (IM-3-b) or (IM-3-b') as defined above, comprising the reaction steps as defined anywhere above in context with the description of the preparation of the compounds of the formula (I). Therein, the preferred process conditions, bases, solvents and catalysts as described above are preferably used for the preparation and for the crystallization and isolation.

A further aspect of the present invention relates to a new process for preparing the intermediate compound (IM-1) or (IM-1-a) as defined anywhere above, said process comprising the reaction step as described above in the fourth aspect of the present invention or in a process according to the process step 1-a' and more preferred process step 1-a'', both as described above. Therein, the preferred process conditions, bases, solvents and catalysts as described above are preferably used for the preparation and for the crystallization and isolation.

The present invention is illustrated in more detail by the following examples. The examples are merely explanatory, and the person skilled in the art can extend the specific examples to further suitable variants being covered hereunder.

EXAMPLES

Abbreviations

Figure 1:
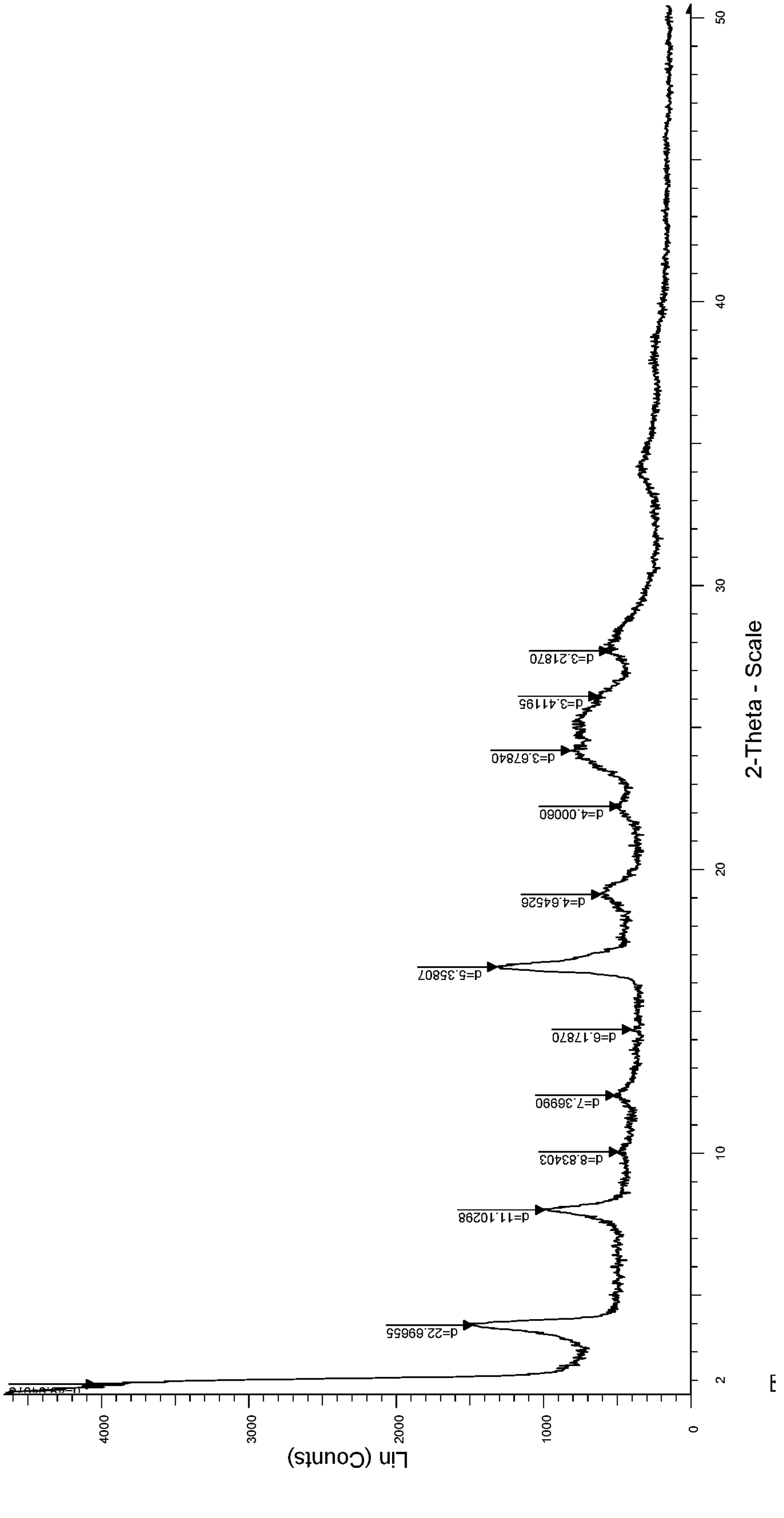
FIG. 1: PXRD pattern of Compound (II) in the form of the 3HCl salt (polymorph PM1)

DCM dichloromethane
DSC differential scanning calorimetry
IPC Ion Pair Chromatography
HPLC High Pressure Liquid Chromatography
PXRD Powder X-ray diffraction
THF Tetrahydrofuran
Mw Molecular Weight

1a. Process for Preparing an Intermediate Compound (IM-2-a) with Crystallization from HCl Chemicals:

| Chemical | Molar Mass g/mol | Molar Mass mmol | Eq. | Amount (th) | Amount (is) |
|---|---|---|---|---|---|
| 1,2-dibromoethane | 187.86 | 120.5 | 1.7 | 22.63 g | |
| Li-tert-butoxide | 80.06 | 198.4 | 2.8 | 15.88 g | |
| THF | — | — | — | 70 ml<br>15 ml<br>15 ml | |
| ethyl 4-oxazolcarboxylate | 141.12 | 70.9 | 1.0 | 10.00 g | |
| $Pd(PPh_3)_4$ | — | — | — | 2.24 g | |
| Lithium hydroxide | 23.95 | 106.3 | 1.5 | 2.55 g | |
| water | — | — | — | 35 ml | |
| isopropyl acetate | — | — | — | 2x 70 ml | |
| hydrochloric acid 20% | — | — | — | x ml | x ml |

Reaction:

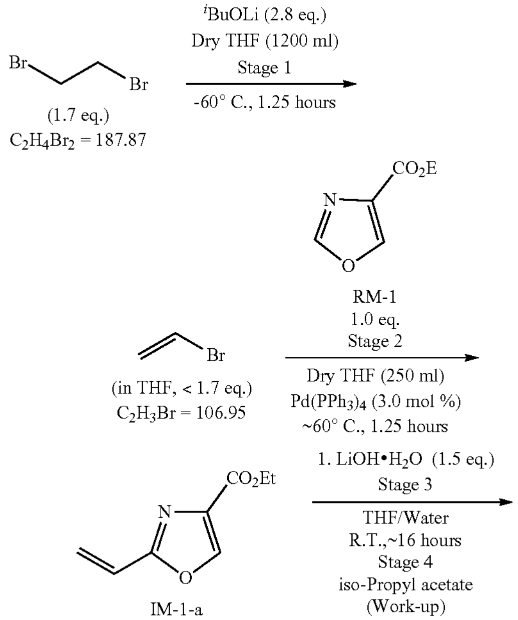

(1.7 eq.)
$C_2H_4Br_2$ = 187.87

RM-1

(in THF, < 1.7 eq.)
$C_2H_3Br$ = 106.95

IM-1-a
$C_8H_9NO_3$ = 167.16

-continued

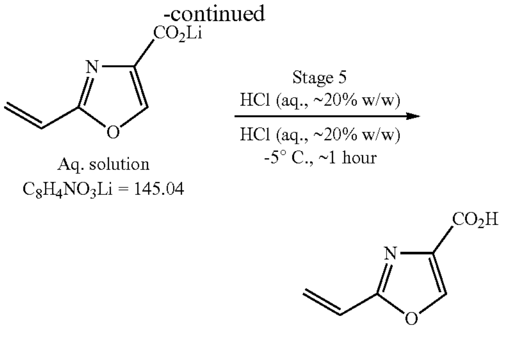

Aq. solution
$C_8H_4NO_3Li$ = 145.04

IM-2-a
$C_6H_5NO_3$ = 139.11

Procedure:

The vessel is purged with $N_2$ for ≥15 min.

LitOBu is charged, 70 ml THF are dosed and stirred for ≥10 min at 20-25° C.

The mixture is heated to 55-60° C. and stirred ≥5 min.

A solution of 1,2-dibromoethane in 15 ml THF is dosed at 55-60° C.

The mixture is stirred for ≥30 min at this temperature.

The mixture is cooled to 45-50° C.

$Pd(PPh_3)_4$ is added, purged with some ml THF and stirred at this temperature for ≥5 min.

The mixture is heated to 60-65° C. and a solution of ethyl 4-oxazolcarboxylate in 15 ml THF is dosed at 60-65° C. (exothermic).

The mixture is stirred at this temperature ≥30 min.

The mixture is cooled to 20-25° C.

A solution of LiOH in 35 ml water is dosed at 20-25° C. and stirred overnight (exotherm).

IPC via HPLC: ≥95% conversion

The mixture is extracted three times with isopropyl acetate. The organic phases are discarded.

The aqueous phase is cooled to 0-5° C. and the pH is measured.

The pH is adjusted with HCl 20% to 0.9-1.1 by keeping the temperature≤10° C.

The suspension is stirred at −5 to 0° C. for ≥45 min.

The suspension is filtered, washed with 50 ml cooled (≤5° C.) HCl of pH 0, 20 ml of cooled (≤5° C.) water and is dried in vacuo at 45° C. to dryness.

Yield:

| | Theory | Found | Comments |
|---|---|---|---|
| Yield Crude | — | | |
| Yield Final Product (pale brown solid) | 9.9 g | 6.5 g | 66% uncorr. |

HPLC = 98% area
q-NMR = 98% m/m

1b. Alternative Process Step for Preparing Intermediate Compound (IM-1-a)

In an alternative (but less preferred) process according to Example 1a above the process steps of stage 1 and stage 2 described therein can alternatively be carried out by starting with a compound RM-1 wherein $R_y$ is chlorine and $R^4$ is hydrogen and which is indicated herein as RM-1-a', leading to intermediate compound IM-1-a.

| | Molar Mass | | | |
|---|---|---|---|---|
| Chemical | g/mol | mmol | Eq. | Amount |
| ethyl 2-chlorooxazole-4-carboxylate | 175.57 | 885.69 | 1.0 | 155.50 g |
| tributyl(vinyl)tin | 317.1,1 | 877.96 | 1.0 | 278.40 g |
| $Pd(PH_3P)_2Cl_2$ | 701.9 | 43.60 | — | 30.60 g |
| dioxane | — | — | — | 1500 ml |

Reaction:

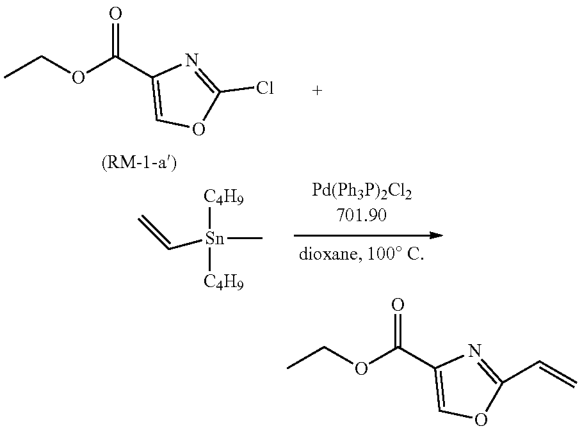

(RM-1-a')

(IM-1-a')

Procedure:

Ethyl 2-chlorooxazole-4-carboxylate, tributyl(vinyl)tin and $Pd(Ph_3P)_2Cl_2$ are charged in dioxane under nitrogen. The mixture is heated to reflux OT 100-110° C. for ≥4 h. The mixture is cooled to IT 20-25° C., filtrated over Celite and the filtercake washed with 200 ml of dioxane. The filtrate is evaporated in vacuo to dryness and the crude product purified by chromatography.

Column: Kp-Sil 1500 g

Eluent: EtOAc/Heptane 20:80

Method: Duration 7 CV, no gradient, threshold 20 mAU;

Crude dissolved in EtOAc/Heptane 20:80, two columns used at this scale

Yield:

| | Theory | Found | Comments |
|---|---|---|---|
| Yield Crude | — | 453.40 g | |
| Yield Final Product | 146.02 g | 112.34 g | 76.93% |

NMR conform to structure

1c. Alternative Process Step for Preparing Intermediate Compound (IM-1-a)

In a further alternative (preferred) process according to Example 1a above the process steps of stage 1 and stage 2 described therein can alternatively be carried out by starting with a compound RM-1 wherein $R_y$ is chlorine and $R^4$ is hydrogen and which is indicated herein as RM-1-a', leading to intermediate compound IM-1-a.

Reaction:

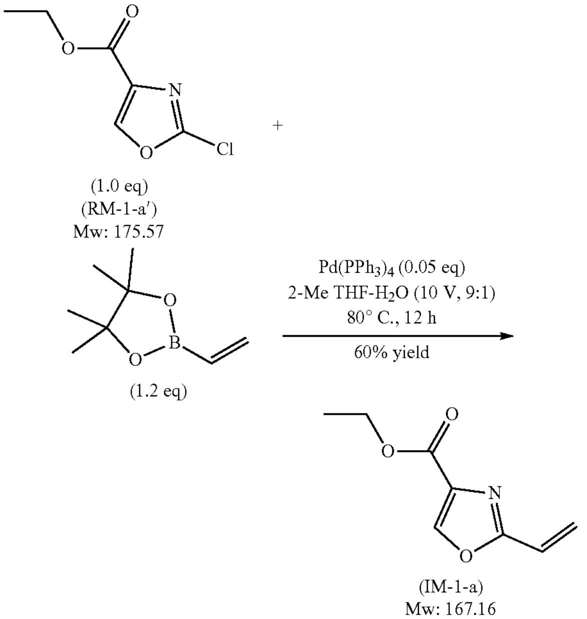

(1.0 eq)
(RM-1-a')
Mw: 175.57

(1.2 eq)

(IM-1-a)
Mw: 167.16

Procedure:

A RBF was charged with ethyl 2-chlorooxazole-4-carboxylate (RM-1-a'/1.0 eq), 2-Me THF (9 V) and water (1 V) were added under nitrogen atmosphere at 25-30° C. To this mixture vinylboronic acid pinacol ester (1.2 eq) and potassium carbonate (2.5 eq) were added at 25-30° C. and the resultant mixture was degassed with nitrogen for 15 minutes. $Pd(PPh_3)_4$ (0.05 eq) was added under a nitrogen atmosphere and the reaction mixture was warmed to 80° C. The reaction mixture was stirred for 8-12 h at 80-85° C. and reaction completion was monitored by TLC/HPLC. After completion of the reaction, the reaction mixture was cooled to 25-30° C. and diluted with water (5 V). The phases were separated and the aqueous phase was extracted with 2-Me THF (5 V). The combined organic phases were washed with water (5 V) followed by brine solution (5 V) and then dried over sodium sulfate. The organic phase was filtered and concentrated below 50° C. under vacuum to obtain the crude product as brown liquid. The crude product was purified using silica gel (60-120 mesh) column chromatography eluting with ethyl acetate and n-heptane to obtain the pure product.

NMR conform to structure.

Yield:

55-60%

Purity:

Purity of the obtained material was in the range of 96-99%.

By further purification using n-heptane crystallization at lower temperature below 0° C. a purity of >98% was obtained. When testing this highly purified material for Palladium content using ICP-MS, an amount in the range of 10-250 ppm was found, which was further reduced by treatment with a Siliabond thiol scavenger (heterogeneous Pd scavenger treatment) to a content below 25 ppm.

2. Process for Preparing an Intermediate Compound (IM-2-a) with Crystallization from Water Chemicals:

| | Molar Mass | | | | |
|---|---|---|---|---|---|
| Chemical | g/mol | mmol | Eq. | Mass th. | Mass is |
| IM-1-a | 167.16 | 598.2 | 1.0 | 100.00 g | 100.14 g |
| THF | — | — | — | 500 ml | 500 ml |
| water | — | — | — | 500 ml | 500 ml |
| lithium hydroxide | 23.95 | 658.1 | 1.1 | 15.76 g | 15.76 g |
| HCl 20% | — | — | — | x ml | x ml |
| DCM | — | — | — | 2 × 500 ml | 2 × 500 ml |
| magnesium sulfate | — | — | — | x g | x g |

Reaction:

The starting compound IM-1-a can be prepared according to process steps "stage 1" and "stage 2" of Example 1a or as described in Example 1b (less preferred).

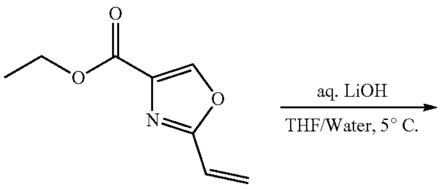

167.16
IM-1-a

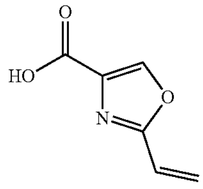

139.11
IM-2-a

Procedure:

IM-1-a is charged into the reactor and dissolved in THF.

The solution is cooled to 3-7° C.

A solution of LiOH (15.76 g in 500 ml water) is added ≥15 min (slightly exotherm) at 3-7° C.

The mixture is stirred ≥3 h at 3-7° C.

IPC via LC/MS ≥97% conversion.

The mixture is extracted twice with DCM. The DCM phase extractions and separations are done with the aq. phase at 5° C. but without active cooling using DCM having room temperature.

The phases are rested ≥30 min.

The organic layers are discarded.

The vessel is cleaned with HCl 20% and ethanol.

HCl 20% is dosed to the aq. phase at 3-7° C. till pH 0.5-1.0 (slightly exotherm, the HCl should not rinse at the vessel walls). Towards the end of HCl dosing during crystallization the stirrer speed is raised from 80 to 300 rpm for a good mixing of the suspension.

The suspension is stirred ≥30 min at 3-7° C.

The suspension is filtered and the reactor rinsed once with the mother liquor.

The wet cake is washed with water of 5-10° C. and dried at 45° C./vacuum <50 mbar to dryness.

The transfer of the fine suspension on the filter is leaving some residues in the vessel but these are easily removed by one rinse with the mother liquor.

Yield:

| | Theory | Found | Comments |
|---|---|---|---|
| Yield Crude | — | | |
| Final Yield | 83 g | 77 g | 93% uncorr. |

NMR Assay: 97% m/m
Corr. Yield: 90%

3a. Process for Preparing an Intermediate Compound (IM-3-b) with Crystallization from Water Chemicals:

| | Molar Mass | | | amount | amount |
|---|---|---|---|---|---|
| Chemical | g/mol | mmol | Eq. | th. | is |
| IM-2-a | 139.11 | 718.9 | 1.00 | 100.00 g | |
| DCM | — | — | — | 900 ml | |
| 4-methyl-morpholine | 101.15 | 2731.7 | 3.80 | 276.31 g | |
| ethyl-chloroformate | 108.52 | 898.6 | 1.25 | 97.51 g | |
| RM-2-a | 199.05 | 898.6 | 1.25 | 178.86 g | |
| NaCl-sol. 10% | — | — | — | 2 × 900 ml | |
| HCl 10% | | | | 3 × 450 ml | |

Reaction:

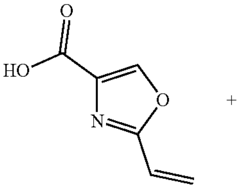

139.11
IM-2-a

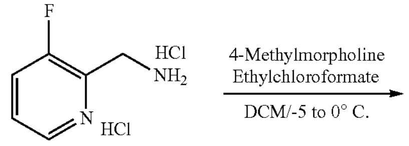

199.05
RM-2-a HCl salt

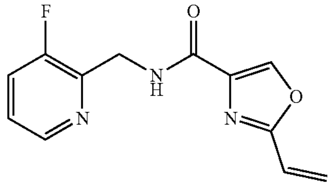

247.23
IM-3-b

Procedure:

The starting compound IM-2-a may be prepared as described in Example 1 or 2.

Under inert atmosphere compound IM-2-a is suspended in DCM and 4-methylmorpholine is added at −5 to 0° C.

Afterwards ethylchloroformate is added keeping the temperature≤0° C. (exothermic addition).

Compound RM-2-a (grinded) is added in portions keeping the temperature≤0° C.

The suspension is stirred ≥2 h at −5 to 0° C.

IPC control by LC/MS conversion ≥93% area.

The mixture is heated to 15-25° C. and extracted two times with NaCl 10% solution.

The organic phase is extracted three times with 450 ml HCl 10% w/w.

The combined aqueous phases are adjusted to pH 2 with 30% NaOH and afterwards to pH 7-8 with 5% NaOH keeping the temperature≤10° C.

The suspension is filtered, washed two times with 400 ml of water and dried in vacuum at 45° C. to dryness.

Yield:

| | Theory | Found | Comments |
|---|---|---|---|
| Yield Crude | — | | |
| Final Yield | 178 g | 162 g | 91% uncorr |

NMR assay: 99%
Corr. Yield: 90%

3b. Process for Preparing Intermediate Compound (IM-3-b)-Telescoped Synthesis Via IM-2-a Reaction:

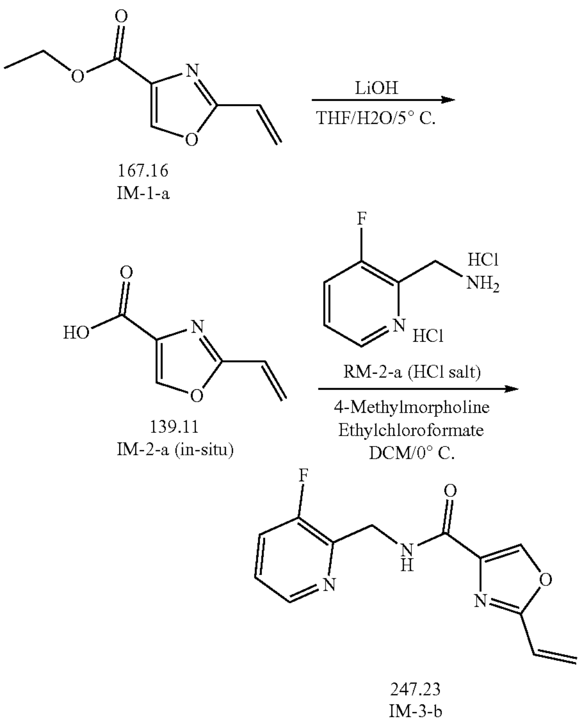

167.16
IM-1-a 139.11
IM-2-a (in-situ)

247.23
IM-3-b

Process Variant 1:

Chemicals:

| Chemical | Molar Mass g/mol | Molar Mass mmol | Eq. | Amount (th) | Amount (is) |
|---|---|---|---|---|---|
| IM-1-a | 167.16 | 59.8 | 1.0 | 10.00 g | |
| THF | — | — | — | 50 ml | |
| Water | — | — | — | 50 ml | |
| LiOH | 23.95 | 71.8 | 1.2 | 1.72 g | |
| DCM | — | — | — | 3 × 50 ml | 3× |
| HCl 20% | — | — | — | x ml | x ml |
| DCM | — | — | — | x ml | |
| 4-methyl-morpholine | 101.15 | 227.3 | 3.80 | 22.99 g | |
| ethyl-chloroformate | 108.52 | 74.8 | 1.25 | 8.11 g | |
| RM-2-a | 199.05 | 74.8 | 1.25 | 14.88 g | |
| NaCl 10% | — | — | — | 2 × 150 ml | |
| HCl 10% | | | | 3 × 75 ml | |

Procedure:

The starting compound IM-1-a may be prepared as described in Example 1 or 2.

The starting compound IM-1-a is dissolved in THF. A solution of 1.72 g LiOH in 20 ml water is added at IT 0-5° C. The mixture is stirred at 3-7° C. for ≥3 h.

IPC via HPLC-MS ≥97% conversion.

The mixture is adjusted to IT 15-20° C. and the pH set to 0.8-1.2 by addition of HCl 20% at this temperature range. The mixture is extracted three times with DCM. The combined organic phases are dried via azeotropic solvent removal by distilling off 50 ml of volume at OT 30° C./600 mbar and addition of 50 ml DCM afterwards. This procedure is repeated till water content is 0.13%, determined by Karl Fischer.

The solution is filled up to a volume of 160 ml with DCM and cooled to IT-5-0° C. 4-methylmorpholine is added in this temperature range. Ethylchloroformate is added at this temperature range (exothermic). RM-2-a (grinded) is added in portions at IT≤0° C. The mixture is stirred at −5-0° C. for ≥3 h.

IPC via HPLC-MS≥93% conversion.

The mixture is extracted two times with NaCl 10% solution. The water phases are discarded.

The organic phase is extracted three times with 75 ml of HCl 10%. The organic phase is discarded. The combined water phases are adjusted at IT≤10° C. to pH 2 with NaOH 30% first and afterwards with NaOH 5% to pH 7-8. After stirring ≥15 min at ≤10° C. the suspension is filtered and washed two times with 60 ml water. The filter cake is dried at OT 45° C./<100 mbar to dryness.

Yield:

| | Theory | Found | Comments |
|---|---|---|---|
| Yield Crude | — | | |
| Final Yield off-white powder | 14.78 g | 10.35 g | 70.03% |

HPLC Purity = 99.8%
Water = 0.04%

In experiments with a DCM water content of 0.04% by azeotroping the yield was even up to 85%.

Process Variant 2:
Chemicals:

| Chemical | Molar Mass g/mol | Molar Mass mmol | Eq. | Amount (th) |
|---|---|---|---|---|
| IM-1-a | 167.16 | 2392.9 | 1.00 | 400.00 g |
| THF | — | — | 5.00 | 2000.0 ml |
| aq. LiOH 34.4 g/l | 23.95 | 2871.5 | 1.2 | 1999.8 ml |
| HCl 20% | — | — | — | x ml |
| DCM | — | — | 3 x 5.0 | 3 x 2000.0 ml |
| | | | 2.0 | 800.0 ml |
| | | | 2.0 | 800.0 ml |
| | | | 3 x 10.0 | 3 x 4000.0 ml |
| DMF | — | — | 7.0 | 2800.0 ml |
| | | | 1.5 | 600.0 ml |
| 4-methylmorpholine | 101.15 | 9332.4 | 3.90 | 943.97 g |
| ethylchloroformate | 108.52 | 3230.4 | 1.35 | 350.57 g |
| RM-2-a | 199.05 | 2991.1 | 1.25 | 595.39 g |
| Water | — | — | 11.0 | 4400.0 ml |
| | | | 2.5 | 1000.0 ml |
| | | | 2.5 | 1000.0 ml |

Procedure:

The starting compound IM-1-a may be prepared as described in Example 1 or 2.

The starting compound IM-1-a is charged in a reactor and filled with THF. The solution is cooled to 0-5° C. and a LiOH solution is dosed at IT≤5° C. The solution is stirred at IT 0-5° C. ≥60 min.

IPC via HPLC:

If IPC IM-1-a is <0.2% a/a, the pH is adjusted to pH 0.5-1.0 at 15-20° C. with HCl 20%.

The mixture is extracted 3× with DCM. The combined organic phases are dried over $MgSO_4$, filtrated and the filter cake washed with DCM. DCM is evaporated at OT 32-37° C./400 mbar. 8.5 eq. of DMF are added. THF is evaporated at 32-37° C./to 35 mbar. (End points of distillation when no further solvent is condensing.)

IPC via KF≤0.2% water:

If IPC is out of spec, 10 eq. of DCM are added and distilled off at 32-37° C. again followed by IPC KF.

4-Methylmorpholine is added to the DMF solution at IT-5 to 0° C. Ethylchloroformate is added at IT=−5° C. to 0° C. RM-2-a (milled) is added at IT −5° C. to 0° C. The mixture is stirred for ≥5 h at IT −5 to 0° C.

IPC via HPLC:

If IPC IM-3-a>85% a/a, water is added slowly at IT<10° C. The pH of the reaction mixture is adjusted to pH 6-8 with NaOH 30% if necessary. The product suspension is stirred ≥60 min at IT 0-5° C., filtered, washed twice with water and dried at 45° C. in vacuo.

Yield:

Yield=448.42 g=75.6%

HPLC Assay=98.2%

HPLC Purity=99.7%

3c. Process for Preparing Intermediate Compound (IM-3-b)-Telescoped Synthesis Via IM-2-a Reaction:

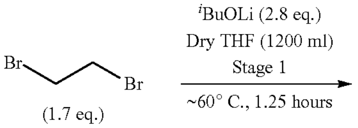

(1.7 eq.)
$C_2H_4Br_2$ = 187.87

-continued

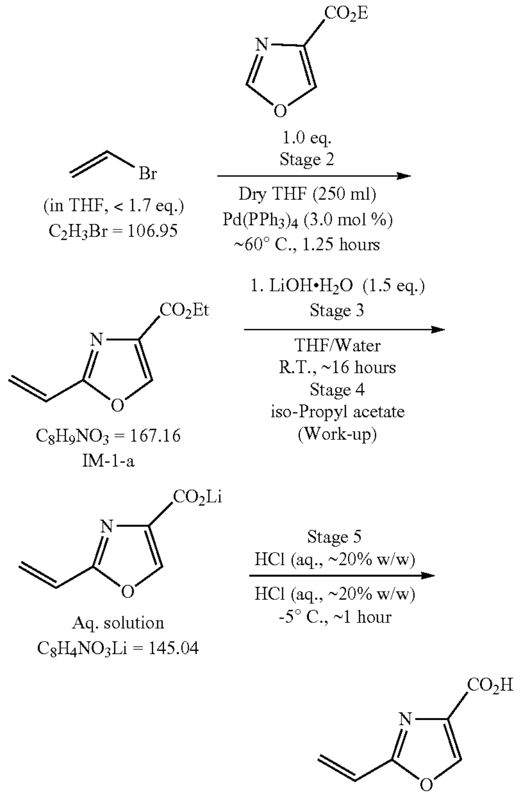

$C_6H_5NO_3$ = 139.11
IM-2-a

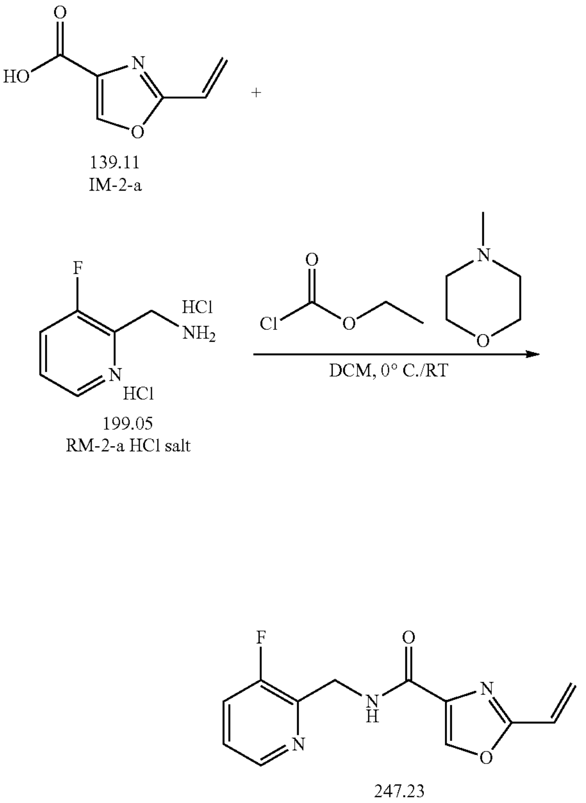

139.11
IM-2-a 199.05
RM-2-a HCl salt 247.23
IM-3-b

Process Variant 1:

Chemicals:

| Chemical | Molar Mass g/mol | mmol | Eq. | Amount (th) | Amount (is) |
|---|---|---|---|---|---|
| 1,2-dibromoethane | 187.86 | 120.5 | 1.70 | 22.63 g | |
| lithium tert-butoxid | 80.06 | 198.4 | 2.80 | 15.88 g | |
| THF | — | — | — | 70 ml | |
| | | | | 15 ml | |
| | | | | 15 ml | |
| ethyl 4-oxazol-carboxylate | 141.12 | 70.9 | 1.00 | 10.00 g | |
| $Pd(PPh_3)_4$ | — | — | 2.7% | 2.24 g | |
| LiOH | 23.95 | 106.3 | 1.50 | 2.55 g | |
| MTBE | — | — | — | 2 × 70 ml | |
| HCl 20% | — | — | — | x ml | x ml |
| THF | — | — | — | 50 ml | |
| dichlormethane | — | — | — | 3 × 50 ml | 3× |
| 4-methyl-morpholine | 101.15 | 269.3 | 3.80 | 27.24 g | |
| ethyl-chloroformate | 108.52 | 88.6 | 1.25 | 9.61 g | |
| RM-2-a | 199.05 | 88.6 | 1.25 | 17.63 g | |
| NaCl soln. 10% | — | — | — | 2 × 100 ml | 2× |

Procedure:

The vessel is purged ≥15 min with $N_2$. LitOBu is charged to the vessel, 70 ml THF are added and the mixture is stirred at IT 20-25° C. for ≥10 min.

The mixture is heated up to IT 53-57° C. and stirred for ≥5 min.

A solution of 1,2-dibromoethane in 15 ml THF is added at IT 55-60° C. (exothermic), the mixture is stirred for ≥30 min at IT 58-62° C.

The mixture is cooled to IT 43-47° C.

$Pd(PPh_3)_4$ is added and stirred for ≥5 min.

The mixture is heated to IT 58-62° C., a solution of (ethyl 4-oxazolcarboxylate in 15 ml THF is added at IT 60-65° C.

The mixture is stirred for ≥30 min at IT 58-62° C.

IPC Via HPLC for Information:

no Ethyl 4-oxazolcarboxylate ethylester product 72% tert-butylester product 23%

Intermediate product IM-1-a 5%

The mixture is cooled to IT 20-25° C.

A solution of LiOH in 35 ml water is added at IT 20-27° C. and the mixture is stirred at IT 23-27° C. for ≥16 h.

IPC via HPLC ≥93%

35 ml water are added and the mixture extracted two times with 70 ml TBME.

50 ml THF are added and the pH is adjusted at IT 15-20° C. to 0.5-1.0 with HCl 20%.

The mixture is extracted three times with 50 ml of DCM

The combined organic phases are dried over $Na_2SO_4$ (15-20 g), filtered and the filter cake washed with 10 ml DCM.

DCM phase=0.51% water via Karl Fischer.

OT is set to −20° C.

4-Methylmorpholine is added at IT-5 to 0° C.

Ethylchloroformate is added at IT-5 to 0° C.

RM-2-a (grinded) is added in portions at IT≤0° C. and the mixture is stirred at IT-5 to 0° C. for ≥3 h.

IPC via HPLC ≥90%.

The mixture is extracted two times with 100 ml NaCl 10%.

The intermediate layer is kept with the organic phase.

The organic phase is extracted three times with 80 ml HCl 10%.

The aq. solution is filtered and the pH adjusted first to 2-5 with NaOH 30% and afterwards with NaOH 5% to pH 7-8. IT is kept≤10° C. during pH addition.

The suspension is filtered and washed two times with 60 ml of water.

The product is dried at 45° C./<100 mbar to dryness.

Appearance:

HPLC Purity: 99.0%

Yield:

| | Theory | Found | Comments |
|---|---|---|---|
| Yield Crude | — | | |
| Final Yield beige powder | 17.52 g | 12.36 g | 70.60% |

HPLC Purity=99.8%

Water=0.04%

In experiments with a DCM water content of 0.04% by azeotroping the yield was even up to 85%.

Process Variant 2:

| Chemical | Molar Mass g/mol | mmol | Eq. | Theory |
|---|---|---|---|---|
| lithium-t-butoxid (tBuOLi) | 80.06 | 99.2 | 2.80 | 7.94 g |
| THF | — | — | 7.00 | 35.0 ml |
| 1,2-dibromomethane (DBE) | 187.86 | 60.2 | 1.70 | 11.32 g |
| THF | — | — | 1.50 | 7.5 ml |
| $Pd(PPh_3)_4$ (catalyst) | 1155.56 | 1.0 | 0.027 | 1.11 g |
| ethyl 4-oxazolcarboxylate | 141.12 | 35.4 | 1.00 | 5.00 g |
| THF | — | — | 1.50 | 7.5 ml |
| LiOH | 23.95 | 42.5 | 1.20 | 1.02 g |
| water | — | — | 3.5 | 17.5 ml |
| | | | 17.5 | 87.5 ml |
| MTBE | — | — | 2 × 7.00 | 2 × 35.0 ml |
| THF | | | 10.00 | 50.0 ml |
| HCl 20% | — | — | — | x ml |
| dichloromethane (DCM) | — | — | 14.0 | 70.0 ml |
| | | | 7.0 | 35.0 ml |
| | | | 7.0 | 35.0 ml |
| | | | 3.0 | 15.0 ml |
| | | | 3.0 | 15.0 ml |
| | | | ×10.0 | ×50.0 ml |
| DMF | — | — | 8.5 | 42.5 ml |
| | | | 1.5 | 7.5 ml |
| 4-methylmorpholine | 101.15 | 138.2 | 3.90 | 13.98 g |
| ethylchloro-formate (ECF) | 108.52 | 47.8 | 1.35 | 5.19 g |
| RM-2-a | 199.05 | 44.3 | 1.25 | 8.82 g |
| THF | — | — | 1.95 | 9.8 ml |
| water | — | — | 13.0 | 65.0 ml |
| | | | 3.0 | 15.0 ml |
| | | | 3.0 | 15.0 ml |

Procedure:

A reactor is purged with nitrogen for 15 min, the condensator is cooled to −30C°.

tBuOLi is charged to the reactor and THE is added. The mixture is heated to TI=55° C. (TM=58° C.) and stirred for 5 min. A solution of 1,2-dibromomethane in THF is added at TI≤60° C. The mixture is stirred at TI=60° C. (TM=63° C.) for 60 min. The mixture is cooled to TI=45° C.

Pd(PPh3)4 is added. The mixture is heated to TI=60° C. (TM=63° C.).

A solution of ethyl 4-oxazolcarboxylate in THF is added at TI≤65° C. The mixture is stirred for 30 min at TI=60° C. (TM=63° C.). The mixture is cooled to TI=20-25° C. (TM=20° C.).

IPC via HPLC-MS.

A solution of LiOH in water is added at TI≤25° C. The mixture is stirred at TI=25° C. for ≥16 h.

IPC via HPLC-MS

Water is added and the mixture is extracted 2× with MTBE. The MTBE phases are discarded.

THF is added and the pH adjusted to 0.5-1.0 at 15° C.-20° C. with

HCl 20%. The mixture is extracted 3× with DCM. The combined organic extracts are dried over $MgSO_4$, filtered and the filter cake washed with DCM. DCM is evaporated at 35° C./400 mbar. 8.5 EQ DMF are added and THF evaporated at 35° C./to 35 mbar. End points of distillation are when no further solvent is condensing.

IPC via KF≤0.2% water, otherwise additional azeotroping.

For further azeotroping, 10Eq DCM are added and evaporated at 35° C./400 mbar. IPC via KF is repeated.

This procedure is repeated till IPC via KF is in spec. 4-Methylmorpholine is added to DMF solution at TI=−5° C.-0° C. Ethylchloroformate is added at TI=−5° C.-0° C. RM-2-a (milled) is added at TI=−5° C.-0° C.. The mixture is stirred ≥5 h bei TI=−3° C.

IPC via HPLC-MS

If IPC IM2>85% a/a, water is added at IT<10° C.

The pH of reaction mixture is adjusted to pH 6-8 with NaOH 30% if necessary. The product suspension is stirred≥60 min at IT 0-5° C., filtered, washed twice with water and dried at 45° C. in vacuo.

Yield:

Yield=5.5 g=62.4%

HPLC Assay=99.6% m/m

HPLC Purity=99.7% a/a

4. Process for Preparing the Compound (II) in the Form of a 3HCl-Salt—Telescoped Synthesis with Solvent Exchange Process Variant 1 (Solvent Extraction):

Chemicals:

| | Molar Mass | | | | |
|---|---|---|---|---|---|
| Chemical | g/mol | mmol | Eq. | Mass th. | Mass is |
| RM-3-a | 161.20 | 486.4 | 1.2 | 78.4 g | 78.4 g |
| water | — | — | — | 6500 ml | 6500 ml |
| NaOH 30% | 39.99 | 40.5 | 0.1 | 5.4 g | 5.4 g |
| IM-3-b | 247.23 | 404.5 | 1.0 | 100.00 g | 100 g |
| DCM | | | | 4 × 3200 ml | 4 × 3200 ml |
| EtOAc | | | | 3 × 3200 ml | 3 × 3200 ml |
| ethanol | | | | 1 × 3200 ml | 2 × 3200 ml |
| | | | | 1 × 5600 ml | 1 × 4600 ml |
| HCl 32% | 36.46 | 100.4 | (2.5) | 114.4 g | 114.4 g |

Reaction:

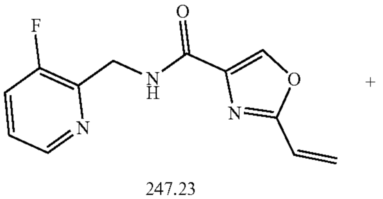

247.23
IM-3-b

-continued

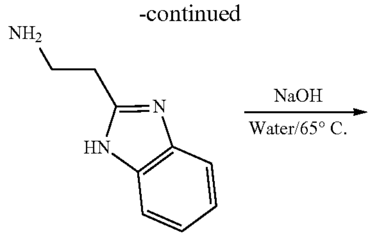

161.20
RM-3-a

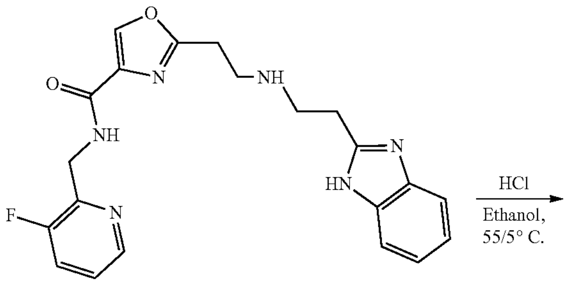

408.43
(II)

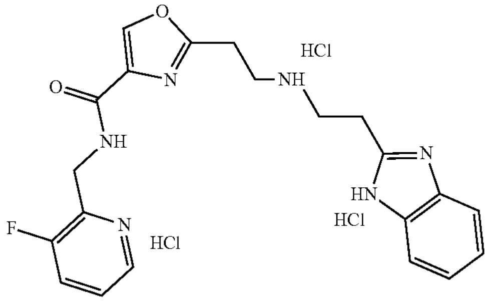

517.81
(II) 3HCl

Procedure:

The intermediate compound IM-3-b may be prepared as described in Example 3.

Compound RM-3-a (grinded) is charged to the reactor and suspended in water at 20-25° C. NaOH 30% is dosed and the suspension stirred at 20-25° C. until a solution is formed (approx 15 min).

Intermediate compound IM-3-b (grinded) is added and the mixture heated to 60-65° C. for 72 h.

IPC via LC/MS conversion ≥93% area.

The mixture is cooled to 20-25° C. and DCM is added.

The pH is adjusted to 3.9-4.1 with HCl 10%.

The mixture is stirred for 5 min and the phases are rested for 1 h. The lower phase is discarded.

The DCM extraction is repeated three times.

The aq. phase is adjusted to pH 9.9-10.1 with NaOH 15% and EtOAc is added.

The mixture is stirred for 5 min and the phases are rested for 1 h. The lower phase is discarded.

The EtOAc extraction is repeated two times.

The organic phases are combined (volume=8.5 l) and are concentrated under vacuum/OT 40° C. to a volume of 1.7 l (⅕ of volume).

3.2 l EtOH is added and the solution is concentrated under vacuum/OT 40° C. to a volume of 1.7 l (½ of volume).

3.2 l EtOH is added and the solution is concentrated under vacuum/OT 40° C. to a volume of 1.05 l (⅓ of volume).

4.55 l EtOH (5.6 l-1.05 l) is added and the solution is filtered and heated to 55-60° C.

HCl 32% is dosed within ≥20 min at 55-60° C. and the suspension is cooled slowly to 0-5° C. within ≥3 h.

The suspension is stirred at 0-5° C. ≥1 h and filtered.

The filtered cake is washed with 0.8 l EtOH and dried at 45° C./vacuum <50 mbar to dryness.

Yield:

| | Theory | Found | Comments |
|---|---|---|---|
| Yield Crude | — | | |
| Yield final Product (white to off-white powder) | 209.4 g | 142.3 g | 68% uncorr/65% corr |

HPLC Assay: 75.8% m/m free base, 96.2% m/m salt

HPLC Purity: 99.2% area

Figure 6:
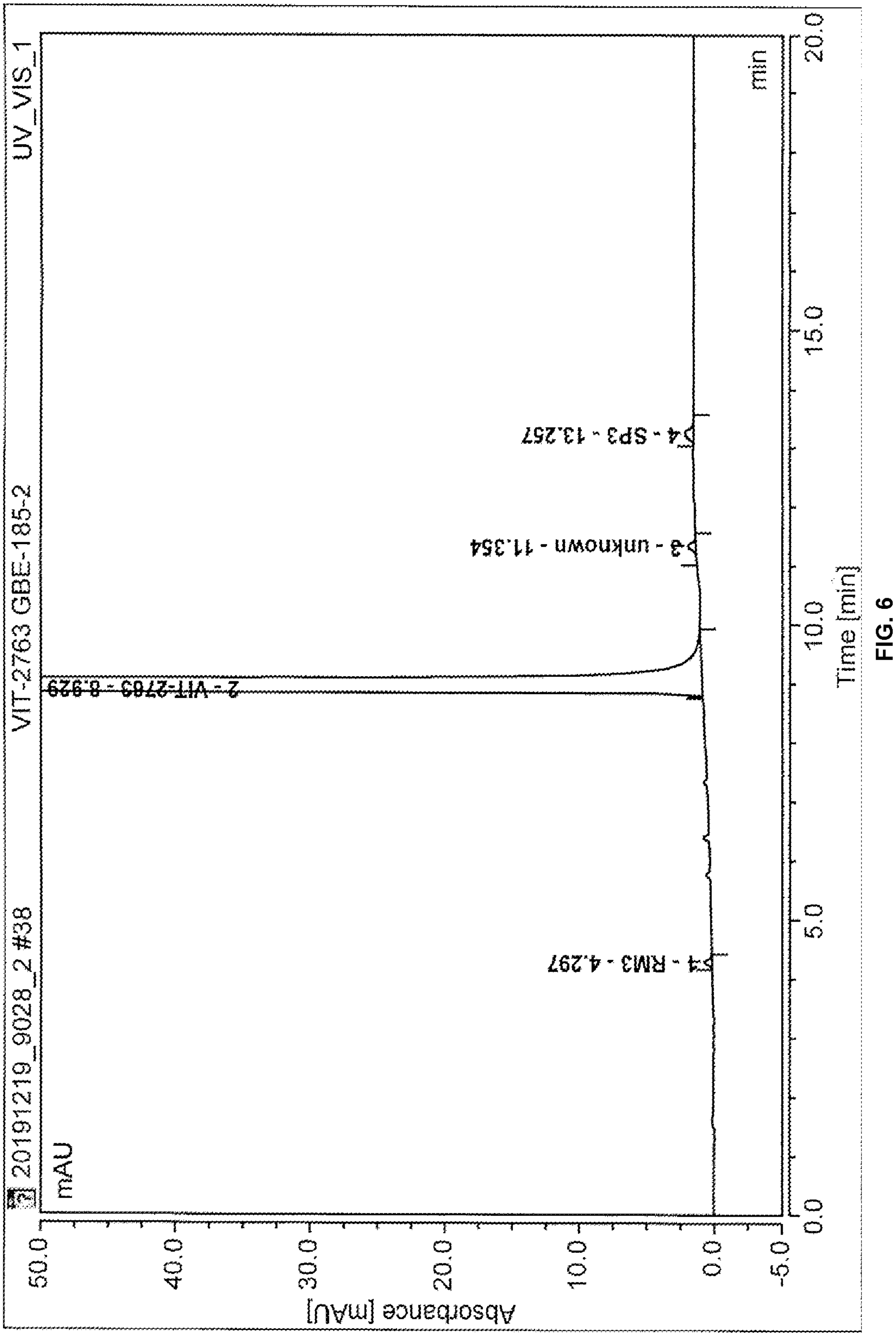
FIG. 6: HPLC Chromatogram showing the impurity profile of Compound (II) in the form a 3HCl salt (polymorph PM1) prepared with the process according to Example 4 followed by solvent extraction (process variant 1)

The HPLC purity profile is shown in FIG. 6

Water content: 1.2%

Chloride content (elemental analysis): average value 19.8% (m/m), which is close to the expected value of 20.5% for a 3:1 HCl: free base salt

DSC: 192° C.

PXRD analysis: polymorph form PM1 (PXRD pattern according to FIG. 1)

Process Variant 2 (Oil Separation):

Reaction:

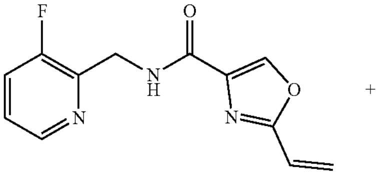

IM-3-b

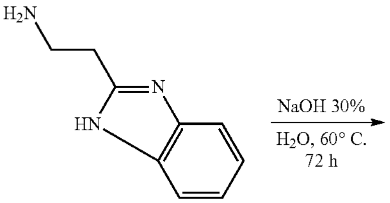

RM-3-a

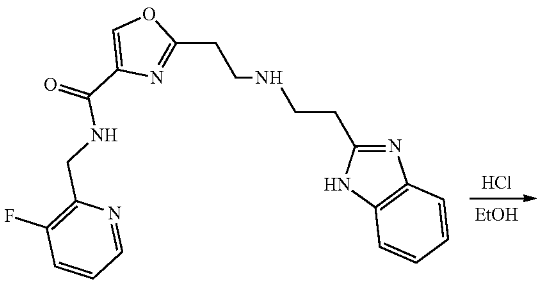

(II)

-continued

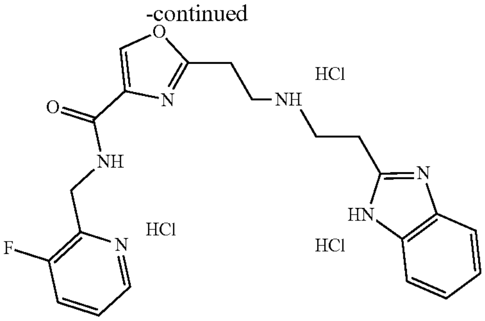

(II) 3HCl

Chemicals:

| | Molar Mass | | | |
|---|---|---|---|---|
| Chemical | g/mol | mmol | Eq. | Mass th. |
| RM-3-a | 161.20 | 40.4 | 1.0 | 6.52 g |
| water | — | — | — | 100 ml |
| NaOH 30% | 39.99 | 0.4 | 0.01 | 54 mg |
| IM-3-b | 247.23 | 40.4 | 1.0 | 10.00 g |
| EtOH 99% | | — | — | 560 ml |
| HCl 32% | 36.46 | 100.0 | (2.5) | 11.51 g |

RM-3-a is charged to a reactor and suspended in water. NaOH 30% is added. IM-3-b is added and the mixture heated to IT 58-62° C. for ≥72 h. IPC via LC/MS product ≥75% area (all compounds integrated).

The mixture is cooled to 5-25° C. and allowed to rest for ≥16 h. The bottom oil phase is separated by drain off the reactor, decanting or suction off the water phase by vacuum. The separated oil phase is dissolved in 560 ml EtOH. The solution is filtered and heated to IT 60-65° C. 0.7 mg seeding crystals are added. HCl 32% is dosed within 20 min at IT 60-65° C. with a stirrer speed of 100 rpm. After HCl addition the stirrer speed is lowered to 60 rpm and the suspension is cooled slowly to IT 0-5° C. within ≥4 h. The suspension is stirred at 0-5° C. ≥1 h and filtered. The filter cake is washed with 105 ml EtOH and dried at 45° C./vacuum <50 mbar to dryness.

Yield:

| | Theory | Found | Comments |
|---|---|---|---|
| Yield Crude | — | | |
| Yield final Product | 20.93 g | 13.7 g | 65.40% |

HPLC Assay: 77.4% m/m free base, 98.3% m/m salt

Corr. Yield = 64.3%

HPLC Purity: 99.7% area

Figure 7:
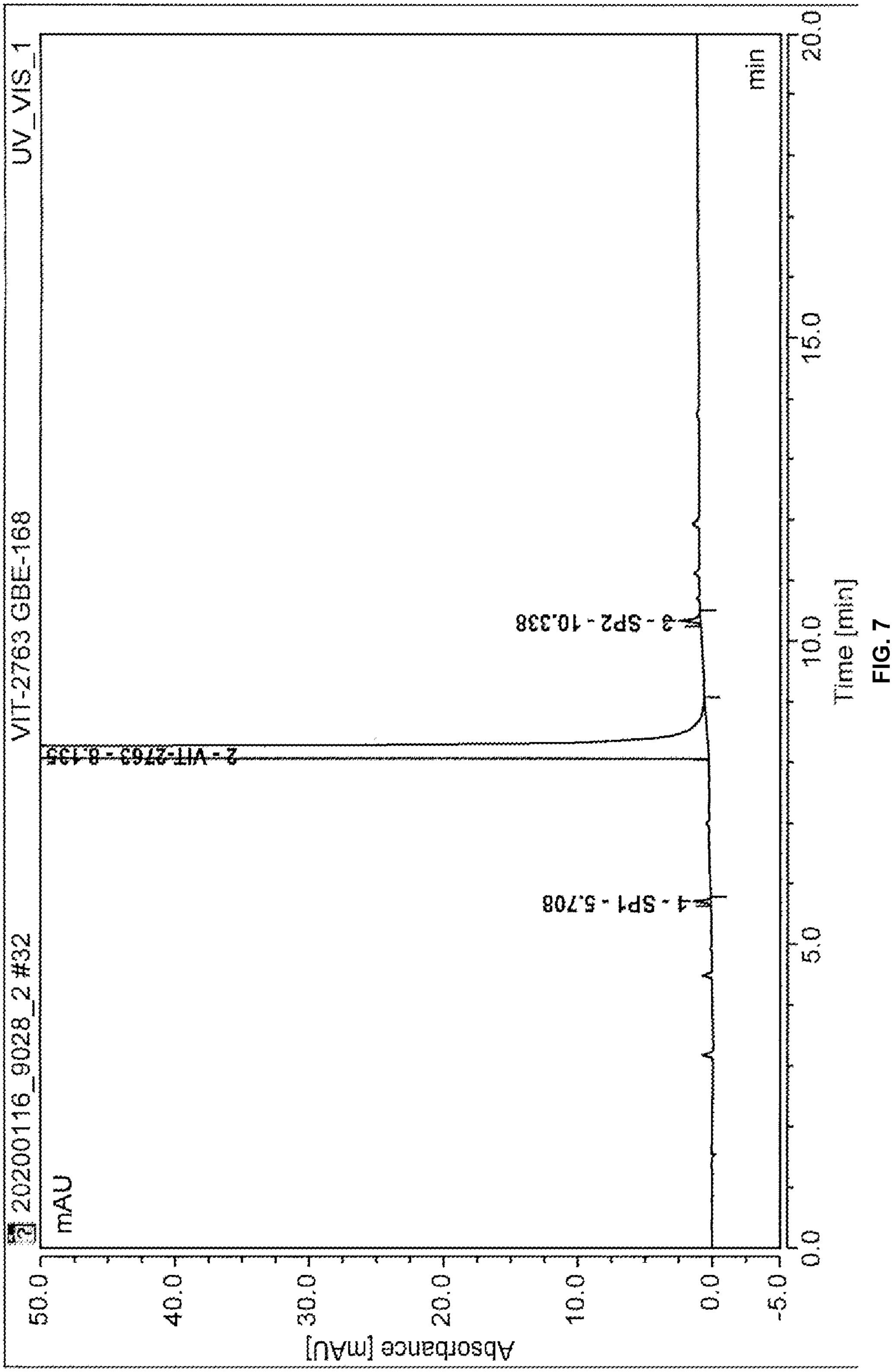
FIG. 7: HPLC Chromatogram showing the impurity profile of Compound (II) in the form a 3HCl salt (polymorph PM1) prepared with the process according to Example 4 followed by oil separation (process variant 2)

The HPLC purity profile is shown in FIG. 7

Preparation of Polymorph PM2 of the Compound (II) in the Form of a 3HCl-Salt

The polymorph form PM2 is obtained by hot recrystallization of a solution of the compound (II) as the 3HCl salt in the form of polymorph PM1 as obtained in Example 4 described above.

The hot recrystallization was carried out in a solvent mixture of toluene: methanol in a ratio of 1:1.

The $^1H$ NMR spectrum of polymorph PM2 is essentially unchanged compared to that of polymorph PM1 but shows a sharp singlet at ~δ3.16 ppm assigned to methanol that suggests a methanol content of ~2 mole percent.

Elemental analysis of polymorph PM2 to determine the amount of chloride provided an average value of 20.0% (m/m), which is in good accordance with the expected value of 20.5% for a 3:1 HCl:free base salt.

DSC: 226° C.

Figure 2:
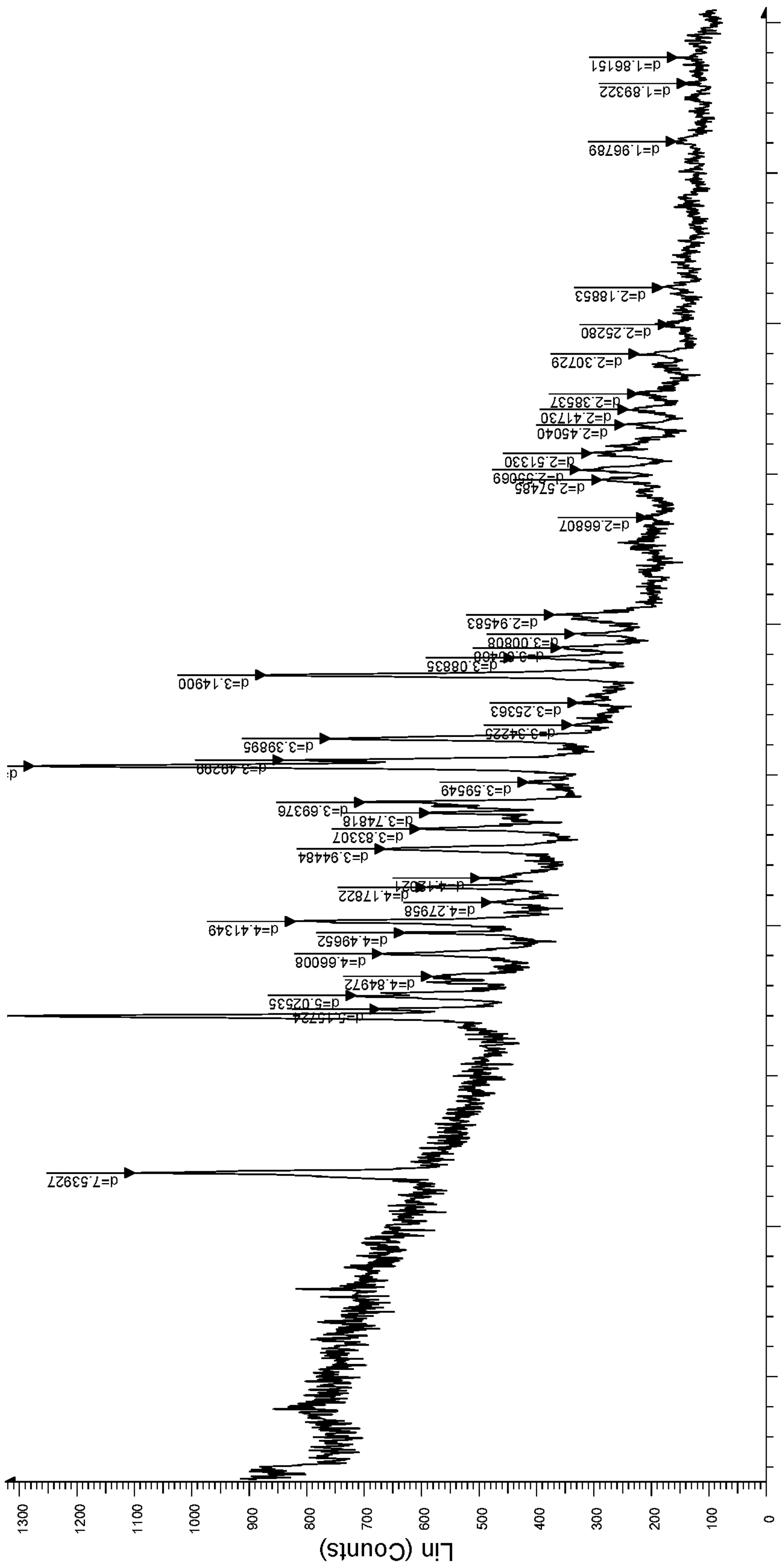
FIG. 2: PXRD pattern of Compound (II) in the form of the 3HCl salt (polymorph PM2)

PXRD analysis: polymorph form PM2 (PXRD pattern according to FIG. 2)

Preparation of Polymorph PM3 of the Compound (II) in the Form of a 3HCl-Salt

The polymorph form PM3 is obtained by preparing a saturated solution of the compound (II) as the 3HCl salt in the form of polymorph PM1 as obtained in Example 4 described above in a solvent mixture of acetone:water in a ratio of 9:1 (v/v) at 50° C., cooling to 5° C., then precipitating a white solid by adding acetone.

The $^1H$ NMR spectrum of polymorph PM3 exhibits only minor differences compared to that of polymorph PM1 with a slight shift in the broad resonances.

Elemental analysis of polymorph PM3 to determine the amount of chloride provided an average value of 19.3% (m/m), which is in good accordance with the expected value of 20.5% for a 3:1 HCl:free base salt.

DSC: 169° C.

Figure 3:
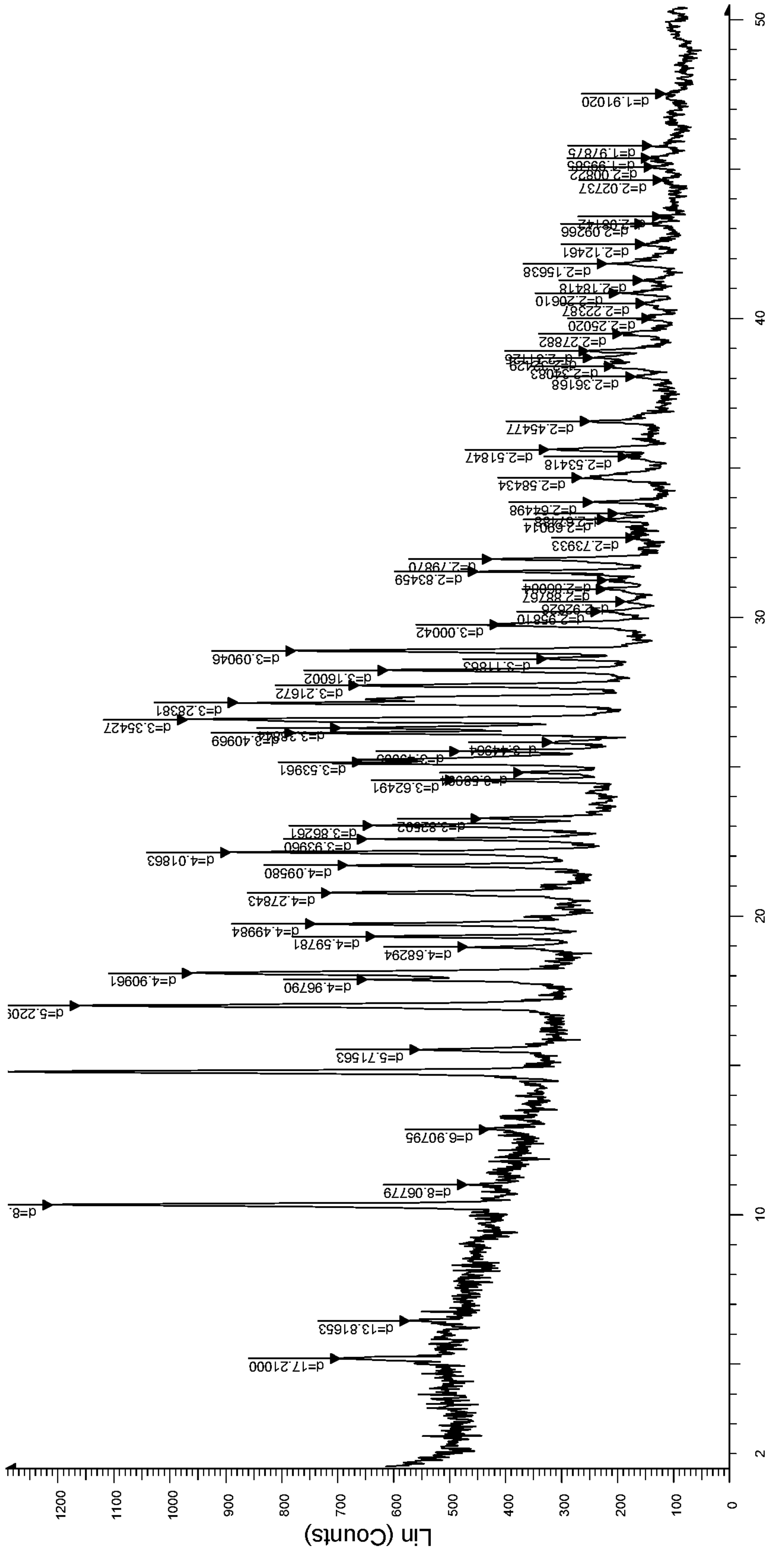
FIG. 3: PXRD pattern of Compound (II) in the form of the 3HCl salt (polymorph PM3)

PXRD analysis: polymorph form PM3 (PXRD pattern according to FIG. 3)

5. Process for Preparing the Compound (II) in the Form of the HCl Salt (Mono-Salt)-Telescoped Synthesis Chemicals:

| | Molar Mass | | | amount | amount |
|---|---|---|---|---|---|
| Chemical | g/mol | mmol | Eq. | th. | is |
| RM-3-a | 161.20 | 97.3 | 1.2 | 15.68 g | |
| water | — | — | — | 1300 ml | |
| NaOH 30% | 39.99 | 8.2 | 0.1 | 1.08 g | |
| IM-3-b | 247.23 | 81.0 | 1.0 | 20.00 g | |
| HCl 20% | | | | x ml | |
| DCM | | — | — | 650 ml | |
| ethanol | | | | 160 ml | |

Reaction:

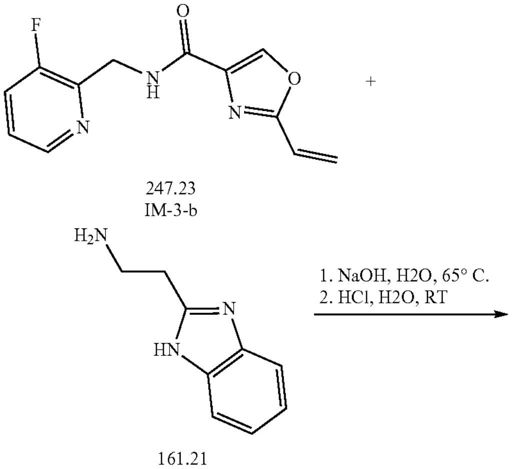

247.23
IM-3-b 161.21
RM-3-a

-continued

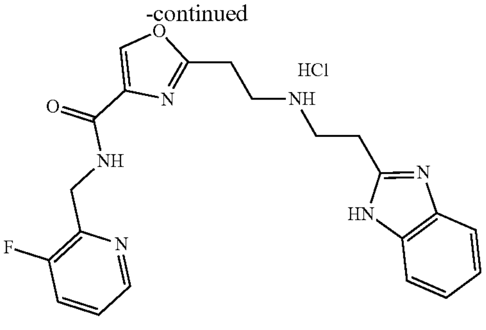

444.90
(II) HCl

Procedure:

The intermediate compound IM-3-b may be prepared as described in Example 3.

Compound RM-3-a (grinded) is suspended in water at 20-25° C. and NaOH 30% is added.

The suspension is stirred for ≥15 min at 20-25° C. to form a solution.

Intermediate compound IM-3-b (grinded) is added and the suspension heated to 60-65° C. for ≥72 h.

IPC control via HPLC ≥93% conversion.

The emulsion is cooled to 20-25° C. and 650 ml DCM are added.

The mixture is stirred for ≥10 min and the phases are rested for ≥1 h. The water phase is discarded.

650 ml water are added to the DCM phase and the pH is adjusted to 5.4-5.6 with HCl 20%.

The mixture is stirred vigorous for ≥10 min and the phases are rested for ≥1 h. The DCM phase is discarded.

The water phase is stirred for ≥16 h and the resulting suspension is filtered.

The wet cake is washed with 80 ml of EtOH.

The filtered cake is dried at 50° C./<100 mbar to dryness.

Yield:

| | Theory | Found | Comments |
|---|---|---|---|
| Yield Crude Product | — | | |
| Yield final Product | 36.0 g | 21.0 g | 59.00% |

HPLC Assay: 88.7% m/m free base, 96.6% m/m
Corr. Yield = 57%
HPLC Purity = 98.4% area
DSC = 173 °C 6. Process for Preparing the Compound (II) in the Form of the $H_2SO_4$ Salt—Telescoped Synthesis Chemicals:

| | Molar Mass | | | amount | amount |
|---|---|---|---|---|---|
| Chemical | g/mol | mmol | Eq. | th. | is |
| RM-3-a | 161.20 | 97.3 | 1.2 | 15.68 g | |
| water | — | — | — | 1300 ml | |
| NaOH 30% | 39.99 | 8.2 | 0.1 | 1.08 g | |
| IM-3-b | 247.23 | 81.0 | 1.0 | 20.00 g | |
| $H_2SO_4$ 20% | | | | x ml | |
| DCM | | — | — | 640 ml | |
| ethanol | | | | 160 ml | |

Reaction:

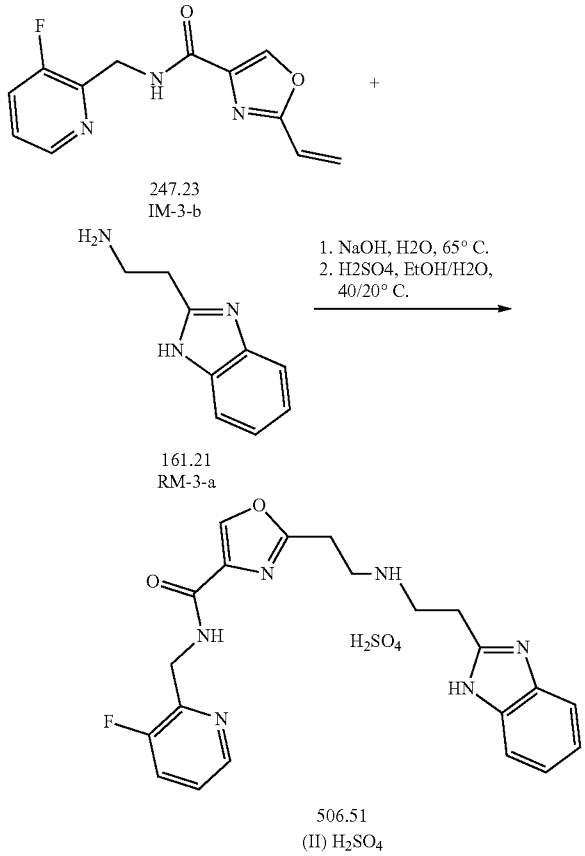

247.23
IM-3-b
161.21
RM-3-a
506.51
(II) $H_2SO_4$

Procedure:

The intermediate compound IM-3-b may be prepared as described in Example 3.

Compound RM-3-a (grinded) is suspended in water at 20-25° C. 30% NaOH is added and the mixture stirred ≥15 min at 20-25° C.

Intermediate compound IM-3-b (grinded) is added and the mixture heated to 60-65° C. for ≥72 h.

IPC conversion via HPLC ≥93%.

The mixture is cooled to 20-25° C.

640 ml DCM are added, stirred and the phases are rested for ≥1 h. The water phase is discarded.

640 ml water are added to the DCM phase and the pH adjusted to 3.4-3.6 with 20% $H_2SO_4$.

The phases are rested for ≥1 h and the DCM phase is discarded.

The water phase is stirred and cooled to 0-5° C. within ≥2 h.

The suspension is heated to 40° C. and stirred for ≥16 h at this temperature. The suspension is cooled to 0-5° C. within ≥4 h and stirred at 0-5° C. for ≥1 h.

The suspension is filtered and the filtered cake washed with 160 ml ethanol.

The filtered cake is dried at 50° C./<100 mbar vacuum to dryness.

Yield:

| | Theory | Found | Comments |
|---|---|---|---|
| Yield Crude | — | | |
| Yield final Product (white to off-white powder) | | 24.6 g | 60% uncorr. |

HPLC Assay: 76.4% m/m free base, 94.8% m/m 1:1 salt
Corr. Yield = 57%
HPLC Purity: 98.3% area
$H_2O$/KF = 2.3%
DSC: 176 °C 7. Process for Preparing the Compound (II) in the Form of the $0.5H_3PO_4$ Salt—Telescoped Synthesis Chemicals:

| | Molmasse | | | Amount | Amount |
|---|---|---|---|---|---|
| Chemical | g/mol | mmol | Eq. | (th) | (is) |
| RM-3-a | 161.2 | 48.64 | 1.2 | 7.84 g | |
| water | — | — | — | 650 ml | |
| NaOH 30% | 39.99 | 4.1 | 0.1 | 0.54 g | |
| IM-3-b | 247.23 | 40.5 | 1.0 | 10.00 g | |
| DCM | | | | 4 x 320 ml | |
| ethylacetate | | | | 3 x 320 ml | |
| ethanol | | | | 320, 110, 40 ml | |
| $H_3PO_4$ 30% | | | | 5 x 6.5 ml | |

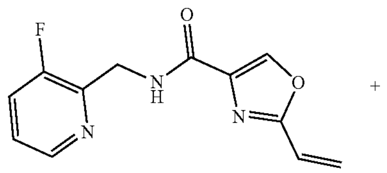

247.23
IM-3-b

-continued

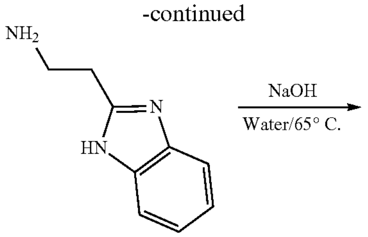

161.20
RM-3-a

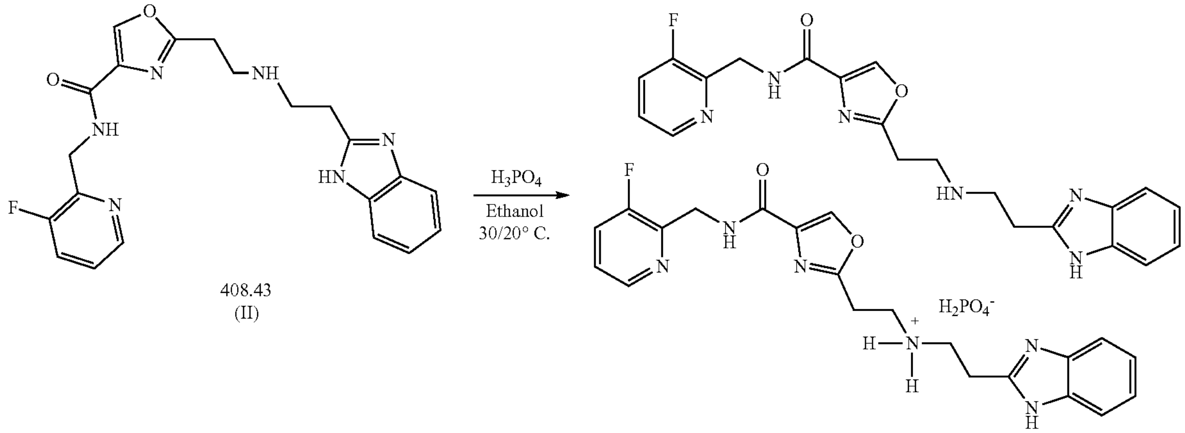

408.43
(II)

914.85
(II) 0.5 $H_3PO_4$

Procedure:

The intermediate compound IM-3-b may be prepared as described in Example 3.

Compound RM-3-a (grinded) is suspended in water at 20-25° C. and NaOH 30% is added.

The suspension is stirred for ≥15 min at 20-25° C. to form a solution. Intermediate compound IM-3-b (grinded) is added and the suspension heated to 60-65° C. for ≥72 h.

IPC control via HPLC ≥93% conversion.

The emulsion is cooled to 20-25° C. and 320 ml DCM are added.

The pH is adjusted to 3.9-4.1 with HCl 20%.

The mixture is stirred vigorous for ≥10 min and the phases rested for ≥1 h. The organic phase is discarded.

This DCM extraction is repeated further 3 times.

The water phase is adjusted to pH 9.9-10.1 with NaOH 30%. 320 ml EtOAc are added and the mixture is stirred vigorous for ≥10 min. The phases are rested for ≥1 h. The water phase is discarded.

This EtOAc is extraction is repeated further 2 times.

The combined organic phases are concentrated in vacuum at 40° C. to 13 ml.

320 ml ethanol are added and the solution is concentrated to a volume of 18 ml.

110 ml of ethanol are added and 5×6.5 ml $H_3PO_4$ 30% are added at 20-25° C. The mixture is stirred ≥24 h at 28-32° C. The suspension is cooled to 20-25° C. within ≥1 h and filtered. The filtered cake is washed with 40 ml of EtOH.

The filtered cake is dried at 45° C./<100 mbar to dryness.

Yield:

| | Theory | Found | Comments |
|---|---|---|---|
| Yield Crude | — | | |
| Yield Final Product | 18.5 g | 8.8 g | 48.00% |

HPLC Assay: 85.2% m/m free base, 95.4% m/m 2:1 salt

Corr. Yield = 45.8%

HPLC Purity = 99.5% area

P = 3.3%

DSC = 253 °C

8. Process for Preparing the Compound (II) in the Form of the $H_3PO_4$ Salt—Transformation to the 1:1 Salt Chemicals:

| | Molmasse | | | Amount | Amount |
|---|---|---|---|---|---|
| Chemical | g/mol | mmol | Eq. | (th) | (is) |
| Compound (II) 0.5 $H_3PO_4$ salt | 914.85 | 13.1 | | 12 g | |
| ethanol | — | — | — | 180 ml | |

Reaction:

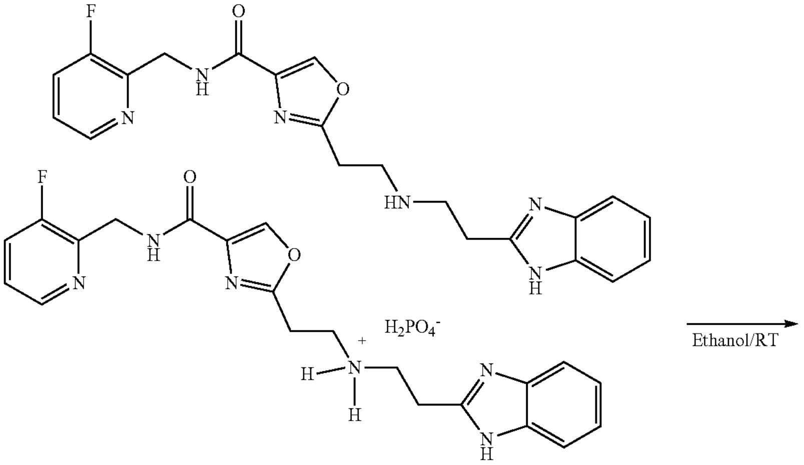

MW 914.85
(II) 0.5 $H_3PO_4$ salt

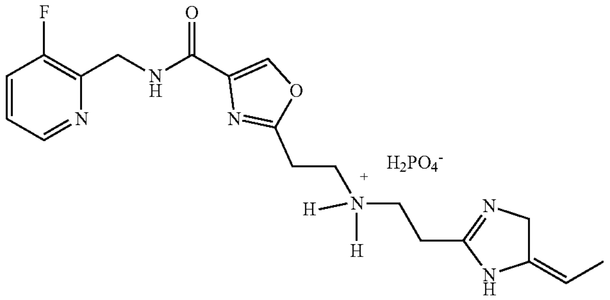

MW 506.42
(II) 0.5 $H_3PO_4$ salt

Procedure:

The $0.5H_3PO_4$ salt of compound (II) can be prepared as described in Example 7.

The compound (II) $0.5H_3PO_4$ salt is suspended in ethanol at 20-25° C. and stirred for 4 days at this temperature.

The suspension is filtered and the wet cake dried at 45° C./<100 mbar to dryness.

Yield:

| | Theory | Found | Comments |
|---|---|---|---|
| Yield Crude Product | — | | |
| Yield Final Product | 13.3 g | 6.6 g | 50.00% |

Yield: 6.6g = 50% with regard to free base
HPLC Assay: 78.3% m/m free base, 97% m/m 1:1 salt
Corr. Yield = 48.5%
HPLC Purity: 98.7% area
P = 5.7%
DSC: 182 °C 9a. Process for Preparing an Intermediate Compound (IM-3-b')

Chemicals:

| | Molar Mass | | | Quantiy | Quantiy |
|---|---|---|---|---|---|
| Chemical | g/mol | mmol | Eq. | (th.) | (eff.) |
| IM-2-a (2-Vinyloxazole-4 carboxylic acid) | 139.11 | 15.4 | 1.00 | 2.14 g | 2.15 g |

-continued

| Chemical | Molar Mass g/mol | mmol | Eq. | Quantiy (th.) | Quantiy (eff.) |
|---|---|---|---|---|---|
| Dichlormethane | — | — | — | 40 ml | 40 ml |
| 4-Methylmorpholine | 101.15 | 58.5 | 3.80 | 5.91 g | 5.89 g |
| Ethylchloroformate | 108.52 | 19.2 | 1.25 | 2.09 g | 2.08 g |
| RM-2-a' (2-(Aminomethyl)-3-bromopyridine) | 259.96 | 19.2 | 1.25 | 5.00 g | 5.03 g |
| NaCl liquid 10% | — | — | — | 3 × 40 ml | 3 × 40 ml |

Reaction:

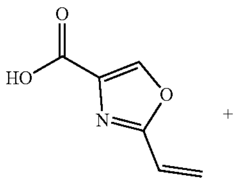

139.11
IM-2-a

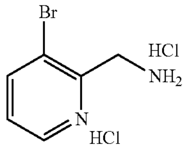

259.96
RM-2-a' HCl salt

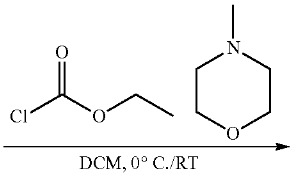

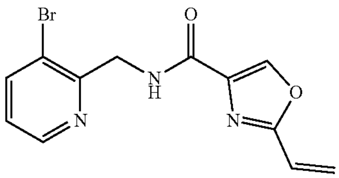

308.14
IM-3-b'

Procedure:

The reaction is carried out under an $N_2$ flow.

2-vinyloxazole-4-carboxylate (IM-2-a) is suspended in dichloromethane and cooled to −5° C.

4-Methylmorpholine is added dropwise in such a way that the temperature did not exceed 0° C. (exothermic).

Ethyl chloroformate is added dropwise in such a way that the temperature did not exceed 0° C. (exothermic).

After a stirring time of 20 min, 2-(aminomethyl)-3-bromopyridine (RM-2-a') is added in such a way that the temperature did not exceed 0° C.

The mixture is stirred overnight at 0° C.-5° C.

The mixture is washed three times with 10% NaCl solution.

The organic phases are concentrated at 45° C. on a rotavap.

EtOAc/Heptane 20:80 (1.7 ml/g) is added to the crude product, stirred at RT for 4 h, filtered off, washed twice with EtOAc/Hepatne and dried at 50° C. to constant weight.

Yield:

| | Theory | Found | Comments |
|---|---|---|---|
| Yield | 4.76 g | 4.50 g | 94.54% |

4.5 g of beige solid observed = 94.5% yield of th.
$^1$H-NMR corresponds to structure observed = 94.5% yield of th.

9b. Process for Preparing the Compound (II')

Chemicals:

| Chemical | Molar Mass g/mol | mmol | Eq. | Quantiy (th.) | Quantiy (eff.) |
|---|---|---|---|---|---|
| RM-3-a (Benzimidazol-ethylamine) | 161.20 | 16.7 | 1.2 | 2.70 g | 2.72 g |
| Water | — | — | — | 225.00 | 225 ml |
| NaOH solution 30% | 39.99 | 1.4 | 0.1 | 0.19 g | 0.25 g |
| IM-3-b' | 308.14 | 14.0 | 1.0 | 4.30 g | 4.31 g |
| Dichlormethane | — | — | — | 4 × 110 ml | 4 × 110 ml |
| Ethylacetate | — | — | — | 3 × 110 ml | 3 × 110 ml |

Reaction:

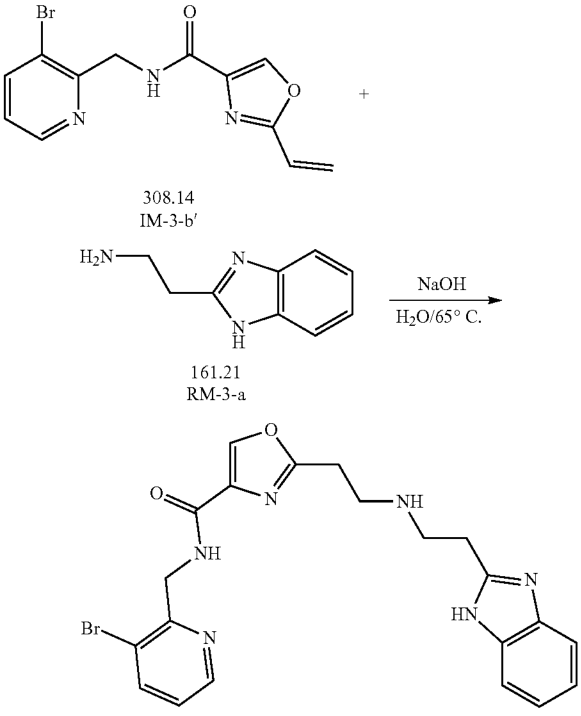

308.14
IM-3-b'

161.21
RM-3-a

M = 469.34
(II')

Procedure:

Benzimidazole-ethylamine (RM-3) is grounded in a mortar and suspended in water. 30% sodium hydroxide solution are added dropwise and stirred for 10 min at RT.

The intermediate Compound IM-3-b' is added to the mixture and stirred at an internal temperature of 63° C. for 72 hours.

The mixture is cooled to RT.

110 ml DCM are added and stirred for 10 minutes.

The pH value is set to 4 with HCl 20%.

The water phase is extracted 4 times with 110 ml DCM and rested for 1 hour for phase separation, DCM phases are discarded.

The water phase is adjusted to pH 10 with NaOH 30%, extracted 3 times with EtOAc and rested for 1 hour for phase separation, the water phases are discarded.

The EtOAc phases are dried with magnesium sulfate, filtered and concentrated on a Rotavap to dryness.

Yield:

| | Theory | Found | Comments |
|---|---|---|---|
| Yield | 6.56 g | 4.18 g | 63.72 % |

4.18 g of an brown oil are observed = 63.7% yield of th.

$^1$H-NMR corresponds to structure

9c. Process for Preparing the 3HCl-Salt of Compound (II')

Chemicals:

| Chemical | Molar Mass g/mol | Molar Mass mmol | Eq. | Quantiy (th.) | Quantiy (eff.) |
|---|---|---|---|---|---|
| Compound (II') | 469.34 | 8.9 | 1.0 | 4.16 g | 4.16 g |
| Ethanol | — | — | — | 168 ml | 170 ml |
| HCl 32% | 36.46 | 27.9 | 3.15 | 3.18 g | 3.23 g |
| Ethanol | — | — | — | 40 ml | 40 ml |

Reaction:

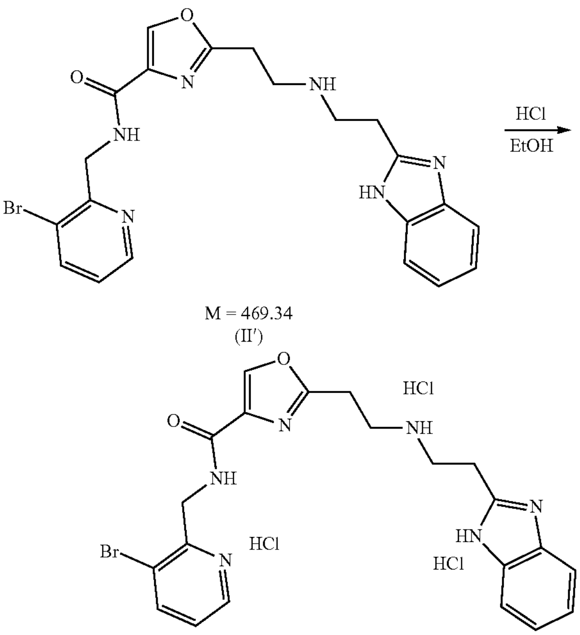

M = 469.34
(II')

M = 578.72
(II')-3HCl salt

Procedure:

Compound (II') is dissolved in ethanol and heated to an internal temperature of 40° C.

HCl 32% is added dropwise.

The suspension is cooled to 0° C. slowly.

The suspension is stirred at 0° C. for 1 h.

The suspension is filtered, the wet cake washed with ethanol and dried at 40° C. to dryness.

Yield:

| | Theory | Found | Comments |
|---|---|---|---|
| Yield | 5.13 g | 4.02 g | 78.36% |

4.02 g of a white solid observed = 78.4% yield of th.

$^1$H-NMR corresponds to structure

10. $^1$H-NMR, PXRD and DSC Analysis of Intermediate and Example Compounds 10.1 NMR-Analysis NMR analysis of Intermediate Compounds IM-1-a, IM-2-a and IM-3-b, which have been prepared with the process as described in Examples 1b, 1a and 3a, respectively, have been carried out providing the following NMR-data.

| | |
|---|---|
| IM-1-a according to Example 1b | $^1$H NMR (400 MHz, CHLOROFORM-d) δ ppm 8.24 (s, 1 H) 6.64 (dd, J = 17.6, 11.3 Hz, 1H) 6.29 (dd, J = 17.7, 0.8 Hz, 1H) 5.76 (dd, J = 11.4, 0.8 Hz, 1H) 4.40 (q, J = 7.3 Hz, 2H) 1.39 (t, J = 7.2 Hz, 3H) |
| IM-1-a according to Example 1c | $^1$H NMR (400 MHz, CDCl3): 0 8.14 (s, 1H), 6.63-6.56 (m, 1H), 6.27-6.22 (m, 1H), 5.71-5.68 (m, 1H), 4.36 (q, J = 6.8 Hz, 2H), 1.35 (t, J = 7.20 Hz, 3H) |
| IM-2-a | $^1$H NMR (400 MHz, DMSO-$d_6$) δ ppm 8.73 (s, 2H) 8.46 (s, 1 H, internal standard=1,2,4,5-Tetrachloro-3-nitrobenzene) 6.71 (dd, J = 17.5, 11.2 Hz, 1H) 6.22 (dd, J = 17.7, 1.0 Hz, 2H) 5.82 (dd, J = 11.2, 0.8 Hz, 2H) |
| IM-3-b | $^1$H NMR (400 MHz, DMSO-$d_6$) δ ppm 8.57-8.67 (m, 2H) 8.45 (s, 1H) 8.41 (dt, J = 4.7, 1.3 Hz, 1H) 7.71 (ddd, J = 10.2, 8.6, 1.3 Hz, 1H) 7.42 (dt, J = 8.5, 4.4 Hz, 1H) 6.72 (dd, J = 17.6, 11.3 Hz, 1H) 6.24 (dd, J = 17.7, 0.8 Hz, 1H) 5.83 (dd, J = 11.4, 0.8 Hz, 1H) 4.67 (dd, J = 5.6, 1.5 Hz, 2H) |

NMR analysis of Example Compounds (II) in the form of the 3HCl salt (polymorph form PM1, PM2 and PM2), 1HCl salt, $H_2SO_4$ salt, $0.5H_3PO_4$ salt and $1H_3PO_4$ salt, which have been prepared with the process as described in Examples 4, 5, 6, 7 and 8, respectively, have been carried out providing the following NMR-data.

| | |
|---|---|
| Example 4 PM1 | $^1$H NMR (400 MHz, DMSO-$d_6$) δ ppm 8.86 (t, J = 5.7 Hz, 1H) 8.61 (s, 1H) 8.45 (d, J = 4.8 Hz, 1H) 7.86 (ddd, J = 9.8, 8.6, 1.1 Hz, 1H) 7.75-7.82 (m, 2H) 7.44-7.61 (m, 3H) 4.66 (br d, J = 5.1 Hz, 2H) 3.77 (s, 4H) 3.49 (br t, J = 6.7 Hz, 2H) 3.38 (br t, J = 7.1 Hz, 2H) 3.01 (s, 35 H; internal standard=dimethylsulfone) |
| Example 5 | $^1$H NMR (400 MHz, DMSO-$d_6$) δ ppm 8.66 (t, J = 5.7 Hz, 1H) 8.63 (s, 1H) 8.37 (dt, J = 4.7, 1.3 Hz, 1H) 7.70 (ddd, J = 10.2, 8.6, 1.3 Hz, 1H) 7.46-7.62 (m, 2H) 7.40 (dt, J = 8.6, 4.3 Hz, 1H) 7.01-7.28 (m, 2H) 4.62 (dd, J = 5.8, 1.3 Hz, 2H) 3.08-3.67 (m, 12H) 1.06 (t, J = 7.1 Hz, 1H) |
| Example 6 | $^1$H NMR (400 MHz, DMSO-$d_6$) δ ppm 10.00 (br s, 1H) 8.64 (s, 1H) 8.58 (t, J = 5.7 Hz, 1H) 8.36 (dt, J = 4.6, 1.5 Hz, 1H) 7.70 (ddd, J = 10.2, 8.6, 1.3 Hz, 1H) 7.46-7.62 (m, 2H) 7.41 (dt, J = 8.5, 4.4 Hz, 1H) 7.06-7.24 (m, 2H) 4.62 (dd, J = 5.7, 1.4 Hz, 2H) 3.39-3.70 (m, 4H) 3.27 (dt, J = 10.3, 7.0 Hz, 4H) |
| Example 7 | $^1$H NMR (400 MHz, DMSO-$d_6$) δ ppm 8.58 (t, J = 5.7 Hz, 1H) 8.53 (s, 1H) 8.37 (dt, J = 4.8, 1.4 Hz, 1H) 7.70 (ddd, J = 10.0, 8.5, 1.3 Hz, 1H) 7.43-7.56 (m, 2H) 7.33-7.43 (m, 1H) 7.05-7.18 (m, 2H) 4.61 (dd, J = 5.6, 1.3 Hz, 2H) 2.98-3.25 (m, 8H) |
| Example 8 | $^1$H NMR (400 MHz, DMSO-$d_6$) δ ppm 8.59 (br t, J = 5.7 Hz, 1H) 8.55 (s, 1H) 8.37 (dt, J = 4.7, 1.3 Hz, 1H) 7.69 (ddd, J = 10.0, 8.5, 1.3 Hz, 1H) 7.43-7.56 (m, 2H) 7.40 (dt, J = 8.5, 4.4 Hz, 1H) 7.00-7.20 (m, 2H) 4.61 (dd, J = 5.6, 1.0 Hz, 2H) 3.05-3.35 (m, 8H) |

NMR analysis of Intermediate Compound IM-3-b', Compound (II') and the 3HCl salt of Compound (II'), which have been prepared with the process as described in Examples 9a, 9b and 9c, respectively, have been carried out providing the following NMR-data.

| | |
|---|---|
| IM-3-b' according to Example 9a | $^1$H NMR (400 MHz, DMSO-$d_6$) δ = 8.66 (s, 1H), 8.63-8.48 (m, 2H), 8.11 (dd, J = 1.5, 8.1 Hz, 1H), 7.31 (dd, J = 4.7, 8.0 Hz, 1H), 6.74 (dd, J = 11.3, 17.6 Hz, 1H), 6.24 (dd, J = 0.8, 17.7 Hz, 1H), 5.84 (dd, J = 0.8, 11.2 Hz, 1H), 4.63 (d, J = 5.3 Hz, 2H) |
| (II') according to Example 9b | $^1$H NMR (400 MHz, DMSO-$d_6$) δ = 8.56 (dd, J = 1.4, 4.7 Hz, 2H), 8.54 (s, 2H), 8.51 (t, J = 5.5 Hz, 2H), 8.45 (s, 3H), 8.09 (dd, J = 1.4, 8.0 Hz, 2H), 7.50-7.41 (m, 4H), 7.30 (dd, J = 4.7, 8.0 Hz, 2H), 7.14-7.06 (m, 4H), 4.62 (d, J = 5.3 Hz, 4H), 3.07-2.92 (m, 16H) |
| (II') 3HCl according to Example 9c | $^1$H NMR (400 MHz, DMSO-$d_6$) δ = 16.16-14.70 (m, 1H), 10.56-9.46 (m, 2H), 8.71 (t, J = 5.7 Hz, 1H), 8.64 (s, 1H), 8.56 (dd, J = 1.4, 4.7 Hz, 1H), 8.12 (dd, J = 1.3, 8.1 Hz, 1H), 7.82-7.76 (m, 2H), 7.58-7.51 (m, 2H), 7.32 (dd, J = 4.7, 8.0 Hz, 1H), 4.60 (d, J = 5.6 Hz, 2H), 3.54-3.44 (m, 2H), 3.44-3.35 (m, 2H) |

10.2 PXRD-Analysis

Further PXRD analysis of Example Compounds (II) in the form of the 3HCl salt (PM1, PM2 and PM3), $H_2SO_4$ salt and $1H_3PO_4$ salt, which have been prepared with the process as described in Examples 4, 6 and 8, respectively, have been carried out providing the PXRD spectra as shown in FIGS. 1 to 5.

Method

Sample Preparation and Measurement:

Sample preparation: 10 to 20 mg sample was placed between two acetate foils in Stoe transmission sample holder; the sample was rotated during the measurement Stoe Stadi P (G.52.SYS.S072); Mythen1K Detector; Cu-Ka1 radiation; standard measurement conditions: transmission; 40 kV and 40 mA tube power; curved Ge monochromator;

0.02° 2Theta step size, 48 s step time, 1.5-50.5° 2Theta scanning range; detector mode: step scan; 1° 2Theta detector step;

Data Evaluation:

the d-value Analysis was performed with software EVA from Bruker, version 14, 0, 0, 0 background was subtracted only lines up to 35° 2theta were listed calculation of relative intensity with formula in Excel PXRD Conditions—Compound (II) 3HCl Salt (PM1, PM2 and PM3 of FIGS. 1, 2 and 3)

| | |
|---|---|
| Geometry | Transmission; angular range covered by detector: 12.59° 2T = intrinsic resol. 0.01° 2T |
| Model | STOE Stadi P with MYTHEN1K Detector |
| Instrument/Software | G.52.SYS.S072/WinXPOW Version 3.0.1.13 GMP |
| Radiation | Cu 40 kV/40 mA; Kalpha1 by bent Ge-Crystal Monochromator; actual Intensity (% relPQ): 104 |
| WL1= | 1.540598 |
| WL2= | 1154443 |
| WLRATI= | 0 |
| Ranges | sf1, DS:1.00°, 12 s; 1.5-50.5°_13 m |
| Drive= | COUPLED |
| STEPTIME= | 12 |
| STEPSIZE= | 0.02 |
| STEPS | 2450 |
| THETA= | 0.75 |
| 2THETA= | 1.5 |
| DIVERGENCE= | 0.09 |
| Rotation (Rps) | 1 |
| DetectorStep (°2T) | 1 |
| Ambient, air | 23 °C; 15 % RH |
| y-shift= | 0 |
| f= | 1 |

Polymorph PM1:

| Angle 2-Theta ° | d value Angstrom | Intensity | Relative intensity % |
|---|---|---|---|
| 3.89 | 22.70 | s | 36.5 |
| 7.96 | 11.10 | m | 24.4 |
| 10.01 | 8.83 | w | 12 |
| 12.00 | 7.37 | w | 12.6 |
| 14.32 | 6.18 | w | 9.8 |
| 16.53 | 5.36 | s | 32.5 |
| 19.09 | 4.65 | m | 15 |
| 22.20 | 4.00 | w | 12 |
| 24.18 | 3.68 | m | 20.1 |

-continued

| Angle 2-Theta ° | d value Angstrom | Intensity | Relative intensity % |
|---|---|---|---|
| 26.10 | 3.41 | m | 15.4 |
| 27.69 | 3.22 | w | 13.6 |

Polymorph PM2:

| Angle 2-Theta ° | d value Angstrom | Intensity | Relative intensity % |
|---|---|---|---|
| 16.96 | 5.23 | vs | 100 |
| 25.28 | 3.52 | vs | 96.5 |
| 11.73 | 7.54 | vs | 83.2 |
| 28.32 | 3.15 | s | 65.9 |
| 25.48 | 3.49 | s | 63.6 |
| 20.10 | 4.41 | s | 62 |
| 26.20 | 3.40 | s | 57.4 |
| 17.63 | 5.03 | s | 54 |
| 24.07 | 3.69 | s | 52.9 |
| 17.18 | 5.16 | s | 50.8 |
| 19.03 | 4.66 | s | 50.5 |
| 22.52 | 3.94 | s | 50.1 |
| 19.73 | 4.50 | s | 47.6 |
| 23.19 | 3.83 | s | 45.5 |
| 21.25 | 4.18 | s | 44.8 |
| 23.72 | 3.75 | s | 44.3 |
| 18.28 | 4.85 | s | 44 |
| 21.55 | 4.12 | s | 37.5 |

-continued

| Angle 2-Theta ° | d value Angstrom | Intensity | Relative intensity % |
|---|---|---|---|
| 20.74 | 4.28 | s | 36.1 |
| 28.89 | 3.09 | s | 33.2 |
| 24.74 | 3.60 | s | 31.3 |
| 30.32 | 2.95 | m | 27.8 |
| 29.21 | 3.05 | m | 27 |
| 26.65 | 3.34 | m | 25.5 |
| 29.68 | 3.01 | m | 25.1 |
| 27.39 | 3.25 | m | 24.7 |
| 35.16 | 2.55 | m | 24.4 |
| 35.70 | 2.51 | m | 22.9 |
| 34.82 | 2.57 | m | 21.5 |
| 36.64 | 2.45 | m | 18.5 |

-continued

| Angle 2-Theta ° | d value Angstrom | Intensity | Relative intensity % |
|---|---|---|---|
| 37.16 | 2.42 | m | 18.1 |
| 37.68 | 2.39 | m | 16.8 |
| 39.01 | 2.31 | m | 16.6 |
| 33.56 | 2.67 | m | 15.6 |
| 41.22 | 2.19 | w | 13.5 |
| 39.99 | 2.25 | w | 12.8 |

Polymorph PM3:

| Angle 2-Theta ° | d value Angstrom | Intensity | Relative intensity % |
|---|---|---|---|
| 14.75 | 6.00 | vs | 100 |
| 10.28 | 8.60 | vs | 93.9 |
| 16.97 | 5.22 | vs | 90.1 |
| 26.55 | 3.35 | vs | 75.2 |
| 18.05 | 4.91 | vs | 74.5 |
| 22.10 | 4.02 | s | 69.2 |
| 27.13 | 3.28 | s | 68.1 |
| 26.11 | 3.41 | s | 60.2 |
| 28.87 | 3.09 | s | 60.1 |
| 19.71 | 4.50 | s | 57.4 |
| 20.74 | 4.28 | s | 55.2 |
| 5.13 | 17.21 | s | 53.9 |
| 26.28 | 3.39 | s | 53.9 |
| 21.68 | 4.10 | s | 52.9 |
| 27.71 | 3.22 | s | 51.3 |
| 25.14 | 3.54 | s | 50.8 |
| 17.84 | 4.97 | s | 50.2 |
| 22.55 | 3.94 | s | 50.2 |
| 23.01 | 3.86 | s | 49.4 |
| 19.29 | 4.60 | s | 49 |
| 28.22 | 3.16 | s | 47.3 |

-continued

| Angle 2-Theta ° | d value Angstrom | Intensity | Relative intensity % |
|---|---|---|---|
| 6.39 | 13.82 | s | 44.3 |
| 15.49 | 5.72 | s | 42.9 |
| 24.54 | 3.62 | s | 37.9 |
| 25.50 | 3.49 | s | 37.3 |
| 10.96 | 8.07 | s | 36.3 |
| 18.94 | 4.68 | s | 36.2 |
| 31.54 | 2.83 | s | 34.8 |
| 23.24 | 3.83 | s | 34.4 |
| 12.81 | 6.91 | s | 33.3 |
| 31.95 | 2,80 | s | 32.8 |
| 29.75 | 3.00 | s | 31.7 |
| 24.79 | 3,59 | m | 28.5 |
| 28.60 | 3.12 | m | 25.2 |
| 35.62 | 2.52 | m | 24.9 |
| 25.81 | 3.45 | m | 24.5 |
| 34.68 | 2.58 | m | 20.4 |
| 38.94 | 2.31 | m | 19.4 |
| 36.58 | 2.45 | m | 19.2 |
| 33.86 | 2.64 | m | 18.8 |
| 38.71 | 2.32 | m | 18.8 |
| 30.19 | 2.96 | m | 17.7 |
| 30.94 | 2.89 | m | 16.9 |
| 31.24 | 2.86 | m | 16.9 |
| 33.28 | 2.69 | m | 16.8 |
| 38.43 | 2.34 | m | 15.9 |
| 33.47 | 2.67 | m | 15.3 |
| 40.87 | 2.21 | m | 15.2 |
| 39.51 | 2.28 | w | 14.7 |
| 30.52 | 2.93 | w | 14.3 |
| 35.39 | 2.53 | w | 13.9 |
| 32.66 | 2.74 | w | 12.9 |
| 38.07 | 2.36 | w | 12.9 |
| 40.53 | 2.22 | w | 11.5 |
| 40.04 | 2.25 | w | 10.7 |

Figure 4:
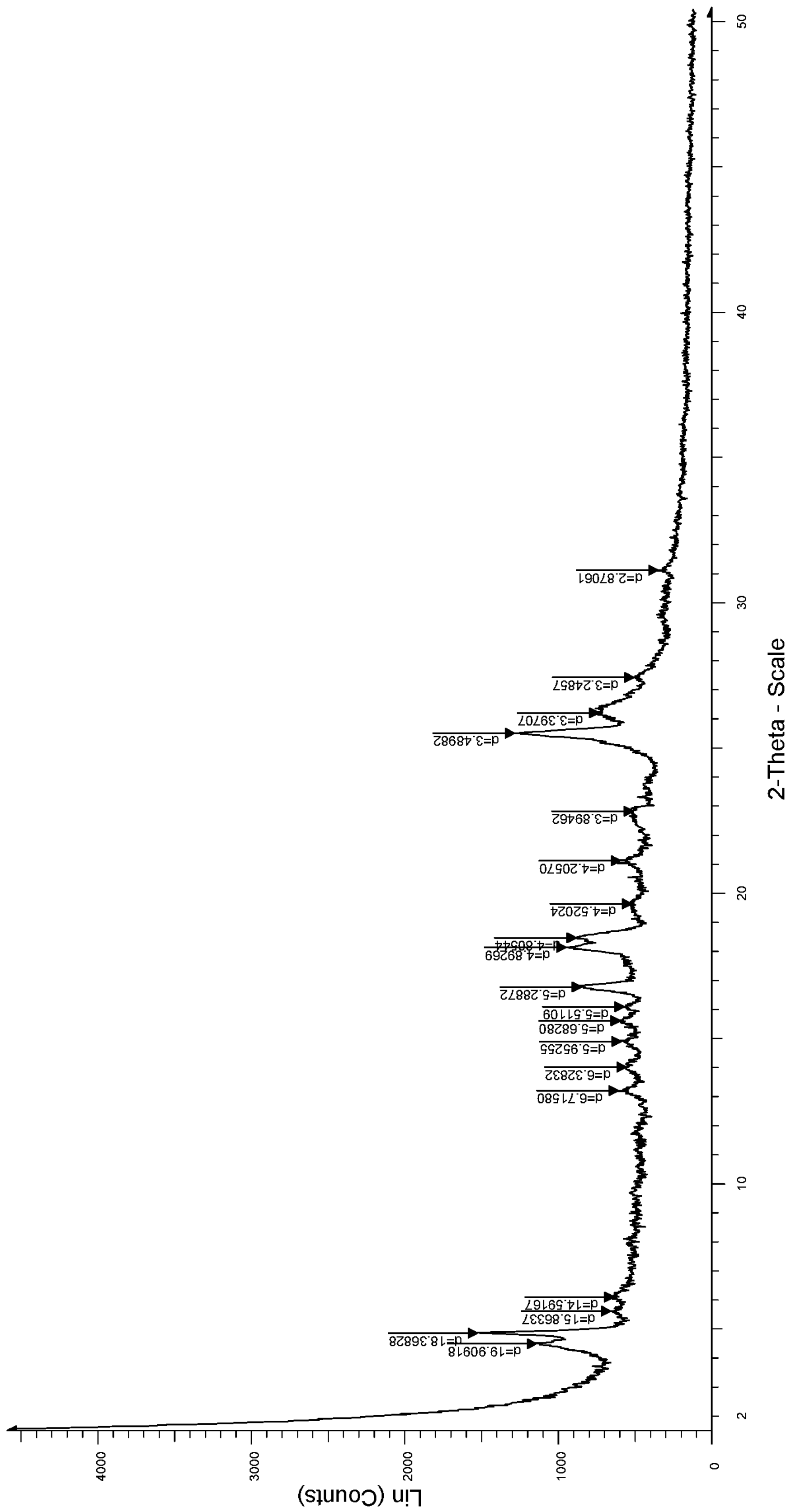
FIG. 4 PXRD pattern of Compound (II) in the form of the $H_2SO_4$ salt

PXRD Conditions—Compound (II) $H_2SO_4$ Salt (FIG. 4)

| | |
|---|---|
| Geometry | Transmission; angular range covered by detector: 12.59° 2T = intrinsic resol. 0.01° 2T |
| Model | STOE Stadi P with MYTHEN1K Detector |
| Instrument/Software | G.52.SYS.S072/WinXPOW Version 3.0.1.13 GMP |
| Radiation | Cu 40 kV/40 mA; Kalpha1 by bent Ge-Crystal Monochromator; actual Intensity (% relPQ): 86 |
| WL1= | 1.540598 |
| WL2= | 1.54443 |
| WLRATIO= | 0 |
| Ranges | sf1, DS:1°, 12 s; 1.500-50.480°_14 m |
| Drive= | COUPLED |
| STEPTIME= | 12 |
| STEPSIZE= | 0.02 |
| STEPS | 2450 |
| THETA= | 0.75 |
| 2THETA= | 1.5 |
| DIVERGENC= | 0.09 |
| Rotation (Rps) | 1 |
| DetectorStep (°2T) | 1 |
| Ambient, air | |

| Angle 2-Theta ° | d value Angstrom | Intensity | Relative intensity % |
|---|---|---|---|
| 4.44 | 19.91 | vs | 74.6 |
| 4.81 | 18.37 | vs | 100 |
| 5.57 | 15.86 | s | 42.9 |
| 6.05 | 14.59 | s | 41.4 |
| 13.17 | 6.72 | s | 39.6 |
| 13.98 | 6.33 | s | 36.2 |
| 14.87 | 5.95 | s | 38.4 |
| 15.58 | 5.68 | s | 38.7 |
| 16.07 | 5.51 | s | 37.1 |
| 16.75 | 5.29 | s | 55.4 |
| 18.12 | 4.89 | s | 62 |
| 18.45 | 4.81 | s | 57.7 |
| 19.62 | 4.52 | s | 33.9 |

-continued

| | | | |
|---|---|---|---|
| 21.11 | 4.21 | s | 38.5 |
| 22.82 | 3.89 | s | 33.2 |
| 25.50 | 3.49 | vs | 84.1 |
| 26.21 | 3.40 | s | 47.9 |
| 27.43 | 3.25 | s | 33 |
| 31.13 | 2.87 | m | 22.5 |

Figure 5:
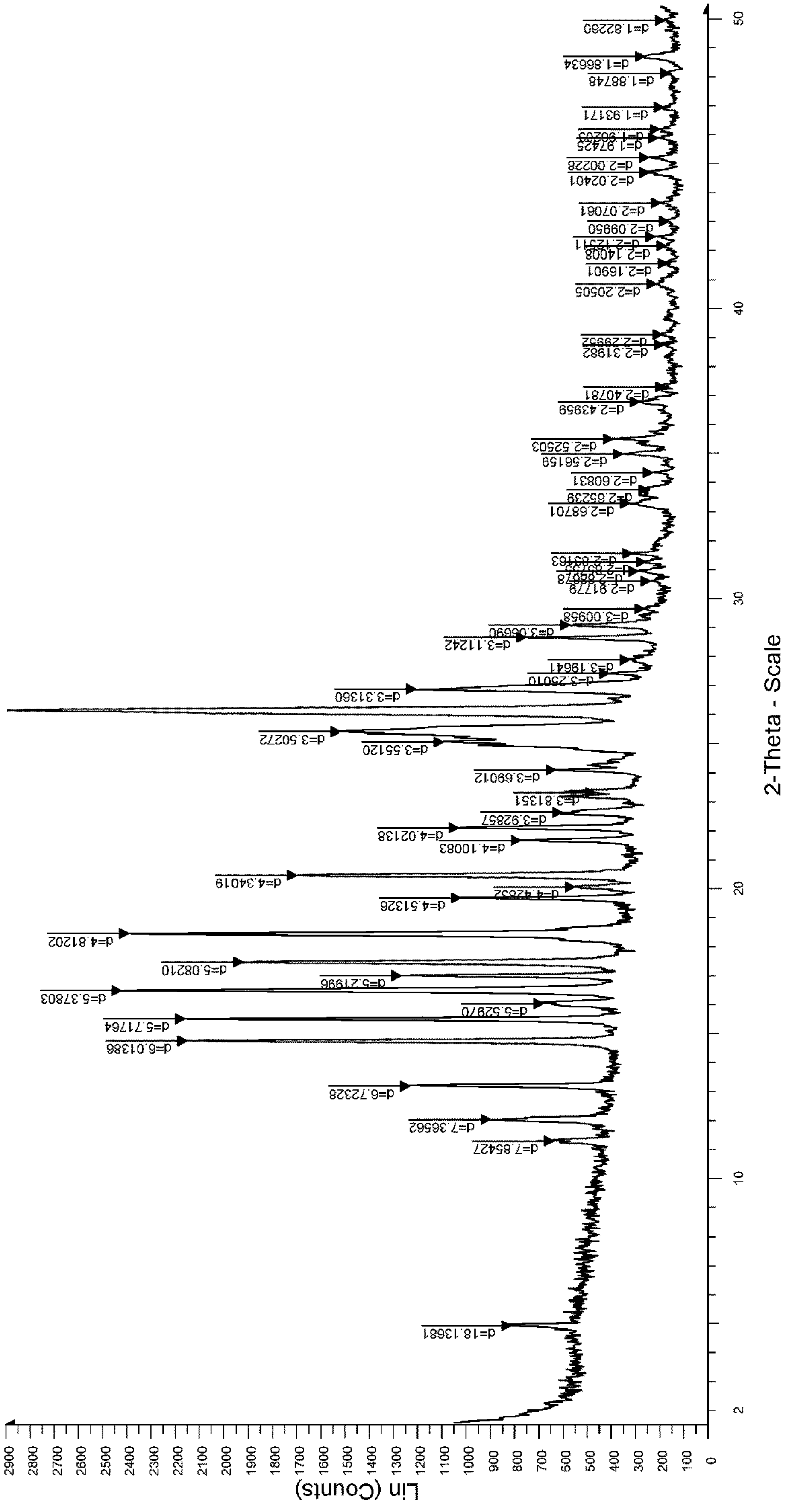
FIG. 5: PXRD pattern of Compound (II) in the form of the $1H_3PO_4$ salt

PXRD Conditions—Compound (II) $H_3PO_4$ Salt (FIG. 5)

| | |
|---|---|
| Geometry | Transmission; angular range covered by detector: 12.59° 2T = intrinsic resol. 0.01° 2T |
| Model | STOE Stadi P with MYTHEN1K Detector |
| Instrument/Software | G.52.SYS.S072/WinXPOW Version 3.0.1.13 GMP |
| Radiation | Cu 40 kV/40 mA; Kalpha1 by bent Ge-Crystal Monochromator; actual Intensity (% relPQ): 95 |
| WL1= | 1.540598 |
| WL2= | 1.54443 |
| WLRATIO= | 0 |
| Ranges | sf1, DS:1°, 12 s; 1.5-50.5°_14 m |
| Drive= | COUPLED |
| STEPTIME= | 12 |
| STEPSIZE= | 0.02 |
| STEPS | 2450 |
| THETA= | 0.75 |
| 2THETA= | 1.5 |
| DIVERGENCE= | 0.09 |
| Rotation (Rps) | 1 |
| DetectorStep (°2T) | 1 |
| Ambient, air | |

| Angle/ 2-Theta ° | d value/ Angstrom | Intensity | Relative intensity [%] |
|---|---|---|---|
| 4.87 | 18.14 | m | 28.1 |
| 11.26 | 7.85 | m | 21.9 |
| 12.01 | 7.37 | s | 31 |
| 13.16 | 6.72 | s | 42.5 |
| 14.72 | 6.01 | vs | 74.3 |
| 15.49 | 5.72 | vs | 74.7 |
| 16.02 | 5.53 | m | 23.4 |
| 16.47 | 5.38 | vs | 83.7 |
| 16.97 | 5.22 | s | 43.7 |
| 17.44 | 5.08 | s | 66.4 |
| 18.42 | 4.81 | vs | 82.7 |
| 19.65 | 4.51 | s | 35.2 |
| 20.04 | 4.43 | m | 18.9 |
| 20.45 | 4.34 | s | 58.7 |
| 21.65 | 4.10 | m | 26.7 |
| 22.09 | 4.02 | s | 35.5 |
| 22.62 | 3.93 | m | 20.8 |
| 23.31 | 3.81 | m | 16 |
| 24.10 | 3.69 | m | 21.7 |
| 25.06 | 3.55 | s | 37.7 |
| 25.41 | 3.50 | s | 52.5 |
| 26.13 | 3.41 | vs | 100 |
| 26.89 | 3.31 | s | 41.6 |
| 27.42 | 3.25 | w | 14 |
| 27.89 | 3.20 | w | 11.1 |
| 28.66 | 3.11 | m | 25.9 |
| 29.09 | 3.07 | m | 19.6 |
| 29.66 | 3.01 | w | 9 |
| 30.62 | 2.92 | w | 8.1 |
| 30.95 | 2.89 | w | 9.9 |
| 31.28 | 2.86 | w | 8.8 |
| 31.57 | 2.83 | w | 10.7 |
| 33.32 | 2.69 | w | 11 |
| 33.77 | 2.65 | w | 8.4 |
| 34.35 | 2.61 | w | 7.8 |
| 35.00 | 2.56 | w | 12 |
| 35.52 | 2.53 | w | 13.5 |
| 36.81 | 2.44 | w | 9.7 |
| 37.32 | 2.41 | w | 6 |
| 38.79 | 2.32 | w | 6.2 |
| 39.14 | 2.30 | w | 6.4 |
| 40.89 | 2.21 | w | 7.2 |

10.3 DSC Measurement

Differential scanning calorimetry is performed in a sealed gold pan with a heating rate of 10° C./min.

10.4 HPLC Determination of Identity, Impurity Profiles and PurityDegree

Identity and assay of the compounds of the present invention base and its impurities are determined by a qualitative and quantitative analysis by high performance liquid chromatography (HPLC) with diode array detection using an in-house method based on Ph. Eur. 2.2.29.

Identity of the synthesized compounds is confirmed by comparison to the retention times and spectra of the corresponding reference substances. Assay is calculated based on an external calibration curve of the tested compound in the form of the base for both the salt form and its impurities.

Procedure

Apparatus

HPLC equipped with a pump, autosampler, column oven and diode array detector, and analytical balance (Category 1), pipettes (e.g. Gilson, Rainin), volumetric flasks (10, 25 and 50 ml), membrane filter (0.2 μm)

Reagents methanol (HPLC grade), Sigma (or equivalent)

trifluoroacetic acid (TFA) for HPLC 100%, Sigma (or equivalent)

Mobile Phase:

A: water/methanol (95+5 V/V; 0.1% TFA)

B: methanol/water (95+5 V/V; 0.1% TFA)

Mobile Phase A: Water/Methanol (95+5 V/V; 0.1% TFA)

Dilute 100 ml methanol to 2 liters with water R. Add 2.0 ml TFA then, mix thoroughly and degas in the ultrasonic bath.

Mobile Phase B: Methanol/Water (95+5 V/V; 0.1% TFA)

Dilute 50 ml water R to 1 liter with methanol. Add 1.0 ml TFA then, mix thoroughly and degas in the ultrasonic bath.

Stock solutions A and B (1000 mg/l): Prepare two stock solutions each of 1,000 mg/L of the compound to be tested, by dissolving 50 mg in 50 mL of mobile phase A.

Standard solutions A and B (40 mg/l): Dilute each of the stock solutions 1:25 with mobile phase A. Filter the samples through a 0.2 μm filter into the HPLC glass vial.

SST Stock Solution

Weigh 10 mg of reference impurities, e.g. the intermediate compounds to be expected from the process, into a 10 ml volumetric flask, add 5 ml of methanol and dilute with water.

Impurity Solution C (1 mg/l)

Pipette 100 μl of stock solution A into a 100 ml volumetric flask and dilute with mobile phase A.

Filter the samples through a 0.2 μm filter into the HPLC glass vial.

Impurity Solution D/SST Standard Solution (10 mg/l)

Pipette 1000 μl of stock solution B and 1000 μl of SST stock solution into a 100 ml volumetric flask and dilute with mobile phase A. Filter the samples through a 0.2 μm filter into the HPLC glass vial.

Chromatographic System

The liquid chromatograph is equipped with a column compartment maintained at a controlled temperature of 40° C.±5° C., a diode array detector (200-400 nm) and a 4.6 mm×150 mm C18 column (e.g. Ascentis Express C18, 2.7 μm). The flow rate is at 1.0 ml/min.

LC Gradient:

| time [min] | A [%] | B [%] |
|---|---|---|
| −3.000 | 100 | 0 |
| 0.000 | 100 | 0 |
| 1.000 | 100 | 0 |
| 8.000 | 65 | 35 |
| 20.000 | 65 | 35 |
| 20.100 | 0 | 100 |
| 25.000 | 0 | 100 |

Run time: 20.0 min
UV wavelength: 254 nm
injection volume: 10 μl for samples, variable volumes for standard solutions System Suitability Testing (SST) and Quality Control Check (QC)

Adequate injections of SST standard solution prove the suitability of the chromatographic system if the RSD and retention times of the tested compound peak areas is ≤2%, respectively, resolution of the tested compound is ≥1.5 and the tailing factor of the tested compound peak is in the range 0.8-1.5.

Inject standard solution A six times at the beginning of the sequence (SST) and twice at the end of sequence (QC). The sequence may only be used if the requirements above are fulfilled.

Standard Curve

The standard curve for the tested compound (assay) may be obtained by e.g., injecting 5.0 μL, 7.5 μL and 10.0 μL of standard solution A and 12.5 μL and 15.0 μL of standard solution B.

The standard curve for the tested compound impurities may be obtained by e.g., injecting 5.0 μL and 10.0 μL of impurity solution C and 5.0 μl, 10.0 μL and 15.0 μL of impurity solution D.

The regression coefficient for both standard curves should be ≥0.9990.

Sample Preparation

Procedure—Impurities

Weigh accurately approximately 50 mg of the compound to be tested in its salt form into a 50-ml-flask and make up to the mark with mobile phase A. Prepare the sample solution twice. Filter the solution through a 0.2 μm membrane filter and inject 10 μl.

Procedure—Assay

Use both solutions prepared for 'Impurities' and dilute 1:25 with mobile phase A. Filter the solution through a 0.2 μm membrane filter and inject 10 μl.

Calculation

Qualitative Determination

The retention time of the tested compound should not deviate more than 0.3 min from the peak of standard A solution. The spectrum obtained for the tested compound in the sample correlates with the reference spectrum of the tested compound in the standard A solution. Determine the library match factor. The latter should be ≥990.

The retention time of any impurity of the tested compound should not deviate more than 0.1 min from the corresponding reference substance. The spectrum obtained for the impurity in the sample correlates with the reference spectrum of the corresponding impurity in the SST solution. Determine the library match factor. The latter should be ≥990.

Quantitative Determination—Assay

Plot the concentrations of the standard solutions expressed in amount of the tested compound in the form of its base (μg) versus the peak area and extract the intercept (a) and the slope (b). The correlation coefficient obtained should not be less than 0.999. Calculate the amount of the tested compound base using the below formula:

$$\text{Tested Compound Base } [\% \ (m/m)] = \frac{(y-a)\cdot V_1 \cdot V_2 \cdot 100}{b \cdot V_3 \cdot E}$$

y peak area (tested compound) of the sample
a intercept of the standard curve
b slope of the standard curve (area/μg)
$V_1$ dilution (e.g., 50 mL)
$V_2$ dilution factor volume of the sample (e.g., 1.0 ml/25 ml=25)
$V_3$ injection volume (e.g. 10 μl)
E amount of sample weighed (mg)
100 factor to calculate % [m/m]

Quantitative Determination—Impurities

Quantitative Determination of Impurities as % Area

All peaks in the sample chromatogram at 254 nm are integrated. Peaks related to the blank are not considered. The percentage of total impurities and each single impurity ≥0.05% area is determined and reported.

Quantitative Determination of Impurities as % m/m

The concentrations of the standard solutions expressed in amount of the tested compound in the form of its base (μg) are plotted versus the peak area and the intercept (a) and the slope (b) are extracted. The correlation coefficient obtained should not be less than 0.999. The amount of each impurity is calculated taking into consideration the response factor using the below formula:

$$\text{impurity } (\% \ [m/m]) = \frac{(y-a)\cdot V_1 \cdot 100}{b \cdot V_2 \cdot E \cdot RF}$$

y peak area (tested compound) of the sample
a intercept of the standard curve
b slope of the standard curve (area/μg)
$V_1$ dilution (e.g., 50 mL)
$V_2$ injection volume (e.g. 10 μl)
E amount of sample weighed (mg)
100 factor to calculate % [m/m]
RF Response Factor of each impurity vs. the tested compound The above method is used to determine identity and assay the Compound (II) in the form a 3HCl salt (polymorph PM1) prepared with the process according to Example 4 (Process Variant 1 and 2).

| Abbreviation | Name | Sum formula/ Molecular weight | structure |
|---|---|---|---|
| RM-2-a = RM2 = SP6 | (3-fluoropyridin-2-yl)methanamine | $C_6H_7FN_2$ Mw: 126.13 g/mol | 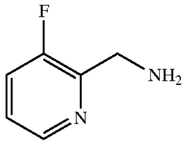 |
| RM-2-a' | 2-(Aminomethyl)-3-bromopyridine | Mw: 259.96 g/mol | 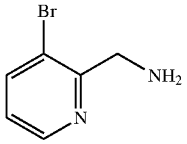 |
| RM-3-a = RM3 | 2-(1H-benzo[d]imidazol-2-yl)ethan-1-amine | $C_9H_{11}N_3$ Mw: 161.21 g/mol | 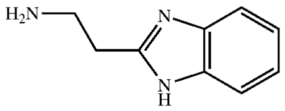 [SMILES: NCCc1nc2ccccc2[nH]1] |
| IM-2-a | 2-Vinyloxazole-4 carboxylic acid | Mw: 139.11 g/mol | 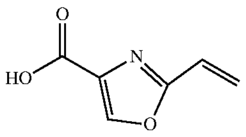 |
| IM-3-b = IM2 | N-((3-fluoropyridin-2-yl)methyl)-2-vinyloxazole-4-carboxamide | $C_{12}H_{10}FN_3O_2$ Mw: 247.23 g/mol | 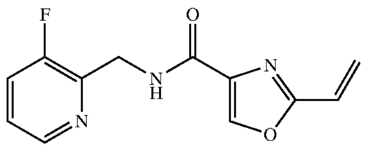 [SMILES: C=Cc1nc(C(=O)NCc2ncccc2F)co1] |
| IM-3-b' | N-((3-bromopyridin-2-yl)methyl)-2-vinyloxazole-4-carboxamide | $C_{12}H_{10}BrN_3O_2$ Mw: 308.14 g/mol | 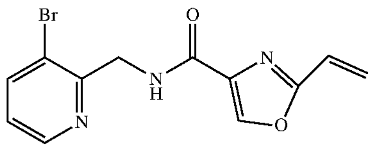 [SMILES: C=Cc1nc(C(=O)NCc2ncccc2Br)co1] |

-continued

| Abbreviation | Name | Sum formula/ Molecular weight | structure |
| --- | --- | --- | --- |
| SP1 | 2-(2-((2-(1H-benzo[d]imidazol-2-yl)ethyl)amino)ethyl)-N-(pyridin-2-ylmethyl)oxazole-4-carboxamide | $C_{21}H_{22}N_6O_2$ Mw: 390.45 g/mol | 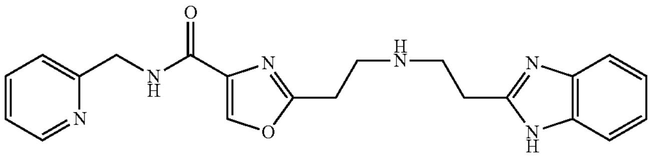 [SMILES: O=C(NCc1ccccn1)c1coc(CCNCCc2nc3ccccc3[nH]2)n1] |
| SP3 | N-((3-fluoropyridin-2-yl)methyl)-2-(2-((2-(1-(2-(4-(((3-fluoropyridin-2-yl)methyl)carbamoyl)oxazol-2-yl)ethyl)-1H-benzo[d]imidazol-2-yl)ethyl)amino)ethyl)oxazole-4-carboxamide | $C_{33}H_{31}F_2N_9O_4$ Mw: 655.67 g/mol | 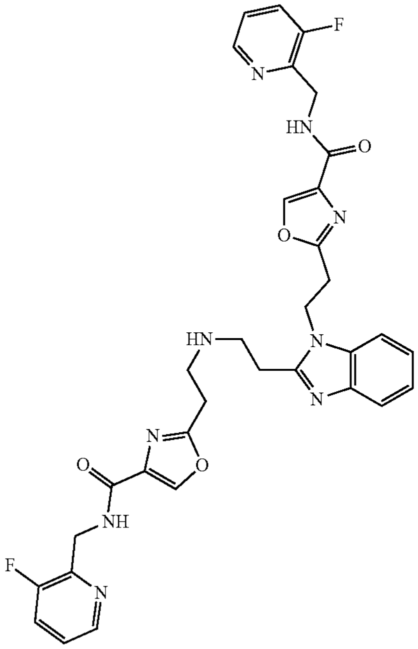 [SMILES: O=C(NCc1ncccc1F)c1coc(CCNCCc2nc3ccccc3n2CCc2nc(C(=O)NCc3ncccc3F)co2)n1] |
| SP4 | 2,2'-(((2-(1H-benzo[d]imidazol-2-yl)ethyl)azanediyl)bis(ethane-2,1-diyl)) bis (N-((3-fluoropyridin-2-yl)methyl)oxazole-4-carboxamide) | $C_{33}H_{31}F_2N_9O_4$ Mw: 655.67 g/mol | 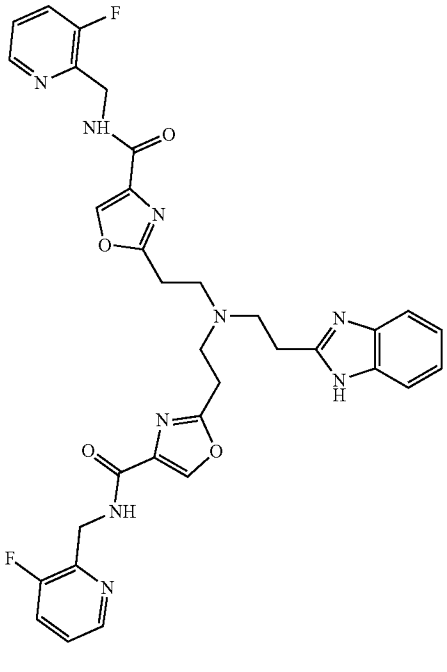 [SMILES: O=C(NCc1ncccc1F)c1coc(CCN(CCc2nc3ccccc3[nH]2)CCc2nc(C(=O)NCc3ncccc3F)co2)n1] |

-continued

| Abbreviation | Name | Sum formula/ Molecular weight | structure |
|---|---|---|---|
| SP5 | 3-((2-(1H-benzo[d]imidazol-2-yl)ethyl)amino)propanoic acid | $C_{12}H_{15}N_3O_2$ Mw: 233.27 g/mol | 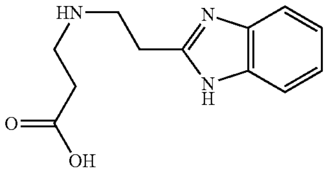 [SMILES: O=C(O)CCNCCc1nc2ccccc2[nH]1] |
| SP7 | 2-(2-aminoethyl)-N-((3-fluoropyridin-2-yl)methyl)oxazole-4-carboxamide | $C_{12}H_{13}FN_4O_2$ Mw: 264.26 g/mol | 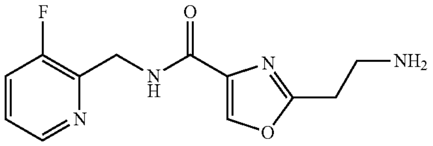 [SMILES: NCCc1nc(C(=O)NCc2ncccc2F)co1] |

| Reference standards | Information | Storage |
|---|---|---|
| Compound (II) 3HCl (VIT-2763) | Content is based on free base with a content of 75.3% | RT |
| RM-2-a = RM2 = SP6 | see response factor, 6.4 | +2 − +8 °C |
| RM-3-a = RM3 | see response factor, 6.4 | +2 − +8 °C |
| IM-3-b = IM2 | — | RT |
| SP1 | see response factor, 6.4 | RT |
| SP3 | see response factor, 6.4 | RT |
| SP4 | see response factor, 6.4 | RT |
| SP5 | see response factor, 6.4 | RT |
| SP7 | see response factor, 6.4 | RT |

| Impurity | Response Factor |
|---|---|
| RM-2-a = RM2 = SP6 | 1.140 |
| RM-3-a = RM3 | 1.269 |
| SP1 | 1.300 |
| SP3 | 0.916 |
| SP4 | 0.884 |
| SP5 | 0.889 |
| SP7 | 0.748 |

Results:

| Substance | Retention Time [min] |
|---|---|
| RM-2-a = RM2 = SP6 | 2.30 |
| RM-3-a = RM3 | 3.71 |
| SP5 | 4.05 |
| SP7 | 5.34 |
| SP1 | 5.81 |
| Compound (II) 3HCl (VIT-2763) | 8.33 |
| IM-3-b = IM2 | 10.84 |
| SP3 | 12.08 |
| SP4 | 13.97 |

FIG. 6 shows the HPLC chromatogram of the impurity profile of a Compound (II) 3HCl salt (polymorph PM1/VIT-2763) prepared with the process according to Example 4 followed by solvent extraction (Process Variant 1)

| No. | Rel. RT [VIT-2763] | Peak Name | Height mAU | Area mAU * min | Name in Library | Match in Library | rel. Area % |
|---|---|---|---|---|---|---|---|
| 1 | 0.48 | RM3 | 0.593 | 0.05964 | SP5 | 946.91 | 0.06 |
| 2 | 1.00 | VIT-2763 | 950.122 | 104.71023 | n.a. | n.a. | 99.75 |
| 3 | 1.27 | unknown | 0.593 | 0.08638 | VIT-2763 | 809.42 | 0.08 |
| 4 | 1.48 | SP3 | 0.640 | 0.11859 | SP3 | 852.54 | 0.11 |

FIG. 7 shows the HPLC chromatogram of the impurity profile of a Compound (II) 3HCl salt (polymorph PM1/VIT-2763) prepared with the process according to Example 4 followed by oil separation (Process Variant 2)

| No. | Rel. RT [VIT-2763] | Peak Name | Height mAU | Area mAU * min | Name in Library | Match in Library | rel. Area % |
|---|---|---|---|---|---|---|---|
| 1 | 0.70 | SP1 | 1.287 | 0.06175 | SP1 | 956.88 | 0.058 |
| 2 | 1.00 | VIT-2763 | 1101.520 | 107.10545 | n.a. | n.a. | 99.861 |
| 3 | 1.27 | SP2 | 1.575 | 0.08782 | VIT-2763 | 949.55 | 0.082 |

Figure 8:
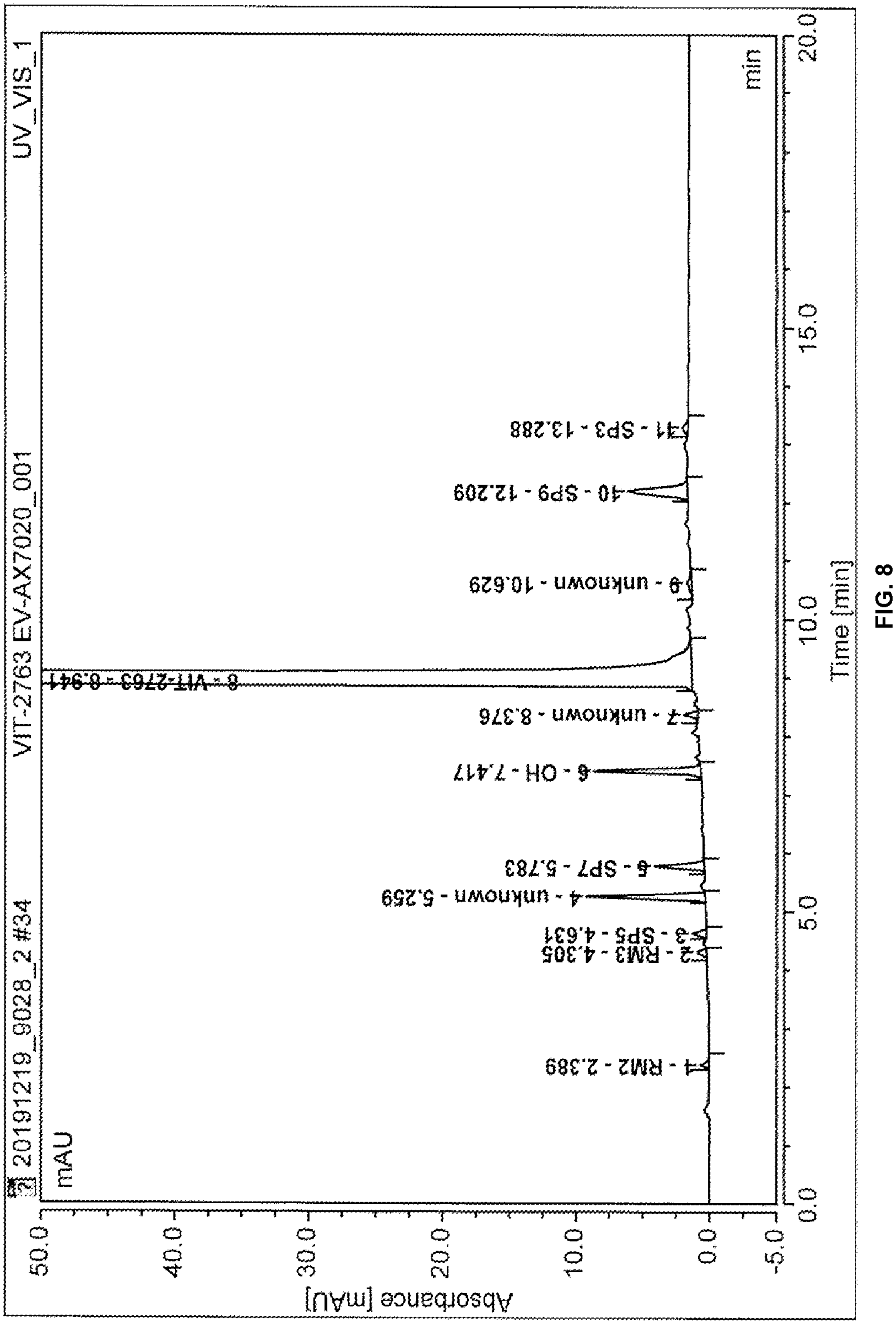
FIG. 8: HPLC Chromatogram showing the impurity profile of a Compound (II) 3HCl salt (polymorph PM1) obtainable with the process described in WO2017068090A1 (Preparation of Example Compound No. 127)

Comparative Example—Example Compound 127 According to WO2017068090A1:

FIG. 8 shows the HPLC chromatogram of the impurity profile of a Compound (II) 3HCl salt (polymorph PM1/VIT-2763) obtainable with the process described in WO2017068090A1 (Preparation of Example Compound No. 127)

| No. | Rel. RT [VIT-2763] | Peak Name | Height mAU | Area mAU * min | Name in Library | Match in Library | rel. Area % |
|---|---|---|---|---|---|---|---|
| 1 | 0.27 | RM2 | 0.649 | 0.05274 | n.a. | n.a. | 0.05 |
| 2 | 0.48 | RM3 | 0.714 | 0.06292 | SP5 | 963.18 | 0.06 |
| 3 | 0.52 | SP5 | 1.029 | 0.08730 | SP5 | 984.98 | 0.08 |
| 4 | 0.59 | unknown | 8.853 | 0.65997 | VIT-2763 | 948.21 | 0.63 |
| 5 | 0.65 | SP7 | 3.709 | 0.29642 | SP7 | 993.82 | 0.28 |
| 6 | 0.83 | OH | 7.957 | 0.59178 | VIT-2763 | 942.23 | 0.57 |
| 7 | 0.94 | unknown | 1.012 | 0.07481 | VIT-2763 | 914.21 | 0.07 |
| 8 | 1.00 | VIT-2763 | 949.837 | 102.08108 | VIT-2763 | 837.49 | 97.52 |
| 9 | 1.19 | unknown | 0.375 | 0.07308 | n.a. | n.a. | 0.07 |
| 10 | 1.37 | SP9 | 4.466 | 0.63416 | SP9 0.50% | 944.14 | 0.61 |
| 11 | 1.49 | SP3 | 0.376 | 0.06125 | n.a. | n.a. | 0.06 |

Conversion from Compound (II) Base to Compound (II) in 3HCl $$VIT\text{-}2763\text{-}3HCl[\%\ (m/m)]=VIT\text{-}2763\text{ base }[\%\ (m/m)]\times 517.81\ [g/mol]/408.44\ [g/mol]$$

This corresponds to a conversion factor of 1.27.

11. Pharmacological Assays for Evaluation of the Activity of Compounds (II) and (II')

The following table summarizes the activity of the compounds (II) and (II') as ferroportin inhibitors compared to hepcidin:

| Assay | (II') IC50 (nM) | (II) IC50 (nM) | Hepcidin IC50 (nM) | n |
|---|---|---|---|---|
| Hepcidin internalization (J774) | 5.9 | 7.3 | 10.7 | 2 |
| Biophysical Ferroportin-Hepcidin Binding (FP) | 28 | 28 | — | 2 |
| Iron response (HEK354 Blazer) | 168 | 156 | 39 | 3 |
| Fpn internalization and degradation (HEK354 FACS) | 161 | 119 | 6 | 2 |

Compounds (II) and (II') were tested in the form of their 3HCl-salts.

11.1 Hepcidin Internalization Assay (J774)

This cellular assay allows quantification of the binding of hepcidin to ferroportin (Fpn) through microscopic detection of internalization of a fluorescently labeled hepcidin into J774 cells. J774 is a mouse macrophage cell line which was shown to express Fpn endogenously upon incubation with iron (Knutson et al, 2005). Binding of hepcidin to Fpn triggers internalization and degradation of both hepcidin and Fpn. However, the TMR (6-carboxytetramethylrhodamine) fluorophore attached to hepcidin remains associated with the cell after degradation of the hepcidin peptide backbone. Therefore, microscopic detection of cell-associated TMR fluorescence is a measure of hepcidin binding to Fpn and internalization of hepcidin and Fpn. If TMR-hepcidin is prevented from binding to Fpn, cellular TMR fluorescence remains low (Dürrenberger et al, 2013). The effect of small molecular weight Fpn inhibitor compounds in this assay was evaluated in vitro as described below.

J774 cells, harvested from ca. 80% confluent cultures, were plated at $8\times10^5$ cells/ml in complete medium (DMEM, 10% FBS, 1% Penicillin-Streptomycin) containing 200 μM Fe(III)NTA (nitrilotriacetic acid), 100 μl per well of 96 well MicroClear plates (Greiner; Cat. 655090) and grown at 37° C. with 5% $CO_2$. After overnight incubation, cells were washed 3 times with pre-warmed DMEM w/o phenol red, 30 μl/well of DMEM w/o phenol red was added after the final wash and 10 μl/well of dilution series of test compounds were added in triplicates. J774 cells were pre-incubated with test compounds at 37° C. with 5% $CO_2$ for 15 min. before TMR-hepcidin was added at 25 nM final concentration. Cells were incubated in a total volume of 50 μl at 37° C. with 5% $CO_2$ for 2 hours, then Hoechst 33342 dye was added to a final concentration of 0.5 μg/ml to stain nuclei and further incubated for 10 min. at 37° C. with 5% $CO_2$. Cells were washed 3 times with PBS and fixed in 100 μl of 4% paraformaldehyde in PBS for 15 min. at room temperature. After removal of the paraformaldehyde solution, cells were washed 3 times with PBS leaving 100 μl per well and the plates were sealed with foil plate seal. TMR (530-550 nm excitation/575-625 nm emission/400 ms exposure time) and Hoechst 33342 (360-370 nm excitation/420-460 nm emission/10 ms exposure time) fluorescence images were acquired using a ScanR plate imager (Olympus) with a 20× high NA objective. Four pictures were acquired per well and fluorescence channel covering ca. 1500 cells per well. The acquired image data was analysed with the ScanR image analysis software. Image analysis included detection of nuclei (Hoechst 33342 fluorescence), identification of cell-associated regions, application of a virtual channel and thresholding for rolling-ball-type background reduction, followed by application of the Sum (Mean) algorithm to measure the TMR fluorescence associated with cells as a quantitative measure for internalized TMR-hepcidin. $IC_{50}$ values were calculated with the Sum (Mean) raw data using "log (inhibitor) vs. response" curve fitting of Prism 5 software (GraphPad Software Inc., version 5.02). For each data set the fit of the "log (inhibitor) vs. response (three parameters)" model was compared to the fit of the "log (inhibitor) vs. response—Variable slope (four parameters)" model and the $IC_{50}$ data of the preferred model was used. $IC_{50}$ data of the Compounds according to formula (II) and (II'), that were tested in the hepcidin internalization assay are shown in Table 1. The $IC_{50}$ of unlabeled hepcidin in this assay is 0.015±0.011 μM.

TABLE 1

| Average (AVE) $IC_{50}$ data of Compounds (II) and (II') tested in the hepcidin internalization assay is shown for multiple measurements | |
|---|---|
| Exp. Comp. | J774 IC50 (uM) |
| Compound (II') | 0.006 |
| Compound (II) | 0.007 |

11.2 Biophysical Ferroportin-Hepcidin Binding Assay

This biophysical assay was developed to confirm inhibition of hepcidin binding to ferroportin (Fpn) more directly. Incubation of TMR-hepcidin with purified human Fpn isolated from *Pichia pastoris* yeast cells expressing human Fpn with a C-terminal FLAG affinity tag (Bonaccorsi di Patti, 2014) leads to increased fluorescence polarization (FP) of the TMR-hepcidin ligand. Compounds (II) and (II') were tested for inhibition of binding of TMR-hepcidin to Fpn, as detected by dose-dependent decrease of the TMR FP signal, as described in detail below.

A mixture of 1.3 mM human Fpn and 30 nM TMR-hepcidin in FP assay buffer containing 50 mM Tris-HCl pH 7.3, 200 mM NaCl, 0.02% DDM, 0.1% BSA was plated into a 384 well black low volume round bottom plate (Corning, Cat. 3677) at 16 ml per well. 8 ml of serial dilutions of test compounds were added in duplicates to reach final Fpn and TMR-hepcidin concentrations of 1 mM and 20 nM, respectively. Plates were incubated for 90 minutes at room temperature and parallel(S) and perpendicular (P) fluorescence was measured in a Synergy H1 fluorescence reader (BioTek). FP values were calculated in mP according to the following formula.

$$mP = \frac{F_{parallel} - F_{perpendicular}}{F_{parallel} + F_{perpendicular}} \times 1000$$

$IC_{50}$ values were determined with the calculated mP values as described for the hepcidin internalization assay and are listed in Table 2. The $IC_{50}$ of unlabeled hepcidin in this assay is 0.37±0.067 μM.

TABLE 2

| Average (AVE) $IC_{50}$ data of Compounds (II) and (II') tested in the biophysical hepcidin-ferroportin binding assay is shown for multiple measurements. | |
|---|---|
| Exp. Comp. | FP IC50 (uM) |
| Compound (II') | 0.028 |
| Compound (II) | 0.028 |

11.3 Inhibition of Ferroportin mediated Iron Export Activity in an Iron Response Assay Intracellular iron levels are indirectly measured in this assay by monitoring the activity of a beta-lactamase (BLA) reporter gene fused to the human ferritin promoter and the associated iron regulatory element (IRE) contained within the 5' untranslated region of the ferritin mRNA. Expression of ferroportin (Fpn) in such a cell line leads to iron efflux and lower iron levels as reflected by lower activity of the reporter gene. On the other hand, inhibition of Fpn-mediated iron efflux results in elevated cellular iron levels which is detected as increased reporter gene activity. Small molecular weight Fpn inhibitor compounds were tested for dose-dependent effects in this in vitro iron response assay as described below.

The HEK-293 cell line #354 was generated by stable integration of (i) a human Fpn-GFP fusion construct inserted in a derivative of the doxycycline-inducible pTRE-Tight-BI plasmid (Clontech, Cat. 631068) and (ii) a human ferritin promoter-BLA reporter gene into a derivative of the HEK-293 Tet-ON Advanced cell line (Clontech). To generate the ferritin-BLA reporter gene construct, a 1.4 kb fragment of the human ferritin H promoter was amplified by PCR from human genomic DNA (forward primer 5'-CAGGTTTGT-GAGCATCCTGAA-3'; reverse primer 5'-GGCGGCGACTAAGGAGAGG-3') and inserted in front of the BLA gene present in the pcDNA™6.2/cGeneBLAzer™-DEST plasmid (Invitrogen, Cat. 12578-043) thereby replacing the original CMV promoter and placing the IRE that regulates translation of the ferritin gene ca. 170 bp upstream of the start codon of the reporter gene. #354 cells were harvested from ca. 80% confluent cultures, seeded at $1.8\times10^5$ cells/ml in DMEM/F12 GlutaMAX™ medium (Invitrogen, Cat. 31331-028) containing 10% FBS (Clontech, Cat. 631106), 1% Penicillin-Streptomycin, 200 μg/ml Hygromycin B (Invitrogen, Cat. 10687-010), Blasticidin 5 μg/ml, (Invitrogen, Cat. R210-01), 4 μg/ml doxycycline (Clontech, Cat. 631311), 50 μl per well of 384 well PDL-coated plates and grown at 37° C. with 5% $CO_2$. After overnight incubation, 10 μl/well of dilution series of the test compounds were added in quadruplicates and plates were further incubated overnight at 37° C. with 5% $CO_2$. Cells were washed 3 times with HBSS leaving 25 μl per well. BLA activity was detected by adding 5 μl/well of the GeneBlazer reagent CCF4-AM (Invitrogen, Cat. K1085) to the cells. After incubation of the plates in the dark at 18° C. for 60 min., blue and green fluorescence signals were measured in a Safire2 fluorescence plate reader (Tecan) with excitation at 410 nm and emissions at 458 nm (blue) and 522 nm (green). The ratio of blue/green fluorescence as a measure for BLA activity was calculated and $EC_{50}$ values were determined with the calculated blue/green fluorescence ratios as described for the hepcidin internalization assay. The $EC_{50}$ data of the tested Compounds (II) and (II') are listed in Table 3. The $EC_{50}$ of hepcidin in this assay is 0.096±0.063 μM (n=37).

TABLE 3

| Average (AVE) $EC_{50}$ data of Compounds (II) and (II') tested in the iron response assay is shown for multiple measurements. | |
|---|---|
| Exp. Comp. | BLAzer EC50 (uM) |
| Compound (II') | 0.168 |
| Compound (II) | 0.156 |

11.4 Ferroportin Internalization and Degradation Assay

HEK-293 cell line #354 (described in 11.3) was used to measure the capacity of the compounds to induce internalization and degradation of ferroportin (Fpn) by fluorescence activated cell sorting (FACS). Growing HEK-293 #354 cells in doxycycline containing media induced expression of human Fpn-GFP fusion protein on the cell surface. Data from 10 independent experiments showed that cultivation of HEK #354 cells for 48 h in the presence of 4 μg/ml doxycycline induced in average 42.6%±6.4% Fpn-GFP-positive cells. Small molecular weight Fpn inhibitor compounds were tested for dose-dependent effects on the Fpn-GFP mean fluorescence intensity (MFI) on HEK-293 cell line #354, as described below.

HEK #354 cells were harvested from ca. 80% confluent cultures, seeded at $0.6\times10^6$ cells/ml in DMEM/F12 GlutaMAX™ medium (Invitrogen, Cat. 31331-028) containing 10% FBS (Clontech, Cat. 631106), 1% Penicillin-Streptomycin (Invitrogen, Cat. 15140-122), 200 μg/ml Hygromycin B (Invitrogen, Cat. 10687-010), Blasticidin 5 μg/ml, (Invitrogen, Cat. R210-01), 4 μg/ml doxycycline (Clontech, Cat. 631311), 50 μl per well of 384 well plates (Greiner; Cat. 781091) and grown at 37° C. with 5% $CO_2$. After overnight incubation, 10 μl/well of dilution series of the test compounds were added in quadruplicates and plates were further incubated overnight at 37° C. with 5% $CO_2$. Cells were washed once with FACS buffer (PBS containing 1% FBS, 2 mM EDTA and 0.05% $NaN_3$), harvested in FACS buffer with 0.5 μg/ml propidium iodide (Sigma, Cat. P4864) and analyzed in a flow cytometer (CANTO™ II, BD Biosciences) equipped with high throughput sampler. Live HEK #354 cells were gated as propidium iodide negative population and analyzed for expression of Fpn-GFP. MFI of Fpn-GFP of >2000 live cells for each compound dilution was calculated using FlowJo (Tree Star's, Oregon) and the potency of the Fpn-inhibitors to induce internalization and degradation of Fpn-GFP was calculated as described for the hepcidin internalization assay. $EC_{50}$ data of the Compounds (II) and (II') tested in the ferroportin internalization and degradation assay by FACS are listed in Table 4. The average $EC_{50}$ value of hepcidin in this assay is 0.004±0.002 μM.

TABLE 4

Average (AVE) $EC_{50}$ data of Compounds (II) and (II') tested in the ferroportin internalization and degradation assay is shown for multiple measurements.

| Exp. Comp. | EC50 (uM) |
|---|---|
| Compound (II') | 0.161 |
| Compound (II) | 0.119 |

The invention claimed is:

1. A process for preparing a compound of formula (I) or a pharmaceutically acceptable salt thereof (I)

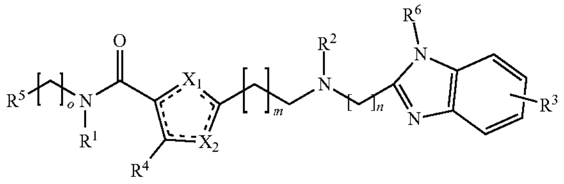

comprising at least one step comprising reacting a compound of formula (IM-3) with a compound of formula (RM-3)

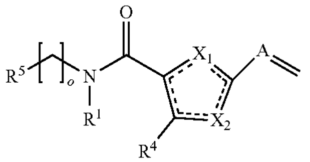

(IM-3)

+

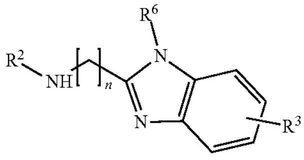

(RM-3)

to provide the compound of formula (I), wherein:

$X^1$ is N, S or O, and $X^2$ is N, S or O, with the proviso that one of $X^1$ and $X^2$ is N and that $X^1$ and $X^2$ are different;

m is an integer of 1, 2, or 3;

n is an integer of 1, 2, 3 or 4;

SEQUENCE LISTING

<160> NUMBER OF SEQ ID NOS: 2

<210> SEQ ID NO 1
<211> LENGTH: 21
<212> TYPE: DNA
<213> ORGANISM: human
<220> FEATURE:
<223> OTHER INFORMATION: forward primer

<400> SEQUENCE: 1
caggtttgtg agcatcctga a 21

<210> SEQ ID NO 2
<211> LENGTH: 19
<212> TYPE: DNA
<213> ORGANISM: human
<220> FEATURE:
<223> OTHER INFORMATION: reverse primer

<400> SEQUENCE: 2
ggcggcgact aaggagagg 19 o is an integer of 1, 2, 3 or 4;

A represents a CH-group, a $CH_2$—CH-group, or a $CH_2$—$CH_2$—CH-group;

$R^1$ and $R^2$ are independently selected from the group consisting of hydrogen and $C_1$-$C_4$-alkyl optionally substituted with 1 or 2 substituents;

$R^3$ represents hydrogen or 1, 2 or 3 optional substituents independently selected from the group consisting of halogen, cyano, $C_1$-$C_4$-alkyl, $C_1$-$C_3$-halogenoalkyl, $C_1$-$C_4$-alkoxy, and a carboxyl group;

$R^4$ is selected from the group consisting of hydrogen, halogen, $C_1$-$C_3$-alkyl, and $C_1$-$C_3$-halogenoalkyl;

$R^5$ is selected from the group consisting of aryl optionally substituted with 1 to 3 substituents, and mono- or bicyclic heteroaryl optionally substituted with 1 to 3 substituents; and $R^6$ is selected from the group consisting of hydrogen, halogen, $C_1$-$C_4$-alkyl optionally substituted with 1 or 2 substituents, and $C_1$-$C_3$-halogenoalkyl.

2. The process of claim 1, further comprising a step of reacting a compound of formula (IM-2) with a compound of formula (RM-2) to form the compound of formula (IM-3):

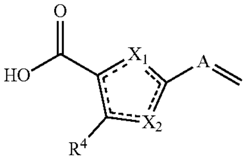

(IM-2)

+

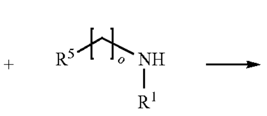

(RM-2)

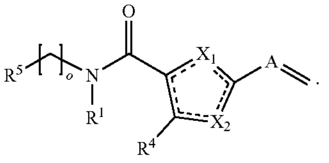

(IM-3)

3. The process of claim 2, further comprising a step of preparing the compound of formula (IM-2) by converting a compound of formula (RM-1) into the compound of formula (IM-1) followed by ester cleavage:

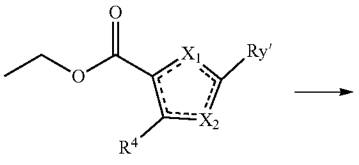

(RM-1)

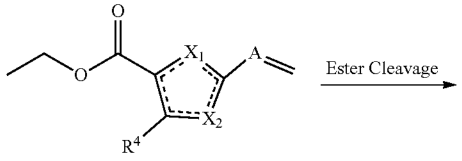

(IM-1)

-continued

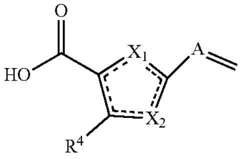

(IM-2)

wherein $R_{y'}$ represents hydrogen or halogen.

4. The process of claim 3, wherein the compound of formula (IM-1) is prepared according to one of the following reaction schemes:

(a) reaction scheme a):

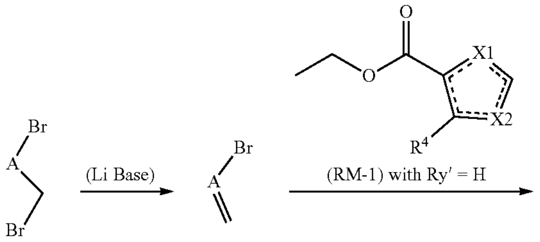

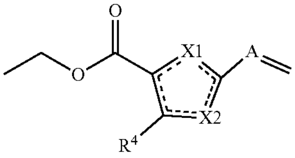

; or (IM-1)

(b) reaction scheme b

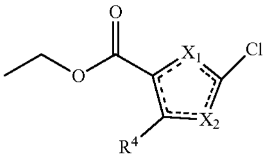

(RM-1)

+

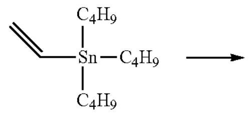

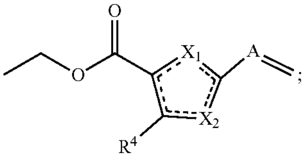

; or (IM-1)

(c) reaction scheme c)

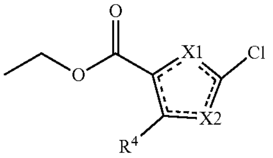

(RM-1)

+

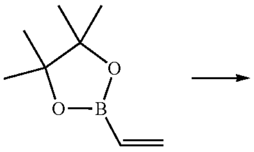

-continued

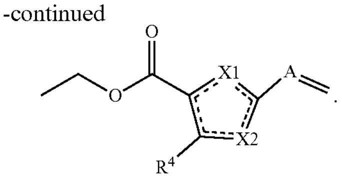

(IM-1)

5. The process of claim 3, wherein the preparation of the compound of formula (IM-2) from the compound of formula (RM-1) via the compound of formula (IM-1) is carried out in one process step in a one-pot reaction.

6. The process according to claim 1, wherein $R^5$ represents a monocyclic heteroaryl group optionally substituted with 1 to 3 substituents independently selected from $C_1$-$C_3$-alkyl, halogen, and $C_1$-$C_3$-halogenoalkyl.

7. The process of 1, comprising the following reaction steps Step 1, Step 2, and Step 3:

Step 1 selected from Scheme (a), Scheme (b), and Scheme (c), followed by an Ester Cleavage step:

Scheme (a)

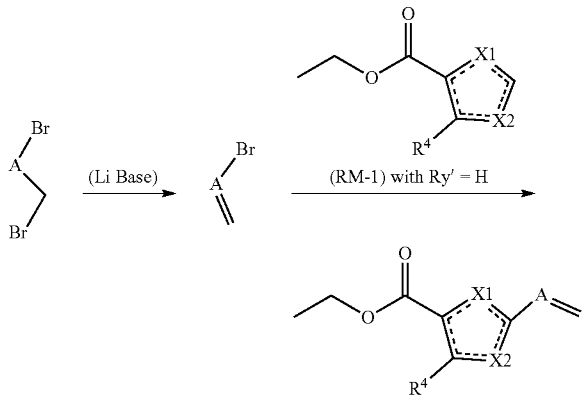

(IM-1)

Scheme (b)

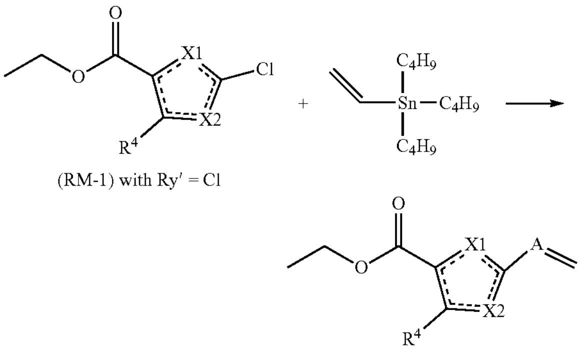

(RM-1) with Ry' = Cl (IM-1)

Scheme (c)

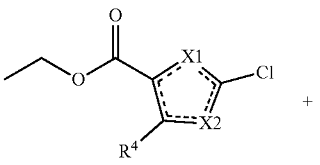

(RM-1) with Ry' = Cl

-continued

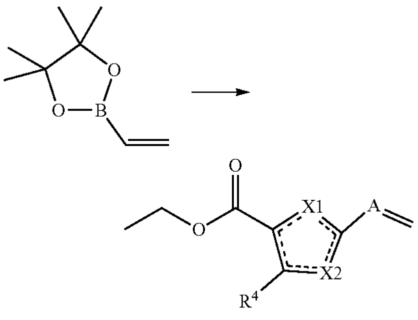

(IM-1)

Ester Cleavage step

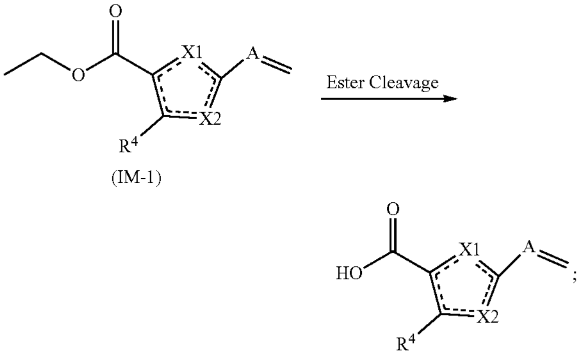

(IM-1)

(IM-2)

Step 2

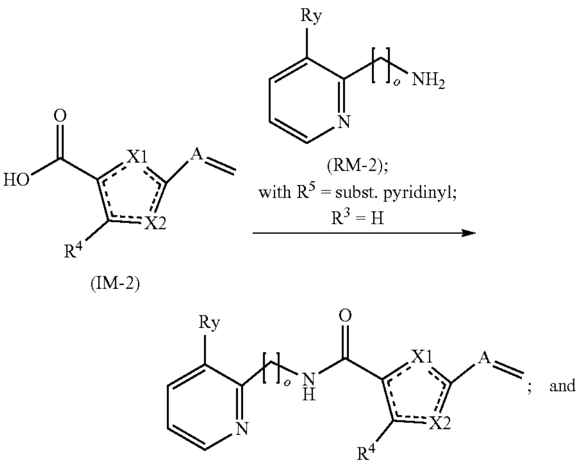

(IM-2)

; and (IM-3);
with $R^5$ = subst. pyridinyl;
$R^1$ = H

Step 3

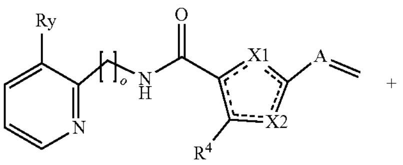

(IM-3);
with $R^5$ = subst. pyridinyl;
$R^1$ = H

-continued

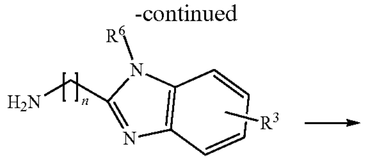

(RM-3);
with $R^2 = H$

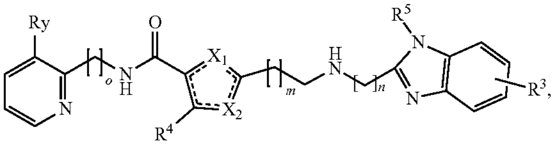

(I);
with $R^5$ = subst. pyridinyl;
$R^1, R^2 = H$ wherein $R_y$ is selected from $C_1$-$C_3$-alkyl, halogen, and $C_1$-$C_3$-halogenoalkyl.

8. The process of claim 1, wherein at least one of the following conditions is fulfilled:

A represents a CH-group;
m represents 1;
o represents 1;
$R^1$ and $R^2$ each represent hydrogen;
$R^4$ represents hydrogen;
$R^6$ represents hydrogen;
$R^3$ represents hydrogen;
$X^1$ is N and $X^3$ is O or S, forming a group

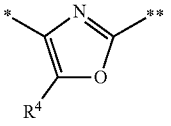

or

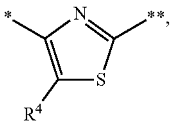

or
$X^1$ is O or S and $X^2$ is N, forming a group

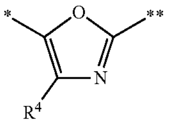

or

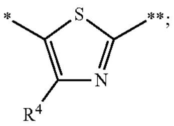

wherein in each case * indicates the binding position to the carbonyl-group and ** indicates the other binding position.

9. The process of claim 1, wherein the compound of formula (I) or pharmaceutically acceptable salt thereof is a compound of formula (II) or pharmaceutically acceptable salt thereof (II)

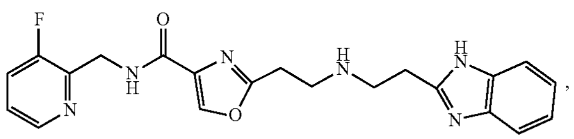

wherein the process comprises the following reaction steps Step 1-a, Step 2-a, and Step 3-a: Step 1-a selected from Scheme (a), Scheme (b), and Scheme (c), followed by an Ester Cleavage step:

Scheme (a)

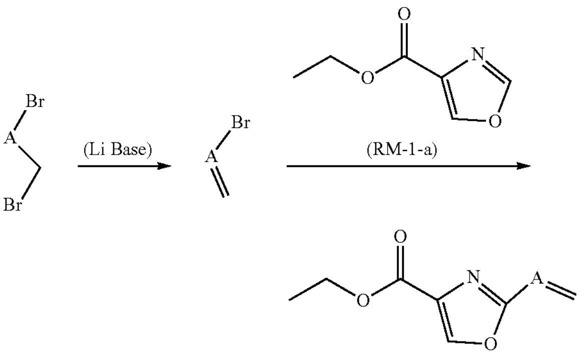

(IM-1)

Scheme (b)

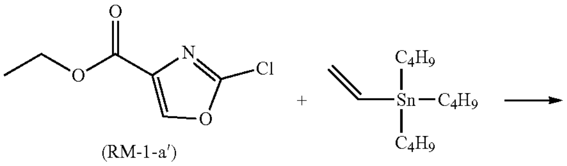

(RM-1-a')

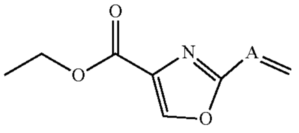

(IM-1)

Scheme (c)

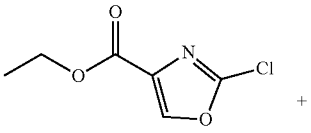

(RM-1-a')

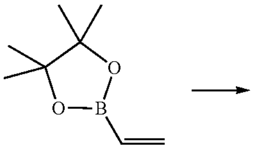

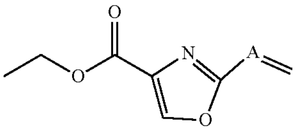

(IM-1)

Ester Cleavage step

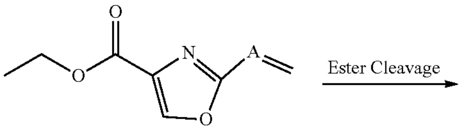

(IM-1)

-continued

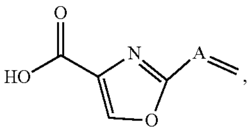

, wherein A represents a CH-group;

(IM-2)

Step 2-a

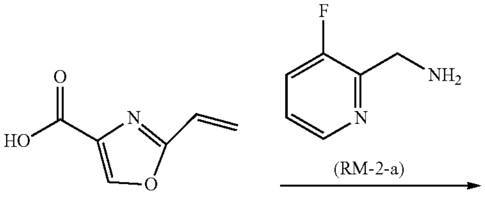

(IM-2-a)

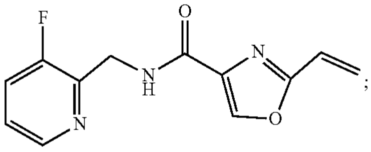

; and (IM-3-b)

Step 3-a

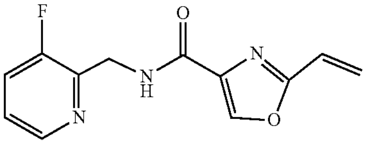

+

(IM-3-b)

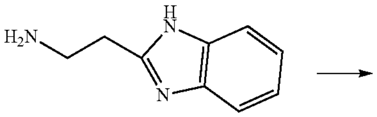

(RM-3-a)

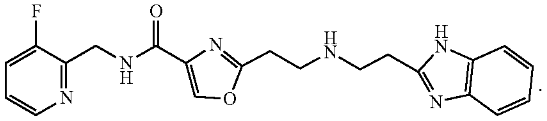

(II)

10. The process of claim 1, wherein the compound of formula (I) or pharmaceutically acceptable salt thereof is a compound of formula (II') or pharmaceutically acceptable salt thereof (II')

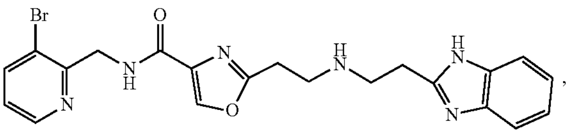

, wherein the process comprises the following reaction steps Step 1-a, Step 2-a, and Step 3-a: Step 1-a selected from Scheme (a), Scheme (b), and Scheme (c), followed by an Ester Cleavage step:

Scheme (a)

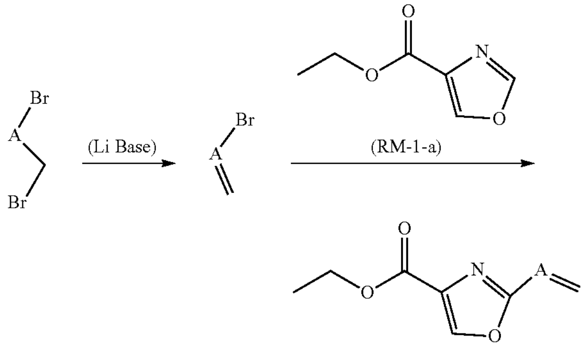

(IM-1)

Scheme (b)

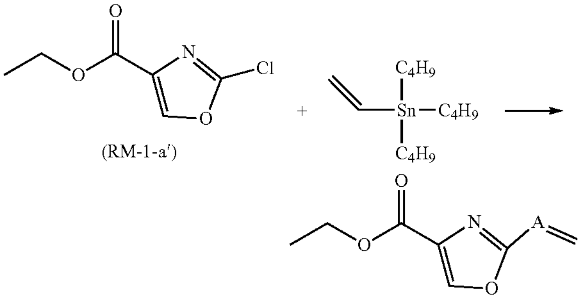

(IM-1)

Scheme (c)

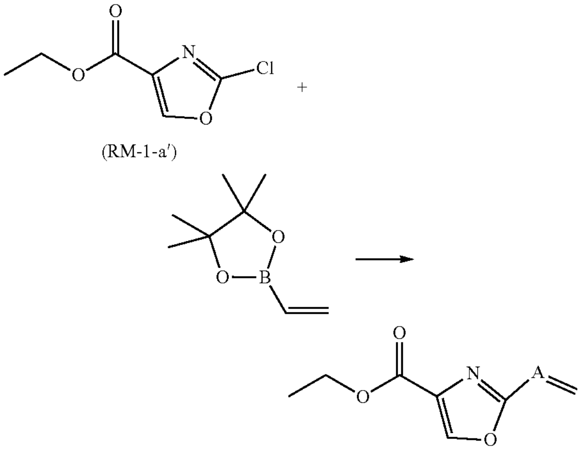

(IM-1)

Ester Cleavage step

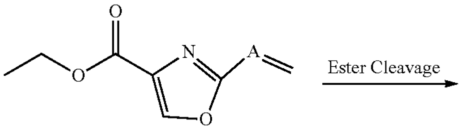

(IM-1)

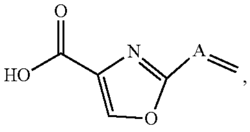

, wherein A represents a CH-group;

(IM-2)

-continued

Step 2-a

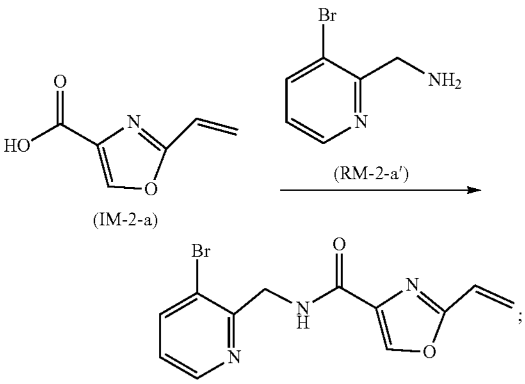

(RM-2-a')

(IM-2-a)

; and (IM-3-b')

Step 3-a

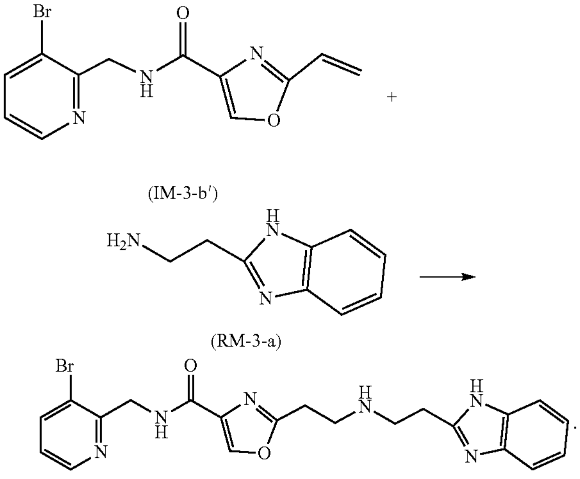

(IM-3-b')

(RM-3-a)

(II')

11. The process of claim 1, further comprising a step of converting the compound of formula (I) into a pharmaceutically acceptable salt or solvate thereof based on an acid selected from the group consisting of benzoic acid, citric acid, fumaric acid, hydrochloric acid, lactic acid, malic acid, maleic acid, methanesulfonic acid, phosphoric acid, succinic acid, sulfuric acid, tartaric acid, and toluenesulfonic acid.

12. The process of claim 9, further comprising a step of converting the compound of formula (II) into a pharmaceutically acceptable salt or solvate thereof based on an acid selected from the group consisting of benzoic acid, citric acid, fumaric acid, hydrochloric acid, lactic acid, malic acid, maleic acid, methanesulfonic acid, phosphoric acid, succinic acid, sulfuric acid, tartaric acid, and toluenesulfonic acid.

13. The process of claim 10, further comprising a step of converting the compound of formula (II') into a pharmaceutically acceptable salt or solvate thereof based on an acid selected from the group consisting of benzoic acid, citric acid, fumaric acid, hydrochloric acid, lactic acid, malic acid, maleic acid, methanesulfonic acid, phosphoric acid, succinic acid, sulfuric acid, tartaric acid, and toluenesulfonic acid.

14. The process of claim 11, where the pharmaceutically acceptable salt of the compound of formula (I) is a salt selected from the group consisting of mono-HCl salt (1HCl), triple-HCl salt (3HCl), $H_2SO_4$ salt, $0.5H_3PO_4$ salt, and $1H_3PO_4$ salt.

15. The process of claim 12, where the pharmaceutically acceptable salt of the compound of formula (II) is a salt selected from the group consisting of mono-HCl salt (1HCl), triple-HCl salt (3HCl), $H_2SO_4$ salt, $0.5H_3PO_4$ salt, and $1H_3PO_4$ salt.

16. The process of claim 13, where the pharmaceutically acceptable salt of the compound of formula (II') is a salt selected from the group consisting of mono-HCl salt (1HCl), triple-HCl salt (3HCl), $H_2SO_4$ salt, $0.5H_3PO_4$ salt, and $1H_3PO_4$ salt.

17. The process of claim 1, wherein the at least one step is carried out in one telescoped one-pot reaction.

18. The process of claim 7, wherein the Step 1 and Step 2 are carried out in one telescoped one-pot reaction.

19. The process of claim 9, wherein the Step 1-a and Step 2-a are carried out in one telescoped one-pot reaction.

20. The process of claim 7, further comprising a step of converting the compound of formula (I) into a pharmaceutically acceptable salt or solvate thereof based on an acid selected from the group consisting of benzoic acid, citric acid, fumaric acid, hydrochloric acid, lactic acid, malic acid, maleic acid, methanesulfonic acid, phosphoric acid, succinic acid, sulfuric acid, tartaric acid, and toluenesulfonic acid, wherein the Step 3 and the step of converting the compound of formula (I) into the pharmaceutically acceptable salt or solvate thereof is carried out in one telescoped one-pot reaction.

21. The process of claim 9, further comprising a step of converting the compound of formula (II) into a pharmaceutically acceptable salt or solvate thereof based on an acid selected from the group consisting of benzoic acid, citric acid, fumaric acid, hydrochloric acid, lactic acid, malic acid, maleic acid, methanesulfonic acid, phosphoric acid, succinic acid, sulfuric acid, tartaric acid, and toluenesulfonic acid, wherein the Step 3-a and the step of converting the compound of formula (II) into the pharmaceutically acceptable salt or solvate thereof is carried out in one telescoped one-pot reaction.

22. The process of claim 10, further comprising a step of converting the compound of formula (II') into a pharmaceutically acceptable salt or solvate thereof based on an acid selected from the group consisting of benzoic acid, citric acid, fumaric acid, hydrochloric acid, lactic acid, malic acid, maleic acid, methanesulfonic acid, phosphoric acid, succinic acid, sulfuric acid, tartaric acid, and toluenesulfonic acid, and wherein Step 3-a and the step of converting the compound of formula (II') into the pharmaceutically acceptable salt or solvate thereof is carried out in one telescoped one-pot reaction.

* * * * *